US006593354B2

(12) United States Patent
Clark et al.

(10) Patent No.: US 6,593,354 B2
(45) Date of Patent: Jul. 15, 2003

(54) SUBSTITUTED BENZOXAZOLE COMPOUNDS

(75) Inventors: David Edward Clark, West Malling (GB); Paul Robert Eastwood, West Malling (GB); Neil Victor Harris, West Malling (GB); Clive McCarthy, West Malling (GB); Andrew David Morley, West Malling (GB); Stephen Dennis Pickett, West Malling (GB)

(73) Assignee: Aventis Pharma Limited, West Malling (GB)

( * ) Notice: Subject to any disclaimer, the term of this patent is extended or adjusted under 35 U.S.C. 154(b) by 0 days.

(21) Appl. No.: 09/925,110

(22) Filed: Aug. 9, 2001

(65) Prior Publication Data
US 2002/0137782 A1 Sep. 26, 2002

Related U.S. Application Data

(63) Continuation of application No. PCT/GB00/00553, filed on Feb. 16, 2000.
(60) Provisional application No. 60/141,445, filed on Jun. 29, 1999.

(30) Foreign Application Priority Data

Feb. 16, 1999 (GB) ................................................ 9903532

(51) Int. Cl.$^7$ ..................... A61K 31/423; C07D 263/58
(52) U.S. Cl. ....................................... 514/375; 548/222
(58) Field of Search ........................... 548/222; 514/375

(56) References Cited

U.S. PATENT DOCUMENTS 4,025,637 A    5/1977   Dunwell et al.
4,100,168 A    7/1978   Dunwell et al.

FOREIGN PATENT DOCUMENTS

| JP | 10330369 A | 12/1998 |
| WO | WO 96/22966 | 8/1996 |
| WO | WO 97/36862 | 10/1997 |
| WO | WO 99/24398 | 5/1999 |
| WO | WO 00/05223 | 2/2000 |
| WO | WO 00/5224 | 2/2000 |

Primary Examiner—Joseph K. McKane
Assistant Examiner—Rebecca Anderson
(74) Attorney, Agent, or Firm—Ronald G. Ort

(57) ABSTRACT

The invention is directed to physiologically active compounds of formula (Ia):

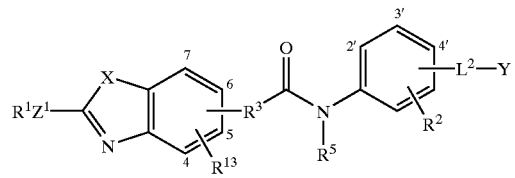

wherein $R^1$ is optionally substituted aryl or optionally substituted heteroaryl; $R^2$ is hydrogen, halogen, lower alkyl or lower alkoxy; $R^3$ is alkylene, alkenylene or alkynylene; $R^5$ is hydrogen or lower alkyl; $L^2$ is optionally substituted alkylene or alkenylene; Y is carboxy; and $Z^1$ is $NR^5$; and the corresponding N-oxides, and their prodrugs; and pharmaceutically acceptable salts and solvates (e.g. hydrates) of such compounds and their N-oxides and prodrugs. Such compounds have valuable pharmaceutical properties, in particular the ability to regulate the interaction of VCAM-1 and fibronectin with the integrin VLA-4 ($\alpha 4\beta 1$).

24 Claims, No Drawings

SUBSTITUTED BENZOXAZOLE COMPOUNDS

This application is a continuation of PCT/GB00/00553, filed Feb. 16, 2000, which claims priority from GB Application No. 9903532.1, filed Feb. 16, 1999, and U.S. Provisional Application No. 60/141,445, filed Jun. 29, 1999.

This invention is directed to substituted bicyclic compounds, their preparation, pharmaceutical compositions containing these compounds, and their pharmaceutical use in the treatment of disease states capable of being modulated by the inhibition of cell adhesion.

Cell adhesion is a process by which cells associate with each other, migrate towards a specific target or localise within the extra-cellular matrix. Many of the cell-cell and cell-extra-cellular matrix interactions are mediated by protein ligands (e.g. fibronectin, VCAM-1 and vitronectin) and their integrin receptors [e.g. α5β1 (VLA-5), α4β1 (VLA-4) and αVβ3]. Recent studies have shown these interactions to play an important part in many physiological (e.g. embryonic development and wound healing) and pathological conditions (e.g. tumour-cell invasion and metastasis, inflammation, atherosclerosis and autoimmune disease).

A wide variety of proteins serve as ligands for integrin receptors. In general, the proteins recognised by integrins fall into one of three classes: extracellular matrix proteins, plasma proteins and cell surface proteins. Extracellular matrix proteins such as collagen fibronectin, fibrinogen, laminin, thrombospondin and vitronectin bind to a number of integrins. Many of the adhesive proteins also circulate in plasma and bind to activated blood cells. Additional components in plasma that are ligands for integrins include fibrinogen and factor X. Cell bound complement C3bi and several transmembrane proteins, such as Ig-like cell adhesion molecule (ICAM-1,2,3) and vascular cell adhesion molecule (VCAM-1), which are members of the Ig superfamily, also serve as cell-surface ligands for some integrins.

Integrins are heterodimeric cell surface receptors consisting of two subunits called α and β. There are at least fifteen different α-subunits (α1–α9, α-L, α-M, α-X, α-IIb, α-V and α-E) and at least least seven different β (β1–β7) subunits. The integrin family can be subdivided into classes based on the β subunits, which can be associated with one or more α-subunits. The most widely distributed integrins belong to the β1 class, also known as the very late antigens (VLA). The second class of integrins are leukocyte specific receptors and consist of one of three α-subunits (α-L, α-M or α-X) complexed with the β2 protein. The cytoadhesins α-IIbβ3 and α-Vβ3, constitute the third class of integrins.

The present invention principally relates to agents which modulate the interaction of the ligand VCAM-1 with its integrin receptor α4β1 (VLA-4), which is expressed on numerous hematopoietic cells and established cell lines, including hematopoietic precursors, peripheral and cytotoxic T lymphocytes, B lymphocytes, monocytes, thymocytes and eosinophils.

The integrin α4β1 mediates both cell-cell and cell-matrix interactions. Cells expressing α4β1 bind to the carboxy-terminal cell binding domain (CS-1) of the extracellular matrix protein fibronectin, to the cytokine-inducible endothelial cell surface protein VCAM-1, and to each other to promote homotypic aggregation. The expression of VCAM-1 by endothelial cells is up-regulated by proinflammatory cytokines such as INF-γ, TNF-α, IL-1β and IL-4.

Regulation of α4β1 mediated cell adhesion is important in numerous physiological processes, including T-cell proliferation, B-cell localisation to germinal centres, and adhesion of activated T-cells and eosinophils to endothelial cells. Evidence for the involvement of VLA-4/VCAM-1 interaction in various disease processes such as melanoma cell division in metastasis, T-cell infiltration of synovial membranes in rheumatoid arthritis, autoimmune diabetes, collitis and leukocyte penetration of the blood-brain barrier in experimental autoimmune encephalomyelitis, atherosclerosis, peripheral vascular disease, cardiovascular disease and multiple sclerosis, has been accumulated by investigating the role of the peptide CS-1 (the variable region of fibronectin to which α4β1 binds via the sequence Leu-Asp-Val) and antibodies specific for VLA-4 or VCAM-1 in various in vitro and in vivo experimental models of inflammation. For example, in a Streptococcal cell wall-induced experimental model of arthritis in rats, intravenous administration of CS-1 at the initiation of arthritis suppresses both acute and chronic inflammation (S. M. Wahl et al., J. Clin. Invest., 1994, 94, pages 655–662). In the oxazalone-sensitised model of inflammation (contact hypersensitivity response) in mice, intravenous administration of anti-α4 specific monoclonal antibodies significantly inhibited (50–60% reduction in the ear swelling response) the efferent response (P. L. Chisholm et al. J. Immunol., 1993, 23, pages 682–688). In a sheep model of allergic bronchoconstriction, HP1/2, an anti-α4 monoclonal antibody given intravenously or by aerosol, blocked the late response and the development of airway hyperresponsiveness (W. M. Abraham et al. J. Clin. Invest., 1994, 93 pages 776–787).

We have now found a novel group of substituted bicyclic compounds which have valuable pharmaceutical properties, in particular the ability to regulate the interaction of VCAM-1 and fibronectin with the integrin VLA-4 (α4β1).

Thus, in one aspect, the present invention is directed to compounds of general formula (I):

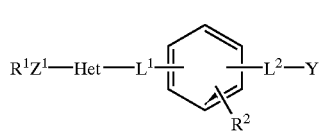

(I)

wherein

Het represents a saturated, partially saturated or fully unsaturated 8 to 10 membered bicyclic ring system containing at least one heteroatom selected from O, S or N, optionally substituted by one or more aryl group substituents;

$R^1$ represents optionally substituted aryl or optionally substituted heteroaryl;

$R^2$ represents hydrogen, halogen, lower alkyl or lower alkoxy;

$R^3$ is an alkylene chain, an alkenylene chain or an alkynylene chain;

$R^4$ is a direct bond, cycloalkylene, heterocycloalkylene, arylene, heteroaryldiyl, —C(=$Z^2$)—$NR^5$—, —$NR^5$—C(=$Z^2$)—, —$Z^2$—, —C(=O)—, —C(=$NOR^5$)—, —$NR^5$—, —$NR^5$—C(=$Z^2$)—$NR^5$—, —$SO_2$—$NR^5$—, —$NR^5$—$SO_2$—, —O—C(=O)—, —C(=O)—O—, —$NR^5$—C(=O)—O— or —O—C(=O)—$NR^5$—;

$R^5$ represents hydrogen or lower alkyl;

$R^6$ represents alkyl, alkenyl, alkynyl, aryl, arylalkyl, arylalkenyl, arylalkynyl, cycloalkyl, cycloalkylalkyl, cycloalkylalkenyl, cycloalkylalkynyl, cycloalkenyl, cycloalkenylalkyl, heteroaryl, heteroarylalkyl, heteroarylalkenyl, heteroarylalkynyl, heterocycloalkyl or heterocycloalkylalkyl;

$L^1$ represents a —$R^3$—$R^4$— linkage;

$L^2$ represents an alkylene or alkenylene linkage each optionally substituted by $R^6$ or by alkyl substituted by hydroxy, —$OR^6$, —O—C(=O)—$R^6$ or —$NY^1Y^2$;

Y is carboxy or an acid bioisostere;

$Y^1$ and $Y^2$ are independently hydrogen, alkenyl, alkyl, aryl, arylalkyl, cycloalkyl, heteroaryl or heteroarylalkyl; or the group —$NY^1Y^2$ may form a cyclic amine;

$Z^1$ represents $NR^5$; and $Z^2$ is O or S;

and the corresponding N-oxides, and their prodrugs; and pharmaceutically acceptable salts and solvates (e.g. hydrates) of such compounds and their N-oxides and prodrugs, but excluding compounds where an oxygen, nitrogen or sulphur atom is attached directly to a carbon-carbon multiple bond of an alkenyl, alkenylene, alkynyl, alkynylene or cycloalkenyl residue.

In the present specification, the term "compounds of the invention", and equivalent expressions, are meant to embrace compounds of general formula (I) as hereinbefore described, which expression includes the prodrugs, the pharmaceutically acceptable salts, and the solvates, e.g. hydrates, where the context so permits. Similarly, reference to intermediates, whether or not they themselves are claimed, is meant to embrace their salts, and solvates, where the context so permits. For the sake of clarity, particular instances when the context so permits are sometimes indicated in the text, but these instances are purely illustrative and it is not intended to exclude other instances when the context so permits.

As used above, and throughout the description of the invention, the following terms, unless otherwise indicated, shall be understood to have the following meanings:

"Patient" includes both human and other mammals.

"Acid bioisostere" means a group which has chemical and physical similarities producing broadly similar biological properties to a carboxy group (see Lipinski, Annual Reports in Medicinal Chemistry, 1986,21, p283 "Bioisosterism In Drug Design"; Yun, Hwahak Sekye, 1993,33, p576–579 "Application Of Bioisosterism To New Drug Design"; Zhao, Huaxue Tongbao, 1995, p34–38 "Bioisosteric Replacement And Development Of Lead Compounds In Drug Design"; Graham, Theochem, 1995,343, p105–109 "Theoretical Studies Applied To Drug Design:ab initio Electronic Distributions In Bioisosteres"). Examples of suitable acid bioisosteres include: —C(=O)—NHOH, —C(=O)—$CH_2$OH, —C(=O)—$CH_2$SH, —C(=O)—NH—CN, sulpho, phosphono, alkylsulphonylcarbamoyl, tetrazolyl, arylsulphonylcarbamoyl, heteroarylsulphonylcarbamoyl, N-methoxycarbamoyl, 3-hydroxy-3-cyclobutene-1,2-dione, 3,5-dioxo-1,2,4-oxadiazolidinyl or heterocyclic phenols such as 3-hydroxyisoxazolyl and 3-hydoxy-1-methylpyrazolyl.

"Acyl" means an H—CO— or alkyl-CO— group in which the alkyl group is as described herein.

"Acylamino" is an acyl-NH— group wherein acyl is as defined herein.

"Alkenyl" means an aliphatic hydrocarbon group containing a carbon-carbon double bond and which may be straight or branched having about 2 to about 15 carbon atoms in the chain. Preferred alkenyl groups have 2 to about 12 carbon atoms in the chain; and more preferably 2 to about 6 carbon atoms (e.g. 2 to 4 carbon atoms) in the chain. "Branched", as used herein and throughout the text, means that one or more lower alkyl groups such as methyl, ethyl or propyl are attached to a linear chain; here a linear alkenyl chain. "Lower alkenyl" means about 2 to about 4 carbon atoms in the chain which may be straight or branched. Exemplary alkenyl groups include ethenyl, propenyl, n-butenyl, i-butenyl, 3-methylbut-2-enyl, n-pentenyl, heptenyl, octenyl, cyclohexylbutenyl and decenyl.

"Alkenylene" means an aliphatic bivalent radical derived from a straight or branched alkenyl group, in which the alkenyl group is as described herein. Exemplary alkenylene radicals include vinylene and propylene.

"Alkoxy" means an alkyl-O— group in which the alkyl group is as described herein. Exemplary alkoxy groups include methoxy, ethoxy, n-propoxy, i-propoxy, n-butoxy and heptoxy.

"Alkoxyalkoxy" means an alkyl-O-alkyl-O— group wherein the alkyl groups independently are as defined above. Examples of alkoxyalkoxyl include methoxymethoxy, methoxyethoxy, ethoxyethoxy and the like.

"Alkoxycarbonyl" means an alkyl-O—CO— group in which the alkyl group is as described herein. Exemplary alkoxycarbonyl groups include methoxy- and ethoxycarbonyl.

"Alkyl" means, unless otherwise specified, an aliphatic hydrocarbon group which may be straight or branched having about 1 to about 15 carbon atoms in the chain optionally substituted by alkoxy or by one or more halogen atoms. Particular alkyl groups have from 1 to about 6 carbon atoms. "Lower alkyl" as a group or part of a lower alkoxy, lower alkylthio, lower alkylsulphinyl or lower alkylsulphonyl group means unless otherwise specified, an aliphatic hydrocarbon group which may be straight or branched having 1 to about 4 carbon atoms in the chain. Exemplary alkyl groups include methyl, ethyl, n-propyl, i-propyl, n-butyl, s-butyl, t-butyl, n-pentyl, 3-pentyl, heptyl, octyl, nonyl, decyl and dodecyl.

"Alkylene" means an aliphatic bivalent radical derived from a straight or branched alkyl group, in which the alkyl group is as described herein. Exemplary alkylene radicals include methylene, ethylene and trimethylene.

"Alkylenedioxy" means an —O-alkylene-O— group in which alkylene is as defined above. Exemplary alkylenedioxy groups include methylenedioxy and ethylenedioxy.

"Alkylsulphinyl" means an alkyl-SO— group in which the alkyl group is as previously described. Preferred alkylsulphinyl groups are those in which the alkyl group is $C_{1-4}$alkyl.

"Alkylsulphonyl" means an alkyl-$SO_2$— group in which the alkyl group is as previously described. Preferred alkylsulphonyl groups are those in which the alkyl group is $C_{1-4}$alkyl.

"Alkylsulphonylcarbamoyl" means an alkyl-$SO_2$—NH—C(=O)— group in which the alkyl group is as previously described. Preferred alkylsulphonylcarbamoyl groups are those in which the alkyl group is $C_{1-4}$alkyl.

"Alkylthio" means an alkyl-S— group in which the alkyl group is as previously described. Exemplary alkylthio groups include methylthio, ethylthio, isopropylthio and heptylthio.

"Alkynyl" means an aliphatic hydrocarbon group containing a carbon-carbon triple bond and which may be straight or branched having about 2 to about 15 carbon atoms in the chain. Preferred alkynyl groups have 2 to about 12 carbon atoms in the chain; and more preferably 2 to about 6 carbon atoms (e.g. 2 to 4 carbon atoms) in the chain.

Exemplary alkynyl groups include ethynyl, propynyl, n-butynyl, i-butynyl, 3-methylbut-2-ynyl, and n-pentynyl.

"Alkynylene" means an aliphatic bivalent radical derived from a straight or branched alkynyl group, in which the alkynyl group is as described herein. Exemplary alkynylene radicals include ethynylene and propynylene.

"Aroyl" means an aryl-CO— group in which the aryl group is as described herein. Exemplary aroyl groups include benzoyl and 1- and 2-naphthoyl.

"Aroylamino" is an aroyl-NH— group wherein aroyl is as previously defined.

"Aryl" as a group or part of a group denotes: (i) an optionally substituted monocyclic or multicyclic aromatic carbocyclic moiety of about 6 to about 14 carbon atoms, such as phenyl or naphthyl; or (ii) an optionally substituted partially saturated multicyclic aromatic carbocyclic moiety in which an aryl and a cycloalkyl or cycloalkenyl group are fused together to form a cyclic structure, such as a tetrahydronaphthyl, indenyl or indanyl ring. Aryl groups may be substituted with one or more aryl group substituents which may be the same or different, where "aryl group substituent" includes, for example, acyl, acylamino, alkoxy, alkoxycarbonyl, alkylenedioxy, alkylsulphinyl, alkylsulphonyl, alkylthio, aroyl, aroylamino, aryl, arylalkyloxy, arylalkyloxycarbonyl, arylalkylthio, aryloxy, aryloxycarbonyl, arylsulphinyl, arylsulphonyl, arylthio, carboxy, cyano, halo, heteroaroyl, heteroaryl, heteroarylalkyloxy, heteroaroylamino, heteroaryloxy, hydroxy, nitro, trifluoromethyl, $Y^1Y^2N$—, $Y^1Y^2NCO$—, $Y^1Y^2NSO_2$—, $Y^1Y^2N$—$C_{2-6}$alkylene-$Z^1$—, alkylC(=O)-$Y^1N$—, alkylSO$_2$—$Y^1N$— or alkyl optionally substituted with aryl, heteroaryl, hydroxy, or $Y^1Y^2N$—. When $R^1$ is an optionally substituted aryl group, this may particularly represent optionally substituted phenyl.

"Arylalkenyl" means an aryl-alkenyl- group in which the aryl and alkenyl are as previously described. Preferred arylalkenyls contain a lower alkenyl moiety. Exemplary arylalkenyl groups include styryl and phenylallyl.

"Arylalkyl" means an aryl-alkyl- group in which the aryl and alkyl moieties are as previously described. Preferred arylalkyl groups contain a $C_{1-4}$alkyl moiety. Exemplary arylalkyl groups include benzyl, 2-phenethyl and naphthlenemethyl.

"Arylalkyloxy" means an arylalkyl-O— group in which the arylalkyl groups is as previously described. Exemplary arylalkyloxy groups include benzyloxy and 1 - or 2-naphthalenemethoxy.

"Arylalkyloxycarbonyl" means an arylalkyl-O—CO— group in which the arylalkyl groups is as previously described. An exemplary arylalkyloxycarbonyl group is benzyloxycarbonyl.

"Arylalkylthio" means an arylalkyl—S— group in which the arylalkyl group is as previously described. An exemplary arylalkylthio group is benzylthio.

"Arylalkynyl" means an aryl-alkynyl- group in which the aryl and alkynyl are as previously described. Exemplary arylalkynyl groups include phenylethynyl and 3-phenylbut-2-ynyl.

"Arylene" means an optionally substituted bivalent radical derived from an aryl group. Exemplary arylene groups include optionally substituted phenylene, naphthylene and indanylene. Suitable substituents include one or more "aryl group substituents" as defined above, particularly halogen, methyl or methoxy.

"Aryloxy" means an aryl-O— group in which the aryl group is as previously described. Exemplary aryloxy groups include optionally substituted phenoxy and naphthoxy.

"Aryloxycarbonyl" means an aryl-O—C(=O)— group in which the aryl group is as previously described. Exemplary aryloxycarbonyl groups include phenoxycarbonyl and naphthoxycarbonyl.

"Arylsulphinyl" means an aryl-SO— group in which the aryl group is as previously described.

"Arylsulphonyl" means an aryl-SO$_2$— group in which the aryl group is as previously described.

"Arylsulphonylcarbamoyl" means an aryl-SO$_2$—NH—C (=O)— group in which the aryl group is as previously described.

"Arylthio" means an aryl-S— group in which the aryl group is as previously described. Exemplary arylthio groups include phenylthio and naphthylthio.

"Cyclic amine" means a 3 to 8 membered monocyclic cycloalkyl ring system where one of the ring carbon atoms is replaced by nitrogen and which (i) may optionally contain an additional heteroatom selected from O, S or NY$^3$ (where Y$^3$ is hydrogen, alkyl, arylalkyl, and aryl) and (ii) may be fused to additional aryl or heteroaryl ring to form a bicyclic ring system. Exemplary cyclic amines include pyrrolidine, piperidine, morpholine, piperazine, indoline and pyrindoline.

"Cycloalkenyl" means a non-aromatic monocyclic or multicyclic ring system containing at least one carbon-carbon double bond and having about 3 to about 10 carbon atoms. Exemplary monocyclic cycloalkenyl rings include cyclopentenyl, cyclohexenyl or cycloheptenyl.

"Cycloalkenylalkyl" means a cycloalkenyl-alkyl- group in which the cycloalkenyl and alkyl moieties are as previously described. Exemplary cycloalkenylalkyl groups include cyclopentenylmethyl, cyclohexenylmethyl or cycloheptenylmethyl.

"Cycloalkenylene" means a bivalent radical derived from an unsaturated monocyclic hydrocarbon of about 3 to about 10 carbon atoms by removing a hydrogen atom from each of two different carbon atoms of the ring. Exemplary cycloalkenylene radicals include cyclopentenylene and cyclohexenylene.

"Cycloalkyl" means a saturated monocyclic or bicyclic ring system of about 3 to about 10 carbon atoms optionally substituted by oxo. Exemplary monocyclic cycloalkyl rings include $C_{3-8}$cycloalkyl rings such as cyclopropyl, cyclopentyl, cyclohexyl and cycloheptyl.

"Cycloalkylalkyl" means a cycloalkyl-alkyl- group in which the cycloalkyl and alkyl moieties are as previously described. Exemplary monocyclic cycloalkylalkyl groups include cyclopropylmethyl, cyclopentylmethyl, cyclohexylmethyl and cycloheptylmethyl.

"Cycloalkylene" means a bivalent radical derived from a saturated monocyclic hydrocarbon of about 3 to about 10 carbon atoms by removing a hydrogen atom from each of two different carbon atoms of the ring. Exemplary cycloalkenylene radicals include cyclopentylene and cyclohexylene.

"Halo" or "halogen" means fluoro, chloro, bromo, or iodo. Preferred are fluoro or chloro.

"Heteroaroyl" means a heteroaryl-C(=O)— group in which the heteroaryl group is as described herein. Exemplary groups include pyridylcarbonyl.

"Heteroaroylamino" means a heteroaroyl-NH— group in which the heteroaryl moiety are as previously described.

"Heteroaryl" as a group or part of a group denotes: (i) an optionally substituted aromatic monocyclic or multicyclic organic moiety of about 5 to about 10 ring members in which one or more of the ring members is/are element(s) other than carbon, for example nitrogen, oxygen or sulphur (examples of such groups include benzimidazolyl, benzthiazolyl, furyl, imidazolyl, indolyl, indolizinyl, isoxazolyl, isoquinolinyl, isothiazolyl, oxadiazolyl, pyrazinyl, pyridazinyl, pyrazolyl, pyridyl, pyrimidinyl, pyrrolyl, quinazolinyl, quinolinyl, 1,3,4-thiadiazolyl, thiazolyl, thienyl and triazolyl groups, optionally substituted by one or more aryl group substituents as defined above); (ii) an optionally substituted partially saturated multicyclic heterocarbocyclic moiety in which a heteroaryl and a cycloalkyl or cycloalkenyl group are fused together to form a cyclic structure (examples of such groups include pyrindanyl groups). Optional substituents include one or more "aryl group substituents" as defined above.

"Heteroarylalkenyl" means a heteroaryl-alkenyl- group in which the heteroaryl and alkenyl moieties are as previously described. Preferred heteroarylalkenyl groups contain a lower alkenyl moiety. Exemplary heteroarylalkenyl groups include pyridylethenyl and pyridylallyl.

"Heteroarylalkyl" means a heteroaryl-alkyl- group in which the heteroaryl and alkyl moieties are as previously described. Preferred heteroarylalkyl groups contain a $C_{1-4}$alkyl moiety. Exemplary heteroarylalkyl groups include pyridylmethyl.

"Heteroarylalkyloxy" means an heteroarylalkyl-O— group in which the heteroarylalkyl group is as previously described. Exemplary heteroaryloxy groups include optionally substituted pyridylmethoxy.

"Heteroarylalkynyl" means a heteroaryl-alkynyl- group in which the heteroaryl and alkynyl moieties are as previously described. Exemplary heteroarylalkenyl groups include pyridylethynyl and 3-pyridylbut-2-ynyl.

"Heteroaryldiyl" means a bivalent radical derived from an aromatic monocyclic or multicyclic organic moiety of about 5 to about 10 ring members in which one or more of the ring members is/are element(s) other than carbon, for example nitrogen, oxygen or sulphur, and optionally substituted by one or more "aryl group substituents" as defined above.

"Heteroaryloxy" means an heteroaryl-O— group in which the heteroaryl group is as previously described. Exemplary heteroaryloxy groups include optionally substituted pyridyloxy.

"Heteroarylsulphonylcarbamoyl" means a heteroaryl-$SO_2$—NH—C(=O)— group in which the heteroaryl group is as previously described.

"Heterocycle" denotes an optionally substituted saturated, partially saturated or fully unsaturated monocyclic organic moiety of 5 or 6 ring members in which one or more of the ring members is/are element(s) other than carbon, for example nitrogen, oxygen or sulphur. Exemplary 5 or 6 membered heterocycles include furyl, imidazolyl, isoxazolyl, isothiazolyl, oxadiazolyl, oxazolyl, oxazinyl, piperidinyl, pyrazinyl, pyridazinyl, pyrazolyl, pyridyl, pyrimidinyl, pyrrolyl, pyrrolidinyl, pyrrolinyl, 1,3,4-thiadiazolyl, thiazolyl, thienyl and triazolyl groups. Optional substituents include one or more "aryl group substituents" as defined above.

"Heterocycloalkyl" means: (i) a cycloalkyl group of about 3 to 7 ring members which contains one or more heteroatoms selected from O, S or $NY^3$; (ii) an optionally substituted partially saturated multicyclic heterocarbocyclic moiety in which an aryl (or heteroaryl ring) and a heterocycloalkyl group are fused together to form a cyclic structure (examples of such groups include chromanyl, dihydrobenzofuranyl, indolinyl and pyrindolinyl groups).

"Heterocycloalkylalkyl" means a heterocycloalkyl-alkyl- group in which the heterocycloalkyl and alkyl moieties are as previously described.

"Heterocycloalkylene" means a bivalent radical derived from a saturated monocyclic hydrocarbon of about 5 to about 7 atoms, which contains one or more heteroatoms selected from O, S or $NY^4$ (where $Y^4$ is hydrogen, alkyl, arylalkyl, and aryl) and is optionally substituted by oxo, by removing a hydrogen atom from each of two different carbon atoms of the ring, or when $NY^4$ is NH by removing a hydrogen atom from one carbon atom of the ring and a hydrogen atom from the NH, or when the ring contains two $NY^4$ heteroatoms and $NY^4$ is NH by removing a hydrogen atom from both nitrogen atoms.

"Prodrug" means a compound which is convertible in vivo by metabolic means (e.g. by hydrolysis) to a compound of formula (I), including N-oxides thereof. For example an ester of a compound of formula (I) containing a hydroxy group may be convertible by hydrolysis in vivo to the parent molecule. Alternatively an ester of a compound of formula (I) containing a carboxy group may be convertible by hydrolysis in vivo to the parent molecule.

Suitable esters of compounds of formula (I) containing a hydroxy group, are for example acetates, citrates, lactates, tartrates, malonates, oxalates, salicylates, propionates, succinates, fumarates, maleates, methylene-bis-β-hydroxynaphthoates, gentisates, isethionates, di-p-toluoyltartrates, methanesulphonates, ethanesulphonates, benzenesulphonates, p-toluenesulphonates, cyclohexylsulphamates and quinates.

Suitable esters of compounds of formula (I) containing a carboxy group, are for example those described by F. J. Leinweber, Drug Metab. Res., 1987, 18, page 379.

Suitable esters of compounds of formula (I) containing both a carboxy group and a hydroxy group within the moiety —$L^2$—Y, include lactones, formed by loss of water between said carboxy and hydroxy groups. Examples of lactones include caprolactones and butyrolactones.

An especially useful class of esters of compounds of formula (I) containing a hydroxy group, may be formed from acid moieties selected from those described by Bundgaard et. al., J. Med. Chem., 1989, 32, page 2503–2507, and include substituted (aminomethyl)-benzoates, for example dialkylamino-methylbenzoates in which the two alkyl groups may be joined together and/or interrupted by an oxygen atom or by an optionally substituted nitrogen atom, e.g. an alkylated nitrogen atom, more especially (morpholino-methyl)benzoates, e.g. 3- or 4-(morpholino-methyl)-benzoates, and (4-alkylpiperazin-1 -yl)benzoates, e.g. 3- or 4-(4-alkylpiperazin-1-yl)benzoates.

Where the compound of the invention contains a carboxy group, or a sufficiently acidic bioisostere, base addition salts may be formed and are simply a more convenient form for use; and in practice, use of the salt form inherently amounts to use of the free acid form. The bases which can be used to prepare the base addition salts include preferably those which produce, when combined with the free acid, pharmaceutically acceptable salts, that is, salts whose cations are non-toxic to the patient in pharmaceutical doses of the salts, so that the beneficial inhibitory effects inherent in the free base are not vitiated by side effects ascribable to the cations. Pharmaceutically acceptable salts, including those derived from alkali and alkaline earth metal salts, within the scope of the invention include those derived from the following bases: sodium hydride, sodium hydroxide, potassium hydroxide, calcium hydroxide, aluminium hydroxide, lithium hydroxide, magnesium hydroxide, zinc hydroxide, ammonia, ethylenediamine, N-methyl-glucamine, lysine, arginine, ornithine, choline, N,N'-dibenzylethylenediamine, chloroprocaine, diethanolamine, procaine, N-benzylphenethylamine, diethylamine, piperazine, tris (hydroxymethyl)aminomethane, tetramethylammonium hydroxide, and the like.

Some of the compounds of the present invention are basic, and such compounds are useful in the form of the free base or in the form of a pharmaceutically acceptable acid addition salt thereof.

Acid addition salts are a more convenient form for use; and in practice, use of the salt form inherently amounts to use of the free base form. The acids which can be used to prepare the acid addition salts include preferably those which produce, when combined with the free base, pharmaceutically acceptable salts, that is, salts whose anions are non-toxic to the patient in pharmaceutical doses of the salts, so that the beneficial inhibitory effects inherent in the free base are not vitiated by side effects ascribable to the anions. Although pharmaceutically acceptable salts of said basic compounds are preferred, all acid addition salts are useful as sources of the free base form even if the particular salt, per se, is desired only as an intermediate product as, for example, when the salt is formed only for purposes of purification, and identification, or when it is used as intermediate in preparing a pharmaceutically acceptable salt by ion exchange procedures. Pharmaceutically acceptable salts within the scope of the invention include those derived from mineral acids and organic acids, and include hydrohalides, e.g. hydrochlorides and hydrobromides, sulphates, phosphates, nitrates, sulphamates, acetates, citrates, lactates, tartrates, malonates, oxalates, salicylates, propionates, succinates, fumarates, maleates, methylene-bis-b-hydroxynaphthoates, gentisates, isethionates, di-p-toluoyltartrates, methane-sulphonates, ethanesulphonates, benzenesulphonates, p-toluenesulphonates, cyclohexylsulphamates and quinates.

As well as being useful in themselves as active compounds, salts of compounds of the invention are useful for the purposes of purification of the compounds, for example by exploitation of the solubility differences between the salts and the parent compounds, side products and/or starting materials by techniques well known to those skilled in the art.

With reference to formula (I) above, the following are particular and preferred groupings:

$R^1$ may particularly represent optionally substituted aryl, especially optionally substituted phenyl.

$Z^1$ may particularly represent NH.

Het may particularly represent

, wherein ring

is a 5 or 6 membered heterocycle and ring

is a 5 or 6 membered fully unsaturated heterocycle or a benzene ring, each ring optionally substituted by one or more "aryl group substituents" as defined above, and the two rings are joined together by a carbon-carbon linkage or a carbon-nitrogen linkage.

Ring

may particularly represent a 5 membered fully unsaturated heterocycle.

Ring

may particularly represent a benzene ring, optionally substituted by one or more "aryl group substituents" as defined above.

may particularly represent a 9 membered bicyclic system in which rings

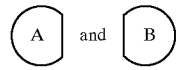

are as defined just above and the two rings are joined together by carbon atom linkages.

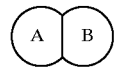

is preferably benzoxazolyl or benzimidazolyl, in which ring

is optionally substituted by one or more "aryl group substituents" as defined above [examples of particular aryl group substituents include $C_{1-4}$ alkyl (e.g. methyl or ethyl), $C_{1-4}$ alkoxy (e.g. methoxy), amino, halogen, hydroxy, $C_{1-4}$ alkylthio, $C_{1-4}$ alkylsulphinyl, $C_{1-4}$ alkylsulphonyl, nitro or trifluoromethyl].

$L^1$ may particularly represent a $-R^3-R^4$-linkage where $R^3$ represents a straight or branched $C_{1-6}$alkylene chain, especially a straight or branched $C_{1-4}$alkylene chain, and $R^4$ represents $-C(=Z^2)-NR^5-$, preferably $-C(=O)-NR^5-$, especially where $R^5$ is hydrogen or $C_{1-4}$ alkyl, more especially hydrogen.

$R^2$ may particularly represent hydrogen.

$L^2$ may particularly represent an optionally substituted alkylene linkage, especially optionally substituted ethylene. Preferred optional substituents include $C_{1-4}$ alkyl (e.g. methyl), aryl (e.g. optionally substituted phenyl), or alkyl substituted by hydroxy, —OR⁶, —O—C(=O)—R⁶ or —NY¹Y². L² is preferably a group

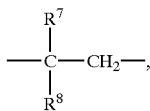

where R⁷ is hydrogen or $C_{1-4}$ alkyl (e.g. methyl) and R⁸ represents hydrogen or $C_{1-4}$ alkyl (e.g. methyl), or where R⁷ is hydrogen and R⁸ represents aryl (e.g. optionally substituted phenyl) or alkyl substituted by hydroxy, —OR⁴, —O—C(=O)—R⁶ or —NY¹Y². L² is more preferably a group

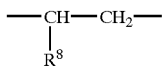

where R⁸ represents $C_{1-4}$ alkyl (e.g. methyl), aryl (e.g. optionally substituted phenyl), or alkyl substituted by hydroxy, —OR⁶, —O—C(=O)—R⁶ or —NY¹Y².

Y may particularly represent carboxy.

It is to be understood that this invention covers all appropriate combinations of the particular and preferred groupings referred to herein.

A particular group of compounds of the invention are compounds of formula (Ia):

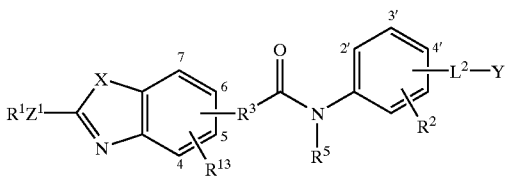

(Ia)

in which R¹, R², R³, R⁵, L², Y and Z¹ are as hereinbefore defined, R¹³ is hydrogen or an aryl group substituent and X is O or NR⁹ (in which R⁹ is hydrogen or $C_{1-4}$ alkyl), and their prodrugs and pharmaceutically acceptable salts, and solvates (e.g. hydrates) of compounds of formula (Ia) and their prodrugs.

Compounds of formula (Ia) in which R¹ represents optionally substituted aryl, especially optionally substituted phenyl, are preferred. Preferred optional substituents include $C_{1-4}$ alkyl (e.g. methyl), $C_{1-4}$ alkyl (e.g. methoxy), halo (e.g. fluoro) and Y¹Y²N— (e.g. dimethylamino). R¹ especially represents ortho-tolyl.

Compounds of formula (Ia) in which Z¹ represents NH are preferred.

Compounds of formula (Ia) in which R¹³ represents hydrogen, $C_{1-4}$ alkyl (e.g. methyl or ethyl) or $C_{1-4}$ alkoxy (e.g. methoxy) are preferred.

Compounds of formula (Ia) in which R³ represents a straight or branched $C_{1-6}$alkylene chain, especially a straight or branched $C_{1-4}$alkylene chain, more especially methylene, are preferred.

Compounds of formula (Ia) in which R⁵ represents hydrogen are preferred.

Compounds of formula (Ia) in which R² represents hydrogen are preferred.

Compounds of formula (Ia) in which L² represents an optionally substituted alkylene linkage, especially ethylene or substituted ethylene, are preferred. Preferred optional substituents include $C_{1-4}$ alkyl (e.g. methyl), aryl (e.g. optionally substituted phenyl) or alkyl substituted by hydroxy, —OR⁶, —O—C(=O)—R⁶ or —NY¹Y². Compounds of formula (Ia) in which L² is a

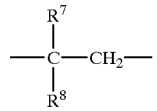

linkage, where
R⁷ is hydrogen or $C_{1-4}$ alkyl (e.g. methyl) and R⁸ represents hydrogen or $C_{1-4}$ alkyl (e.g. methyl), or where R⁷ is hydrogen and R⁸ represents aryl (e.g. optionally substituted phenyl) or alkyl substituted by hydroxy, —OR⁶, —O—C(=O)—R⁶ or —NY¹Y² are particularly preferred. Compounds of formula (Ia) in which L² is a

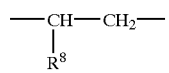

linkage, where R⁸ represents $C_{1-4}$ alkyl (e.g. methyl), aryl (e.g. optionally substituted phenyl), or alkyl substituted hydroxy, —OR⁶, —O—C(=O)—R⁶ or —NY¹Y², are especially preferred.

Compounds of formula (Ia) in which Y represents carboxy are preferred.

The group

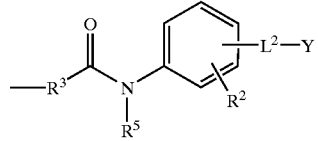

may preferably be attached at the ring 6 position when X is O or NH, or at the ring 5 or 6 position when X is NR⁹ and R⁹ is $C_{1-4}$ alkyl.

The group —L²—Y may preferably be attached at the 4' position of the phenyl ring.

A preferred group of compounds of the invention are compounds of formula (Ia) in which: R¹ is optionally substituted phenyl (especially $C_{1-4}$ alkyl substituted phenyl, more especially ortho-tolyl); Z¹ is NH; X is O; R¹³ represents hydrogen, $C_{1-4}$ alkyl (e.g. methyl or ethyl) or $C_{1-4}$alkoxy (e.g. methoxy); R³ is a straight or branched $C_{1-4}$alkylene chain, (especially methylene); R⁵ is hydrogen; R² is hydrogen; L² is a

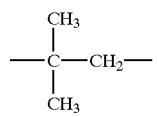

group or preferably a

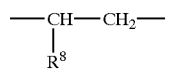

group, where R⁸ represents hydrogen, $C_{1-4}$ alkyl (especially methyl), aryl (e.g. optionally substituted phenyl) or alkyl substituted by hydroxy, —OR⁶, —O—C(=O)—R⁶ or —NY¹Y²; Y is carboxy; the group

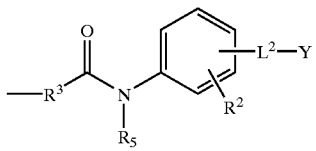

is attached at the ring 6 position; and the group —L²—Y is attached at the 4' position of the phenyl ring; and the corresponding N-oxides, and their prodrugs; and pharmaceutically acceptable salts and solvates (e.g. hydrates) of such compounds and their N-oxides and prodrugs.

Another preferred group of compounds of the invention are compounds of formula (Ia) in which: $R^1$ is optionally substituted phenyl (especially $C_{1-4}$ alkyl substituted phenyl, more especially ortho-tolyl);

$Z^1$ is NH; X is $NR^9$ (especially NH); $R^{13}$ represents hydrogen, $C_{1-4}$ alkyl (e.g. methyl or ethyl) or $C_{1-4}$ alkoxy (e.g. methoxy); $R^3$ is a straight or branched $C_{1-4}$ alkylene chain, (especially methylene);

$R^5$ is hydrogen; $R^2$ is hydrogen; $L^2$ is a

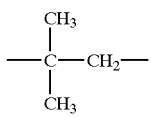

group or preferably a

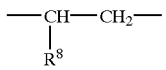

group, where $R^8$ represents hydrogen, $C_{1-4}$ alkyl (especially methyl), aryl (e.g. optionally substituted phenyl) or alkyl substituted by hydroxy, —OR⁶, —O—C(=O)—R⁶ or —NY¹Y²; Y is carboxy; the group

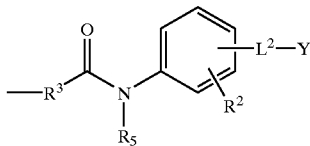

is attached at the ring 5 or 6 position; and the group —L²—Y is attached at the 4' position of the phenyl ring; and the corresponding N-oxides, and their prodrugs; and pharmaceutically acceptable salts and solvates (e.g. hydrates) of such compounds and their N-oxides and prodrugs.

Particular compounds of the invention are selected from the compounds formed by joining the acyl carbon atom (C*) of one of the fragments (A1 to A36) shown in Table 1 to the nitrogen atom (N*) of one of the fragments (B1 to B4) shown in Table 2, and joining the carbon atom (C*) of the phenyl ring in one of the fragments (B1 to B4) shown in Table 2 to the carbon atom (C*) of one of the acidic fragments (C1 to C27) depicted in Table 3.

TABLE 1

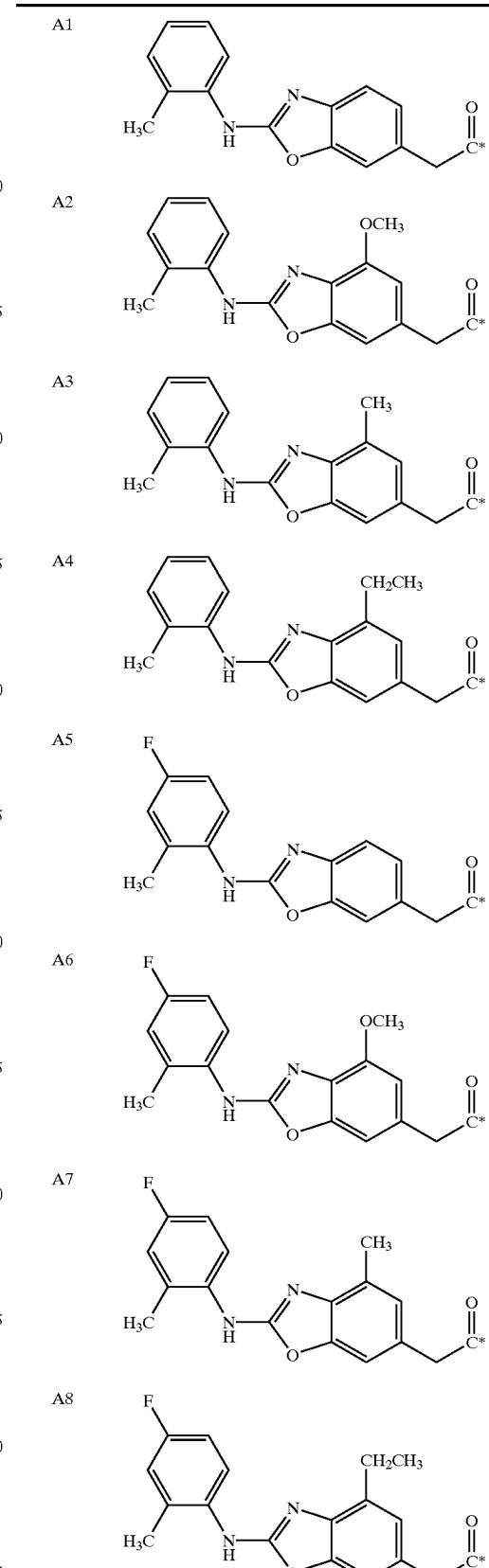

TABLE 1-continued
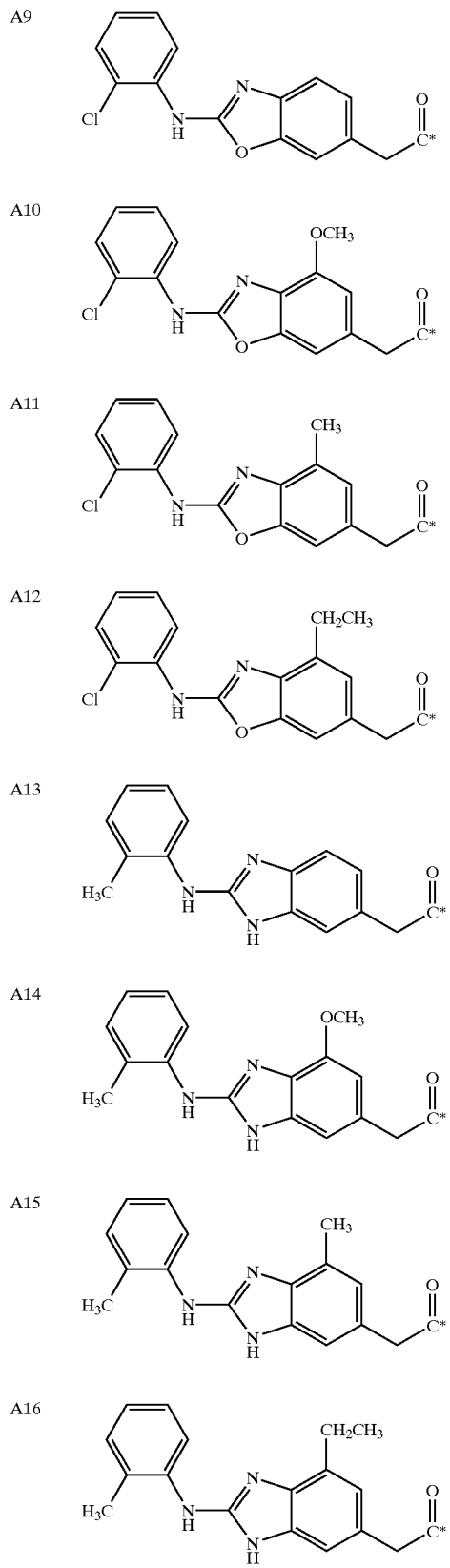
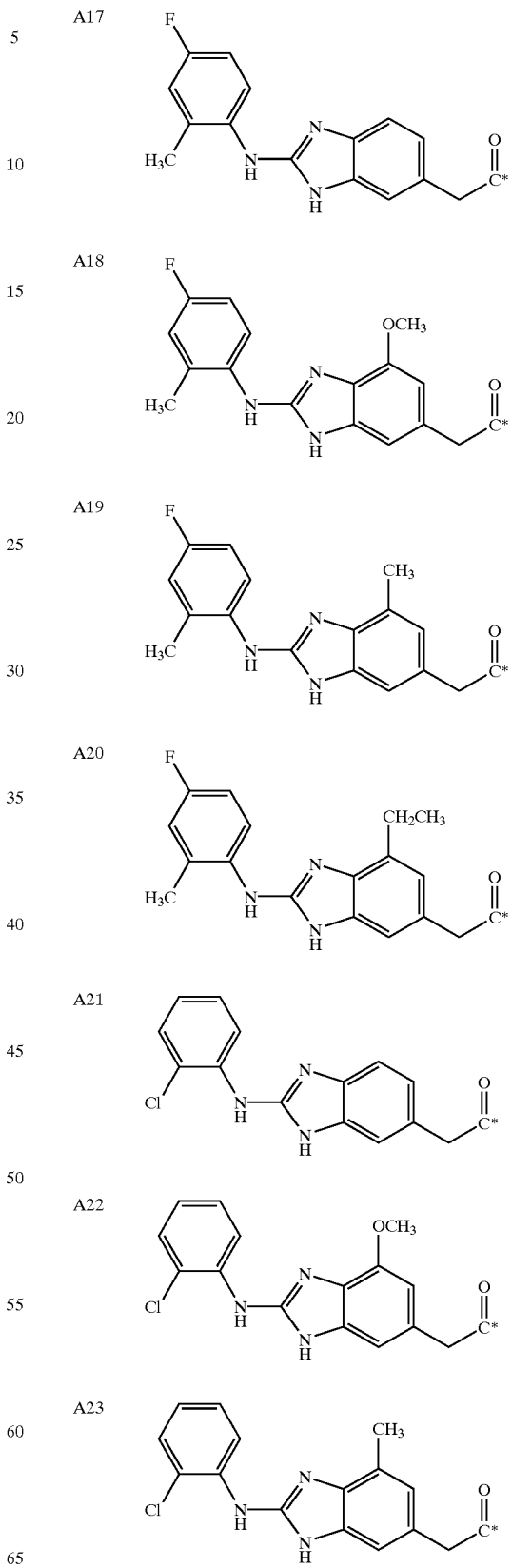

TABLE 1-continued
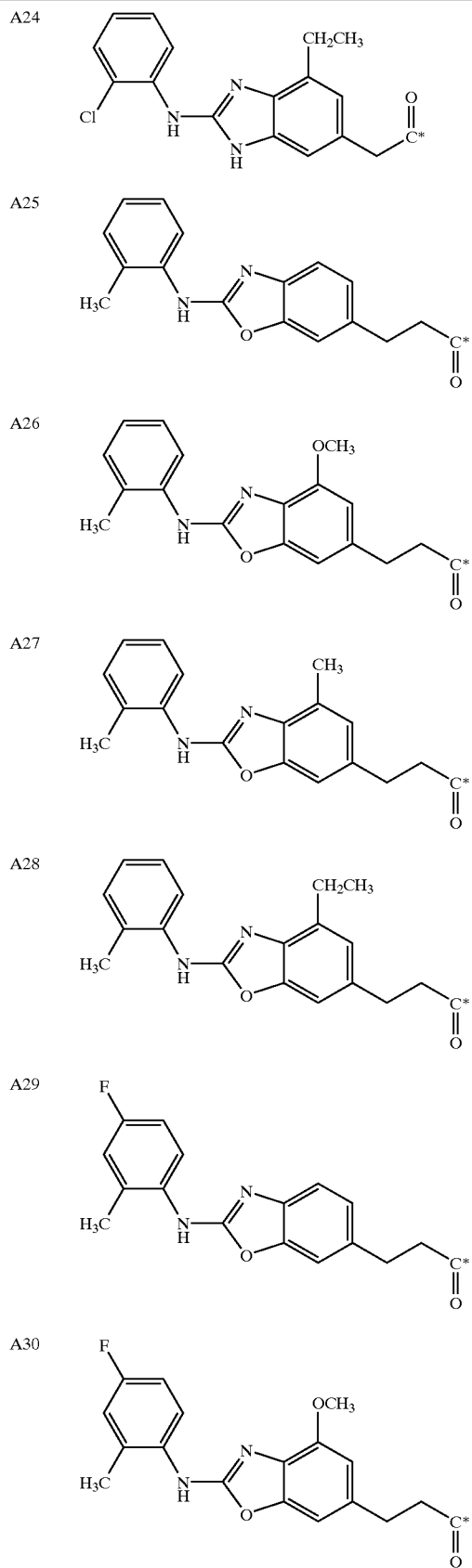
TABLE 1-continued
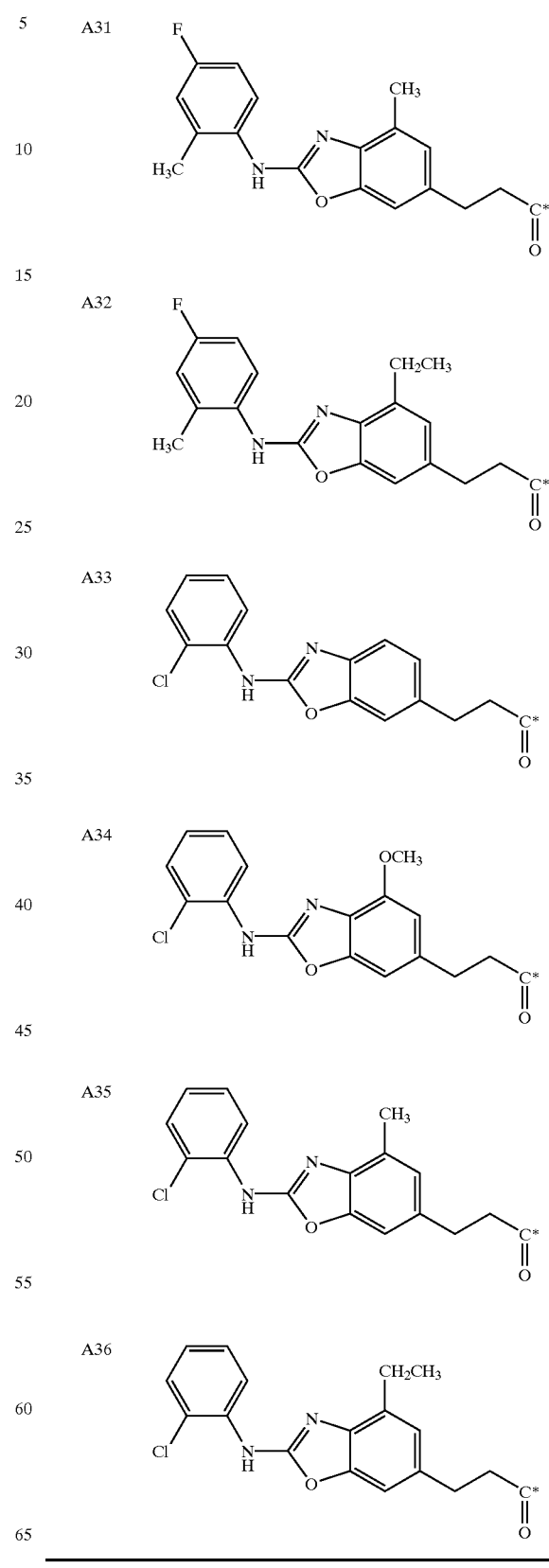

TABLE 2

- B1: 4-aminophenyl (*N H, C* para) — aniline with *N-H and *C on para position
- B2: 4-(methylamino)phenyl — *N-CH3, *C para
- B3: 3-aminophenyl — *N-H, *C meta
- B4: 3-(methylamino)phenyl — *N-CH3, *C meta

TABLE 3

| Code | Structure |
|---|---|
| C1 | *CH$_2$—CH$_2$—CO$_2$H |
| C2 | *CH$_2$—CH$_2$—CH$_2$—CO$_2$H |
| C3 | *CH(CH$_3$)—CH$_2$—CO$_2$H |
| C4 | *CH(CH$_2$CH$_3$)—CH$_2$—CO$_2$H |
| C5 | *CH(CH(CH$_3$)$_2$)—CH$_2$—CO$_2$H |
| C6 | *CH(CH$_2$CH(CH$_3$)$_2$)—CH$_2$—CO$_2$H |
| C7 | *CH(C(CH$_3$)$_3$)—CH$_2$—CO$_2$H |
| C8 | *CH(CH$_2$C(CH$_3$)$_3$)—CH$_2$—CO$_2$H |
| C9 | *CH(phenyl)—CH$_2$—CO$_2$H |
| C10 | *CH(4-fluorophenyl)—CH$_2$—CO$_2$H |
| C11 | *CH(2-methylphenyl)—CH$_2$—CO$_2$H |
| C12 | *CH(pyridin-2-yl)—CH$_2$—CO$_2$H |
| C13 | *CH(pyridin-3-yl)—CH$_2$—CO$_2$H |
| C14 | *CH(pyridin-4-yl)—CH$_2$—CO$_2$H |
| C15 | *CH(furan-2-yl)—CH$_2$—CO$_2$H |
| C16 | *CH(furan-3-yl)—CH$_2$—CO$_2$H |
| C17 | *CH(thiophen-2-yl)—CH$_2$—CO$_2$H |
| C18 | *CH(thiophen-3-yl)—CH$_2$—CO$_2$H |
| C19 | *CH(3-methylthiophen-2-yl)—CH$_2$—CO$_2$H |
| C20 | *CH(2-methylthiophen-3-yl)—CH$_2$—CO$_2$H |
| C21 | *CH(4-methylthiophen-3-yl)—CH$_2$—CO$_2$H |

TABLE 3-continued

| | | |
|---|---|---|
| C22 | *CH—CH$_2$—CO$_2$H | |
| C23 | *CH—CH$_2$—CO$_2$H | |
| C24 | *CH—CH$_2$—CO$_2$H | |

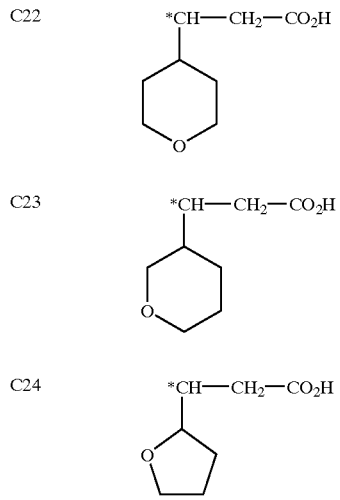

TABLE 3-continued

| | | |
|---|---|---|
| C25 | *CH—CH$_2$—CO$_2$H | |
| C26 | *CH—CH$_2$—CO$_2$H<br>\|<br>CH$_2$CO$_2$H | |
| C27 | *CH—CH$_2$—CO$_2$H<br>\|<br>CH$_2$CH$_2$CH$_2$OH | |

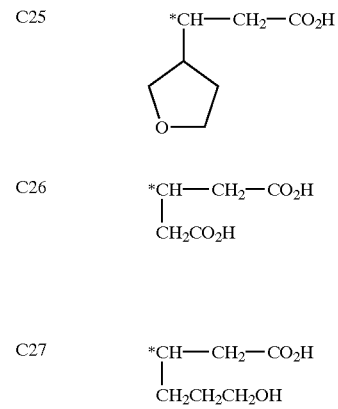

Particularly preferred examples of fragments "A", "B", and "C" are illustrated below:

| | | | | | |
|---|---|---|---|---|---|
| A1-B1-C1; | A1-B1-C2; | A1-B1-C3; | A1-B1-C4; | A1-B1-C5; | A1-B1-C6; |
| A1-B1-C7; | A1-B1-C8; | A1-B1-C9; | A1-B1-C10; | A1-B1-C11; | A1-B1-C12; |
| A1-B1-C13; | A1-B1-C14; | A1-B1-C15; | A1-B1-C16; | A1-B1-C17; | A1-B1-C18; |
| A1-B1-C19; | A1-B1-C20; | A1-B1-C21; | A1-B1-C22; | A1-B1-C23; | A1-B1-C24; |
| A1-B1-C25; | A1-B1-C26; | A1-B1-C27; | A2-B1-C1; | A2-B1-C2; | A2-B1-C3; |
| A2-B1-C4; | A2-B1-C5; | A2-B1-C6; | A2-B1-C7; | A2-B1-C8; | A2-B1-C9; |
| A2-B1-C10; | A2-B1-C11; | A2-B1-C12; | A2-B1-C13; | A2-B1-C14; | A2-B1-C15; |
| A2-B1-C16; | A2-B1-C17; | A2-B1-C18; | A2-B1-C19; | A2-B1-C20; | A2-B1-C21; |
| A2-B1-C22; | A2-B1-C23; | A2-B1-C24; | A2-B1-C25; | A2-B1-C26; | A2-B1-C27; |
| A3-B1-C1; | A3-B1-C2; | A3-B1-C3; | A3-B1-C4; | A3-B1-C5; | A3-B1-C6; |
| A3-B1-C7; | A3-B1-C8; | A3-B1-C9; | A3-B1-C10; | A3-B1-C11; | A3-B1-C12; |
| A3-B1-C13; | A3-B1-C14; | A3-B1-C15; | A3-B1-C16; | A3-B1-C17; | A3-B1-C18; |
| A3-B1-C19; | A3-B1-C20; | A3-B1-C21; | A3-B1-C22; | A3-B1-C23; | A3-B1-C24; |
| A3-B1-C25; | A3-B1-C26; | A3-B1-C27; | A4-B1-C1; | A4-B1-C2; | A4-B1-C3; |
| A4-B1-C4; | A4-B1-C5; | A4-B1-C6; | A4-B1-C7; | A4-B1-C8; | A4-B1-C9; |
| A4-B1-C10; | A4-B1-C11; | A4-B1-C12; | A4-B1-C13; | A4-B1-C14; | A4-B1-C15; |
| A4-B1-C16; | A4-B1-C17; | A4-B1-C18; | A4-B1-C19; | A4-B1-C20; | A4-B1-C21; |
| A4-B1-C22; | A4-B1-C23; | A4-B1-C24; | A4-B1-C25; | A4-B1-C26; | A4-B1-C27; |
| A5-B1-C1; | A5-B1-C2; | A5-B1-C3; | A5-B1-C4; | A5-B1-C5; | A5-B1-C6; |
| A5-B1-C7; | A5-B1-C8; | A5-B1-C9; | A5-B1-C10; | A5-B1-C11; | A5-B1-C12; |
| A5-B1-C13; | A5-B1-C14; | A5-B1-C15; | A5-B1-C16; | A5-B1-C17; | A5-B1-C18; |
| A5-B1-C19; | A5-B1-C20; | A5-B1-C21; | A5-B1-C22; | A5-B1-C23; | A5-B1-C24; |
| A5-B1-C25; | A5-B1-C26; | A5-B1-C27; | A6-B1-C1; | A6-B1-C2; | A6-B1-C3; |
| A6-B1-C4; | A6-B1-C5; | A6-B1-C6; | A6-B1-C7; | A6-B1-C8; | A6-B1-C9; |
| A6-B1-C10; | A6-B1-C11; | A6-B1-C12; | A6-B1-C13; | A6-B1-C14; | A6-B1-C15; |
| A6-B1-C16; | A6-B1-C17; | A6-B1-C18; | A6-B1-C19; | A6-B1-C20; | A6-B1-C21; |
| A6-B1-C22; | A6-B1-C23; | A6-B1-C24; | A6-B1-C25; | A5-B1-C26; | A5-B1-C27; |
| A7-B1-C1; | A7-B1-C2; | A7-B1-C3; | A7-B1-C4; | A7-B1-C5; | A7-B1-C6; |
| A7-B1-C7; | A7-B1-C8; | A7-B1-C9; | A7-B1-C10; | A7-B1-C11; | A7-B1-C12; |
| A7-B1-C13; | A7-B1-C14; | A7-B1-C15; | A7-B1-C16; | A7-B1-C17; | A7-B1-C18; |
| A7-B1-C19; | A7-B1-C20; | A7-B1-C21; | A7-B1-C22; | A7-B1-C23; | A7-B1-C24; |
| A7-B1-C25; | A7-B1-C26; | A7-B1-C27; | A8-B1-C1; | A8-B1-C2; | A5-B1-C3; |
| A8-B1-C4; | A8-B1-C5; | A5-B1-C6; | A5-B1-C7; | A5-B1-C8; | A8-B1-C9; |
| A5-B1-C10; | A5-B1-C11; | A8-B1-C12; | A8-B1-C13; | A5-B1-C14; | A5-B1-C15; |
| A8-B1-C16; | A8-B1-C17; | A8-B1-C18; | A8-B1-C19; | A8-B1-C20; | A8-B1-C21; |
| A8-B1-C22; | A8-B1-C23; | A8-B1-C24; | A8-B1-C25; | A8-B1-C26; | A8-B1-C27; |
| A9-B1-C1; | A9-B1-C2; | A9-B1-C3; | A9-B1-C4; | A9-B1-C5; | A9-B1-C6; |
| A9-B1-C7; | A9-B1-C8; | A9-B1-C9; | A9-B1-C10; | A9-B1-C11; | A9-B1-C12; |
| A9-B1-C13; | A9-B1-C14; | A9-B1-C15; | A9-B1-C16; | A9-B1-C17; | A9-B1-C18; |
| A9-B1-C19; | A9-B1-C20; | A9-B1-C21; | A9-B1-C22; | A9-B1-C23; | A9-B1-C24; |
| A9-B1-C25; | A9-B1-C26; | A9-B1-C27; | A10-B1-C1; | A10-B1-C2; | A10-B1-C3; |
| A10-B1-C4; | A10-B1-C5; | A10-B1-C6; | A10-B1-C7; | A10-B1-C8; | A10-B1-C9; |
| A10-B1-C10; | A10-B1-C11; | A10-B1-C12; | A10-B1-C13; | A10-B1-C14; | A10-B1-C15; |
| A10-B1-C16; | A10-B1-C17; | A10-B1-C18; | A10-B1-C19; | A10-B1-C20; | A10-B1-C21; |
| A10-B1-C22; | A10-B1-C23; | A10-B1-C24; | A10-B1-C25; | A10-B1-C26; | A10-B1-C27; |
| A11-B1-C1; | A11-B1-C2 | A11-B1-C3; | A11-B1-C4; | A11-B1-C5; | A11-B1-C6; |
| A11-B1-C7; | A11-B1-C8; | A11-B1-C9; | A11-B1-C10; | A11-B1-C11; | A11-B1-C12; |
| A11-B1-C13; | A11-B1-C14; | A11-B1-C15; | A11-B1-C16; | A11-B1-C17; | A11-B1-C18; |

-continued

| | | | | | |
|---|---|---|---|---|---|
| A11-B1-C19; | A11-B1-C20; | A11-B1-C21; | A11-B1-C22; | A11-B1-C23; | A11-B1-C24; |
| A11-B1-C25; | A11-B1-C26; | A11-B1-C27; | A12-B1-C1; | A12-B1-C2; | A12-B1-C3; |
| A12-B1-C4; | A12-B1-C5; | A12-B1-C6; | A12-B1-C7; | A12-B1-C8; | A12-B1-C9; |
| A12-B1-C10; | A12-B1-C11; | A12-B1-C12; | A12-B1-C13; | A12-B1-C14; | A12-B1-C15; |
| A12-B1-C16; | A12-B1-C17; | A12-B1-C18; | A12-B1-C19; | A12-B1-C20; | A12-B1-C21; |
| A12-B1-C22; | A12-B1-C23; | A12-B1-C24; | A12-B1-C25; | A12-B1-C26; | A12-B1-C27; |
| A13-B1-C1; | A13-B1-C2; | A13-B1-C3; | A13-B1-C4; | A13-B1-C5; | A13-B1-C6; |
| A13-B1-C7; | A13-B1-C8; | A13-B1-C9; | A13-B1-C10; | A13-B1-C11; | A13-B1-C12; |
| A13-B1-C13; | A13-B1-C14; | A13-B1-C15; | A13-B1-C16; | A13-B1-C17; | A13-B1-C18; |
| A13-B1-C19; | A13-B1-C20; | A13-B1-C21; | A13-B1-C22; | A13-B1-C23; | A13-B1-C24; |
| A13-B1-C25; | A13-B1-C26; | A13-B1-C27; | A14-B1-C1; | A14-B1-C2; | A14-B1-C3; |
| A14-B1-C4; | A14-B1-C5; | A14-B1-C6; | A14-B1-C7; | A14-B1-C8; | A14-B1-C9; |
| A14-B1-C10; | A14-B1-C11; | A14-B1-C12; | A14-B1-C13; | A14-B1-C14; | A14-B1-C15; |
| A14-B1-C16; | A14-B1-C17; | A14-B1-C18; | A14-B1-C19; | A14-B1-C20; | A14-B1-C21; |
| A14-B1-C22; | A14-B1-C23; | A14-B1-C24; | A14-B1-C25; | A14-B1-C26; | A14-B1-C27; |
| A15-B1-C1; | A15-B1-C2; | A15-B1-C3; | A15-B1-C4; | A15-B1-C5; | A15-B1-C6; |
| A15-B1-C7; | A15-B1-C8; | A15-B1-C9; | A15-B1-C10; | A15-B1-C11; | A15-B1-C12; |
| A15-B1-C13; | A15-B1-C14; | A15-B1-C15; | A15-B1-C16; | A15-B1-C17; | A15-B1-C18; |
| A15-B1-C19; | A15-B1-C20; | A15-B1-C21; | A15-B1-C22; | A15-B1-C23; | A15-B1-C24; |
| A15-B1-C25; | A15-B1-C26; | A15-B1-C27; | A16-B1-C1; | A16-B1-C2; | A16-B1-C3; |
| A16-B1-C4; | A16-B1-C5; | A16-B1-C6; | A16-B1-C7; | A16-B1-C8; | A16-B1-C9; |
| A16-B1-C10; | A16-B1-C11; | A16-B1-C12; | A16-B1-C13; | A16-B1-C14; | A16-B1-C15; |
| A16-B1-C16; | A16-B1-C17; | A16-B1-C18; | A16-B1-C19; | A16-B1-C20; | A16-B1-C21; |
| A16-B1-C22; | A16-B1-C23; | A16-B1-C24; | A16-B1-C25; | A16-B1-C26; | A16-B1-C27; |
| A17-B1-C1; | A17-B1-C2; | A17-B1-C3; | A17-B1-C4; | A17-B1-C5; | A17-B1-C6; |
| A17-B1-C7; | A17-B1-C8; | A17-B1-C9; | A17-B1-C10; | A17-B1-C11; | A17-B1-C12; |
| A17-B1-C13; | A17-B1-C14; | A17-B1-C15; | A17-B1-C16; | A17-B1-C17; | A17-B1-C18; |
| A17-B1-C19; | A17-B1-C20; | A17-B1-C21; | A17-B1-C22; | A17-B1-C23; | A17-B1-C24; |
| A17-B1-C25; | A17-B1-C26; | A17-B1-C27; | A18-B1-C1; | A18-B1-C2; | A18-B1-C3; |
| A18-B1-C4; | A18-B1-C5; | A18-B1-C6; | A18-B1-C7; | A18-B1-C8; | A18-B1-C9; |
| A18-B1-C10; | A18-B1-C11; | A18-B1-C12; | A15-B1-C13; | A18-B1-C14; | A18-B1-C15; |
| A18-B1-C16; | A18-B1-C17; | A18-B1-C18; | A18-B1-C19; | A18-B1-C20; | A18-B1-C21; |
| A18-B1-C22; | A18-B1-C23; | A18-B1-C24; | A18-B1-C25; | A18-B1-C26; | A18-B1-C27; |
| A19-B1-C1; | A19-B1-C2; | A19-B1-C3; | A19-B1-C4; | A19-B1-C5; | A19-B1-C6; |
| A19-B1-C7; | A19-B1-C8; | A19-B1-C9; | A19-B1-C10; | A19-B1-C11; | A19-B1-C12; |
| A19-B1-C13; | A19-B1-C14; | A19-B1-C15; | A19-B1-C16; | A19-B1-C17; | A19-B1-C18; |
| A19-B1-C19; | A19-B1-C20; | A19-B1-C21; | A19-B1-C22; | A19-B1-C23; | A19-B1-C24; |
| A19-B1-C25; | A19-B1-C26; | A19-B1-C27; | A20-B1-C1; | A20-B1-C2; | A20-B1-C3; |
| A20-B1-C4; | A20-B1-C5; | A20-B1-C6; | A20-B1-C7; | A20-B1-C8; | A20-B1-C9; |
| A20-B1-C10; | A20-B1-C11; | A20-B1-C12; | A20-B1-C13; | A20-B1-C14; | A20-B1-C15; |
| A20-B1-C16; | A20-B1-C17; | A20-B1-C18; | A20-B1-C19; | A20-B1-C20; | A20-B1-C21; |
| A20-B1-C22; | A20-B1-C23; | A20-B1-C24; | A20-B1-C25; | A20-B1-C26; | A20-B1-C27; |
| A21-B1-C1; | A21-B1-C2; | A21-B1-C3; | A21-B1-C4; | A21-B1-C5; | A21-B1-C6; |
| A21-B1-C7; | A21-B1-C8; | A21-B1-C9; | A21-B1-C10; | A21-B1-C11; | A21-B1-C12; |
| A21-B1-C13; | A21-B1-C14; | A21-B1-C15; | A21-B1-C16; | A21-B1-C17; | A21-B1-C18; |
| A21-B1-C19; | A21-B1-C20; | A21-B1-C21; | A21-B1-C22; | A21-B1-C23; | A21-B1-C24; |
| A21-B1-C25; | A21-B1-C26; | A21-B1-C27; | A22-B1-C1; | A22-B1-C2; | A22-B1-C3; |
| A22-B1-C4; | A22-B1-C5; | A22-B1-C6; | A22-B1 C7; | A22-B1-C8; | A22-B1-C9; |
| A22-B1-C10; | A22-B1-C11; | A22-B1-C12; | A22-B1-C13; | A22-B1-C14; | A22-B1-C15; |
| A22-B1-C16; | A22-B1-C17; | A22-B1-C18; | A22-B1-C19; | A22-B1-C20; | A22-B1-C21; |
| A22-B1-C22; | A22-B1-C23; | A22-B1-C24; | A22-B1-C25; | A22-B1-C26; | A22-B1-C27; |
| A23-B1-C1; | A23-B1-C2; | A23-B1-C3; | A23-B1-C4; | A23-B1-C5; | A23-B1-C6; |
| A23-B1-C7; | A23-B1-C8; | A23-B1-C9; | A23-B1-C10; | A23-B1-C11; | A23-B1-C12; |
| A23-B1-C13; | A23-B1-C14; | A23-B1-C15; | A23-B1-C16; | A23-B1-C17; | A23-B1-C18; |
| A23-B1-C19; | A23-B1-C20; | A23-B1-C21; | A23-B1-C22; | A23-B1-C23; | A23-B1-C24; |
| A23-B1-C25; | A23-B1-C26; | A23-B1-C27; | A24-B1-C1; | A24-B1-C2; | A24-B1-C3; |
| A24-B1-C4; | A24-B1-C5; | A24-B1-C6; | A24-B1-C7; | A24-B1-C8; | A24-B1-C9; |
| A24-B1-C10; | A24-B1-C11; | A24-B1-C12; | A24-B1-C13; | A24-B1-C14; | A24-B1-C15; |
| A24-B1-C16; | A24-B1-C17; | A24-B1-C18; | A24-B1-C19; | A24-B1-C20; | A24-B1-C21; |
| A24-B1-C22; | A24-B1-C23; | A24-B1-C24; | A24-B1-C25; | A24-B1-C26; | A24-B1-C27; |
| A25-B1-C1; | A25-B1-C2; | A25-B1-C3; | A25-B1-C4; | A25-B1-C5; | A25-B1-C6; |
| A25-B1-C7; | A25-B1-C8; | A25-B1-C9; | A25-B1-C10; | A25-B1-C11; | A25-B1-C12; |
| A25-B1-C13; | A25-B1-C14; | A25-B1-C15; | A25-B1-C16; | A25-B1-C17; | A25-B1-C15; |
| A25-B1-C19; | A25-B1-C20; | A25-B1-C21; | A25-B1-C22; | A25-B1-C23; | A25-B1-C24; |
| A25-B1-C25; | A25-B1-C26; | A25-B1-C27; | A26-B1-C1; | A26-B1-C2; | A26-B1-C3; |
| A26-B1-C4; | A26-B1-C5; | A26-B1-C6; | A26-B1-C7; | A26-B1-C8; | A26-B1-C9; |
| A26-B1-C10; | A26-B1-C11; | A26-B1-C12; | A26-B1-C13; | A26-B1-C14; | A26-B1-C15; |
| A26-B1-C16; | A26-B1-C17; | A26-B1-C18; | A26-B1-C19; | A26-B1-C20; | A26-B1-C21; |
| A26-B1-C22; | A26-B1-C23; | A26-B1-C24; | A26-B1-C25; | A26-B1-C26; | A26-B1-C27; |
| A27-B1-C1; | A27-B1-C2; | A27-B1-C3; | A27-B1-C4; | A27-B1-C5; | A27-B1-C6; |
| A27-B1-C7; | A27-B1-C8; | A27-B1-C9; | A27-B1-C10; | A27-B1-C11; | A27-B1-C12; |
| A27-B1-C13; | A27-B1-C14; | A27-B1-C15; | A27-B1-C16; | A27-B1-C17; | A27-B1-C18; |
| A27-B1-C19; | A27-B1-C20; | A27-B1-C21; | A27-B1-C22; | A27-B1-C23; | A27-B1-C24; |
| A27-B1-C25; | A27-B1-C26; | A27-B1-C27; | A28-B1-C1; | A28-B1-C2; | A28-B1-C3; |
| A28-B1-C4; | A28-B1-C5; | A28-B1-C6; | A28-B1-C7; | A28-B1-C5; | A28-B1-C9; |
| A28-B1-C10; | A28-B1-C11; | A28-B1-C12; | A28-B1-C13; | A28-B1-C14; | A28-B1-C15; |
| A28-B1-C16; | A28-B1-C17; | A28-B1-C18; | A28-B1-C19; | A28-B1-C20; | A28-B1-C21; |
| A28-B1-C22; | A28-B1-C23; | A28-B1-C24; | A28-B1-C25; | A28-B1-C26; | A28-B1-C27; |
| A29-B1-C1; | A29-B1-C2; | A29-B1-C3; | A29-B1-C4; | A29-B1-C5; | A29-B1-C6; |

-continued

| | | | | | |
|---|---|---|---|---|---|
| A29-B1-C7; | A29-B1-C8; | A29-B1-C9; | A29-B1-C10; | A29-B1-C11; | A29-B1-C12; |
| A29-B1-C13; | A29-B1-C14; | A29-B1-C15; | A29-B1-C16; | A29-B1-C17; | A29-B1-C18; |
| A29-B1-C19; | A29-B1-C20; | A29-B1-C21; | A29-B1-C22; | A29-B1-C23; | A29-B1-C24; |
| A29-B1-C25; | A29-B1-C26; | A29-B1-C27; | A30-B1-C1; | A30-B1-C2; | A30-B1-C3; |
| A30-B1-C4; | A30-B1-C5; | A30-B1-C6; | A30-B1-C7; | A30-B1-C8 | A30-B1-C9; |
| A30-B1-C10; | A30-B1-C11; | A30-B1-C12; | A30-B1-C13; | A30-B1-C14; | A30-B1-C15; |
| A30-B1-C16; | A30-B1-C17; | A30-B1-C18; | A30-B1-C19; | A30-B1-C20; | A30-B1-C21; |
| A30-B1-C22; | A30-B1-C23; | A30-B1-C24; | A30-B1-C25; | A30-B1-C26; | A30-B1-C27; |
| A31-B1-C1; | A31-B1-C2; | A31-B1-C3; | A31-B1-C4; | A31-B1-C5; | A31-B1-C6; |
| A31-B1-C7; | A31-B1-C8; | A31-B1-C9; | A31-B1-C10; | A31-B1-C11; | A31-B1-C12; |
| A31-B1-C13; | A31-B1-C14; | A31-B1-C15; | A31-B1-C16; | A31-B1-C17; | A31-B1-C18; |
| A31-B1-C19; | A31-B1-C20; | A31-B1-C21; | A31-B1-C22; | A31-B1-C23; | A31-B1-C24; |
| A31-B1-C25; | A31-B1-C26; | A31-B1-C27; | A32-B1-C1; | A32-B1-C2; | A32-B1-C3; |
| A32-B1-C4; | A32-B1-C5; | A32-B1-C6; | A32-B1-C7; | A32-B1-C8; | A32-B1-C9; |
| A32-B1-C10; | A32-B1-C11; | A32-B1-C12; | A32-B1-C13; | A32-B1-C14; | A32-B1-C15; |
| A32-B1-C16; | A32-B1-C17; | A32-B1-C18; | A32-B1-C19; | A32-B1-C20; | A32-B1-C21; |
| A32-B1-C22; | A32-B1-C23; | A32-B1-C24; | A32-B1-C25; | A32-B1-C26; | A32-B1-C27; |
| A33-B1-C1; | A33-B1-C2; | A33-B1-C3; | A33-B1-C4; | A33-B1-C5; | A33-B1-C6; |
| A33-B1-C7; | A33-B1-C8; | A33-B1-C9; | A33-B1-C10; | A33-B1-C11; | A33-B1-C12; |
| A33-B1-C13; | A33-B1-C14; | A33-B1-C15; | A33-B1-C16; | A33-B1-C17; | A33-B1-C18; |
| A33-B1-C19; | A33-B1-C20; | A33-B1-C21; | A33-B1-C22; | A33-B1-C23; | A33-B1-C24; |
| A33-B1-C25; | A33-B1-C26; | A33-B1-C27; | A34-B1-C1; | A34-B1-C2; | A34-B1-C3; |
| A34-B1-C4; | A34-B1-C5; | A34-B1-C6; | A34-B1-C7; | A34-B1-C8; | A34-B1-C9 |
| A34-B1-C10; | A34-B1-C11; | A34-B1-C12; | A34-B1-C13; | A34-B1-C14; | A34-B1-C15; |
| A34-B1-C16; | A34-B1-C17; | A34-B1-C18; | A34-B1-C19; | A34-B1-C20; | A34-B1-C21; |
| A34-B1-C22; | A34-B1-C23; | A34-B1-C24; | A34-B1-C25; | A34-B1-C26; | A34-B1-C27; |
| A35-B1-C1; | A35-B1-C2; | A35-B1-C3; | A35-B1-C4; | A35-B1-C5; | A35-B1-C6; |
| A35-B1-C7; | A35-B1-C8; | A35-B1-C9; | A35-B1-C10; | A35-B1-C11; | A35-B1-C12; |
| A35-B1-C13; | A35-B1-C14; | A35-B1-C15; | A35-B1-C16; | A35-B1-C17; | A35-B1-C18; |
| A35-B1-C19; | A35-B1-C20; | A35-B1-C21; | A35-B1-C22; | A35-B1-C23; | A35-B1-C24; |
| A35-B1-C25; | A35-B1-C26; | A35-B1-C27; | A36-B1-C1; | A36-B1-C2; | A36-B1-C3; |
| A36-B1-C4; | A36-B1-C5; | A36-B1-C6; | A36-B1-C7; | A36-B1-C8; | A36-B1-C9; |
| A36-B1-C10; | A36-B1-C11; | A36-B1-C12; | A36-B1-C13; | A36-B1-C14; | A36-B1-C15; |
| A36-B1-C16; | A36-B1-C17; | A36-B1-C18; | A36-B1-C19; | A36-B1-C20; | A36-B1-C21; |
| A36-B1-C22; | A36-B1-C23; | A36-B1-C24; | A36-B1-C25; | A36-B1-C26; | A36-B1-C27; |
| A1-B2-C1; | A1-B2-C2; | A1-B2-C3; | A1-B2-C4; | A1-B2-C5; | A1-B2-C6; |
| A1-B2-C7; | A1-B2-C8; | A1-B2-C9; | A1-B2-C10; | A1-B2-C11; | A1-B2-C12; |
| A1-B2-C13; | A1-B2-C14; | A1-B2-C15; | A1-B2-C16; | A1-B2-C17; | A1-B2-C18; |
| A1-B2-C19; | A1-B2-C20; | A1-B2-C21; | A1-B2-C22; | A1-B2-C23; | A1-B2-C24; |
| A1-B2-C25; | A1-B2-C26; | A1-B2-C27; | A2-B2-C1; | A2-B2-C2; | A2-B2-C3; |
| A2-B2-C4; | A2-B2-C5; | A2-B2-C6; | A2-B2-C7 | A2-B2-C8; | A2-B2-C9; |
| A2-B2-C10; | A2-B2-C11; | A2-B2-C12; | A2-B2-C13; | A2-B2-C14; | A2-B2-C15; |
| A2-B2-C16; | A2-B2-C17; | A2-B2-C18; | A2-B2-C19; | A2-B2-C20; | A2-B2-C21; |
| A2-B2-C22; | A2-B2-C23; | A2-B2-C24; | A2-B2-C25; | A2-B2-C26; | A2-B2-C27; |
| A3-B2-C1; | A3-B2-C2; | A3-B2-C3; | A3-B2-C4; | A3-B2-C5; | A3-B2-C6; |
| A3-B2-C7; | A3-B2-C8; | A3-B2-C9; | A3-B2-C10; | A3-B2-C11; | A3-B2-C12; |
| A3-B2-C13; | A3-B2-C14; | A3-B2-C15; | A3-B2-C16; | A3-B2-C17; | A3-B2-C18; |
| A3-B2-C19; | A3-B2-C20; | A3-B2-C21; | A3-B2-C22; | A3-B2-C23; | A3-B2-C24; |
| A3-B2-C25; | A3-B2-C26; | A3-B2-C27; | A4-B2-C1; | A4-B2-C2; | A4-B2-C3; |
| A4-B2-C4; | A4-B2-C5; | A4-B2-C6; | A4-B2-C7; | A4-B2-C8; | A4-B2-C9; |
| A4-B2-C10; | A4-B2-C11; | A4-B2-C12; | A4-B2-C13; | A4-B2-C14; | A4-B2-C15; |
| A4-B2-C16; | A4-B2-C17; | A4-B2-C18; | A4-B2-C19; | A4-B2-C20; | A4-B2-C21; |
| A4-B2-C22; | A4-B2-C23; | A4-B2-C24; | A4-B2-C25; | A4-B2-C26; | A4-B2-C27; |
| A5-B2-C1; | A5-B2-C2; | A5-B2-C3; | A5-B2-C4; | A5-B2-C5; | A5-B2-C6; |
| A5-B2-C7; | A5-B2-C8; | A5-B2-C9; | A5-B2-C10; | A5-B2-C11; | A5-B2-C12; |
| A5-B2-C13; | A5-B2-C14; | A5-B2-C15; | A5-B2-C16; | A5-B2-C17; | A5-B2-C18; |
| A5-B2-C19; | A5-B2-C20; | A5-B2-C21; | A5-B2-C22; | A5-B2-C23; | A5-B2-C24; |
| A5-B2-C25; | A5-B2-C26; | A5-B2-C27; | A6-B2-C1; | A6-B2-C2; | A6-B2-C3; |
| A6-B2-C4; | A6-B2-C5; | A6-B2-C6; | A6-B2-C7; | A6-B2-C8; | A6-B2-C9; |
| A6-B2-C10; | A6-B2-C11; | A6-B2-C12; | A6-B2-C13; | A6-B2-C14; | A6-B2-C15; |
| A6-B2-C16; | A6-B2-C17; | A6-B2-C18; | A6-B2-C19; | A6-B2-C20; | A6-B2-C21; |
| A6-B2-C22; | A6-B2-C23; | A6-B2-C24; | A6-B2-C25; | A6-B2-C26; | A6-B2-C27; |
| A7-B2-C1; | A7-B2-C2; | A7-B2-C3; | A7-B2-C4; | A7-B2-C5; | A7-B2-C6; |
| A7-B2-C7; | A7-B2-C8; | A7-B2-C9; | A7-B2-C10; | A7-B2-C11; | A7-B2-C12; |
| A7-B2-C13; | A7-B2-C14; | A7-B2-C15; | A7-B2-C16; | A7-B2-C17; | A7-B2-C18; |
| A7-B2-C19; | A7-B2-C20; | A7-B2-C21; | A7-B2-C22; | A7-B2-C23; | A7-B2-C24; |
| A7-B2-C25; | A7-B2-C26; | A7-B2-C27; | A8-B2-C1; | A8-B2-C2; | A8-B2-C3; |
| A8-B2-C4; | A8-B2-C5; | A8-B2-C6; | A8-B2-C7; | A8-B2-C8; | A8-B2-C9; |
| A8-B2-C10; | A8-B2-C11; | A8-B2-C12; | A8-B2-C13; | A8-B2-C14; | A8-B2-C15; |
| A8-B2-C16; | A8-B2-C17; | A8-B2-C18; | A8-B2-C19; | A8-B2-C20; | A8-B2-C21; |
| A8-B2-C22; | A8-B2-C23; | A8-B2-C24; | A8-B2-C25; | A8-B2-C26; | A8-B2-C27; |
| A9-B2-C1; | A9-B2-C2; | A9-B2-C3; | A9-B2-C4; | A9-B2-C5; | A9-B2-C6; |
| A9-B2-C7; | A9-B2-C8; | A9-B2-C9; | A9-B2-C10; | A9-B2-C11; | A9-B2-C12; |
| A9-B2-C13; | A9-B2-C14; | A9-B2-C15; | A9-B2-C16; | A9-B2-C17; | A9-B2-C18; |
| A9-B2-C19; | A9-B2-C20; | A9-B2-C21; | A9-B2-C22; | A9-B2-C23; | A9-B2-C24; |
| A9-B2-C25; | A9-B2-C26; | A9-B2-C27; | A10-B2-C1; | A10-B2-C2; | A10-B2-C3; |
| A10-B2-C4; | A10-B2-C5; | A10-B2-C6; | A10-B2-C7; | A10-B2-C8; | A10-B2-C9; |
| A10-B2-C10; | A10-B2-C11; | A10-B2-C12; | A10-B2-C13; | A10-B2-C14; | A10-B2-C15; |
| A10-B2-C16; | A10-B2-C17; | A10-B2-C18; | A10-B2-C19; | A10-B2-C20; | A10-B2-C21; |

-continued

| | | | | | |
|---|---|---|---|---|---|
| A10-B2-C22; | A10-B2-C23; | A10-B2-C24; | A10-B2-C25; | A10-B2-C26; | A10-B2-C27; |
| A11-B2-C1; | A11-B2-C2 | A11-B2-C3; | A11-B2-C4; | A11-B2-C5; | A11-B2-C6; |
| A11-B2-C7; | A11-B2-C8; | A11-B2-C9; | A11-B2-C10; | A11-B2-C11; | A11-B2-C12; |
| A11-B2-C13; | A11-B2-C14; | A11-B2-C15; | A11-B2-C16; | A11-B2-C17; | A11-B2-C18; |
| A11-B2-C19; | A11-B2-C20; | A11-B2-C21; | A11-B2-C22; | A11-B2-C23; | A11-B2-C24; |
| A11-B2-C25; | A11-B2-C26; | A11-B2-C27; | A12-B2-C1; | A12-B2-C2; | A12-B2-C3; |
| A12-B2-C4; | A12-B2-C5; | A12-B2-C6; | A12-B2-C7; | A12-B2-C8; | A12-B2-C9; |
| A12-B2-C10; | A12-B2-C11; | A12-B2-C12; | A12-B2-C13; | A12-B2-C14; | A12-B2-C15; |
| A12-B2-C16; | A12-B2-C17; | A12-B2-C18; | A12-B2-C19; | A12-B2-C20; | A12-B2-C21; |
| A12-B2-C22; | A12-B2-C23; | A12-B2-C24; | A12-B2-C25; | A12-B2-C26; | A12-B2-C27; |
| A13-B2-C1; | A13-B2-C2; | A13-B2-C3; | A13-B2-C4; | A13-B2-C5; | A13-B2-C6; |
| A13-B2-C7; | A13-B2-C8; | A13-B2-C9; | A13-B2-C10; | A13-B2-C11; | A13-B2-C12; |
| A13-B2-C13; | A13-B2-C14; | A13-B2-C15; | A13-B2-C16; | A13-B2-C17; | A13-B2-C18; |
| A13-B2-C19; | A13-B2-C20; | A13-B2-C21; | A13-B2-C22; | A13-B2-C23; | A13-B2-C24; |
| A13-B2-C25; | A13-B2-C26; | A13-B2-C27; | A14-B2-C1; | A14-B2-C2; | A14-B2-C3; |
| A14-B2-C4; | A14-B2-C5; | A14-B2-C6; | A14-B2-C7; | A14-B2-C8; | A14-B2-C9; |
| A14-B2-C10; | A14-B2-C11; | A14-B2-C12; | A14-B2-C13; | A14-B2-C14; | A14-B2-C15; |
| A14-B2-C16; | A14-B2-C17; | A14-B2-C18; | A14-B2-C19; | A14-B2-C20; | A14-B2-C21; |
| A14-B2-C22; | A14-B2-C23; | A14-B2-C24; | A14-B2-C25; | A14-B2-C26; | A14-B2-C27; |
| A15-B2-C1; | A15-B2-C2; | A15-B2-C3; | A15-B2-C4; | A15-B2-C5; | A15-B2-C6; |
| A15-B2-C7; | A15-B2-C8; | A15-B2-C9; | A15-B2-C10; | A15-B2-C11; | A15-B2-C12; |
| A15-B2-C13; | A15-B2-C14; | A15-B2-C15; | A15-B2-C16; | A15-B2-C17; | A15-B2-C18; |
| A15-B2-C19; | A15-B2-C20; | A15-B2-C21; | A15-B2-C22; | A15-B2-C23; | A15-B2-C24; |
| A15-B2-C25; | A15-B2-C26; | A15-B2-C27; | A16-B2-C1; | A16-B2-C2; | A16-B2-C3; |
| A16-B2-C4; | A16-B2-C5; | A16-B2-C6; | A16-B2-C7; | A16-B2-C5; | A16-B2-C9; |
| A16-B2-C10; | A16-B2-C11; | A16-B2-C12; | A16-B2-C13; | A16-B2-C14; | A16-B2-C15; |
| A16-B2-C16; | A16-B2-C17; | A16-B2-C18; | A16-B2-C19; | A16-B2-C20; | A16-B2-C21; |
| A16-B2-C22; | A16-B2-C23; | A16-B2-C24; | A16-B2-C25; | A16-B2-C26; | A16-B2-C27; |
| A17-B2-C1; | A17-B2-C2; | A17-B2-C3; | A17-B2-C4; | A17-B2-C5; | A17-B2-C6; |
| A17-B2-C7; | A17-B2-C8; | A17-B2-C9; | A17-B2-C10; | A17-B2-C11; | A17-B2-C12; |
| A17-B2-C13; | A17-B2-C14; | A17-B2-C15; | A17-B2-C16; | A17-B2-C17; | A17-B2-C18; |
| A17-B2-C19; | A17-B2-C20; | A17-B2-C21; | A17-B2-C22; | A17-B2-C23; | A17-B2-C24; |
| A17-B2-C25; | A17-B2-C26; | A17-B2-C27; | A18-B2-C1; | A18-B2-C2; | A18-B2-C3; |
| A18-B2-C4; | A18-B2-C5; | A18-B2-C6; | A18-B2-C7; | A18-B2-C8; | A18-B2-C9; |
| A18-B2-C10; | A18-B2-C11; | A18-B2-C12; | A18-B2-C13; | A18-B2-C14; | A18-B2-C15; |
| A18-B2-C16; | A18-B2-C17; | A18-B2-C18; | A18-B2-C19; | A18-B2-C20; | A18-B2-C21; |
| A18-B2-C22; | A18-B2-C23; | A18-B2-C24; | A18-B2-C25; | A18-B2-C26; | A18-B2-C27; |
| A19-B2-C1; | A19-B2-C2; | A19-B2-C3; | A19-B2-C4; | A19-B2-C5; | A19-B2-C6; |
| A19-B2-C7; | A19-B2-C8; | A19-B2-C9; | A19-B2-C10; | A19-B2-C11; | A19-B2-C12; |
| A19-B2-C13; | A19-B2-C14; | A19-B2-C15; | A19-B2-C16; | A19-B2-C17; | A19-B2-C18; |
| A19-B2-C19; | A19-B2-C20; | A19-B2-C21; | A19-B2-C22; | A19-B2-C23; | A19-B2-C24; |
| A19-B2-C25; | A19-B2-C26; | A19-B2-C27; | A20-B2-C1; | A20-B2-C2; | A20-B2-C3; |
| A20-B2-C4; | A20-B2-C5; | A20-B2-C6; | A20-B2-C7; | A20-B2-C8; | A20-B2-C9; |
| A20-B2-C10; | A20-B2-C11; | A20-B2-C12; | A20-B2-C13; | A20-B2-C14; | A20-B2-C15; |
| A20-B2-C16; | A20-B2-C17; | A20-B2-C18; | A20-B2-C19; | A20-B2-C20; | A20-B2-C21; |
| A20-B2-C22; | A20-B2-C23; | A20-B2-C24; | A20-B2-C25; | A20-B2-C26; | A20-B2-C27; |
| A21-B2-C1; | A21-B2-C2; | A21-B2-C3; | A21-B2-C4; | A21-B2-C5; | A21-B2-C6; |
| A21-B2-C7; | A21-B2-C8; | A21-B2-C9; | A21-B2-C10; | A21-B2-C11; | A21-B2-C12; |
| A21-B2-C13; | A21-B2-C14; | A21-B2-C15; | A21-B2-C16; | A21-B2-C17; | A21-B2-C18; |
| A21-B2-C19; | A21-B2-C20; | A21-B2-C21; | A21-B2-C22; | A21-B2-C23; | A21-B2-C24; |
| A21-B2-C25; | A21-B2-C26; | A21-B2-C27; | A22-B2-C1; | A22-B2-C2; | A22-B2-C3; |
| A22-B2-C4; | A22-B2-C5; | A22-B2-C6; | A22-B2-C7; | A22-B2-C8; | A22-B2-C9; |
| A22-B2-C10; | A22-B2-C11; | A22-B2-C12; | A22-B2-C13; | A22-B2-C14; | A22-B2-C15; |
| A22-B2-C16; | A22-B2-C17; | A22-B2-C18; | A22-B2-C19; | A22-B2-C20; | A22-B2-C21; |
| A22-B2-C22; | A22-B2-C23; | A22-B2-C24; | A22-B2-C25; | A22-B2-C26; | A22-B2-C27; |
| A23-B2-C1; | A23-B2-C2; | A23-B2-C3; | A23-B2-C4; | A23-B2-C5; | A23-B2-C6; |
| A23-B2-C7; | A23-B2-C8; | A23-B2-C9; | A23-B2-C10; | A23-B2-C11; | A23-B2-C12; |
| A23-B2-C13; | A23-B2-C14; | A23-B2-C15; | A23-B2-C16; | A23-B2-C17; | A23-B2-C18; |
| A23-B2-C19; | A23-B2-C20; | A23-B2-C21; | A23-B2-C22; | A23-B2-C23; | A23-B2-C24; |
| A23-B2-C25; | A23-B2-C26; | A23-B2-C27; | A24-B2-C1; | A24-B2-C2; | A24-B2-C3; |
| A24-B2-C4; | A24-B2-C5; | A24-B2-C6; | A24-B2-C7; | A24-B2-C8; | A24-B2-C9; |
| A24-B2-C10; | A24-B2-C11; | A24-B2-C12; | A24-B2-C13; | A24-B2-C14; | A24-B2-C15; |
| A24-B2-C16; | A24-B2-C17; | A24-B2-C18; | A24-B2-C19; | A24-B2-C20; | A24-B2-C21; |
| A24-B2-C22; | A24-B2-C23; | A24-B2-C24; | A24-B2-C25; | A24-B2-C26; | A24-B2-C27; |
| A25-B2-C1; | A25-B2-C2; | A25-B2-C3; | A25-B2-C4; | A25-B2-C5; | A25-B2-C6; |
| A25-B2-C7; | A25-B2-C8; | A25-B2-C9; | A25-B2-C10; | A25-B2-C11; | A25-B2-C12; |
| A25-B2-C13; | A25-B2-C14; | A25-B2-C15; | A25-B2-C16; | A25-B2-C17; | A25-B2-C18; |
| A25-B2-C19; | A25-B2-C20; | A25-B2-C21; | A25-B2-C22; | A25-B2-C23; | A25-B2-C24; |
| A25-B2-C25; | A25-B2-C26; | A25-B2-C27; | A26-B2-C1; | A26-B2-C2; | A26-B2-C3; |
| A26-B2-C4; | A26-B2-C5; | A26-B2-C6; | A26-B2-C7; | A26-B2-C8; | A26-B2-C9; |
| A26-B2-C10; | A26-B2-C11; | A26-B2-C12; | A26-B2-C13; | A26-B2-C14; | A26-B2-C15; |
| A26-B2-C16; | A26-B2-C17; | A26-B2-C18; | A26-B2-C19; | A26-B2-C20; | A26-B2-C21; |
| A26-B2-C22; | A26-B2-C23; | A26-B2-C24; | A26-B2-C25; | A26-B2-C26; | A26-B2-C27; |
| A27-B2-C1; | A27-B2-C2; | A27-B2-C3; | A27-B2-C4; | A27-B2-C5; | A27-B2-C6; |
| A27-B2-C7; | A27-B2-C8; | A27-B2-C9; | A27-B2-C10; | A27-B2-C11; | A27-B2-C12; |
| A27-B2-C13; | A27-B2-C14; | A27-B2-C15; | A27-B2-C16; | A27-B2-C17; | A27-B2-C18; |
| A27-B2-C19; | A27-B2-C20; | A27-B2-C21; | A27-B2-C22; | A27-B2-C23; | A27-B2-C24; |
| A27-B2-C25; | A27-B2-C26; | A27-B2-C27; | A28-B2-C1; | A28-B2-C2; | A28-B2-C3; |
| A28-B2-C4; | A28-B2-C5; | A28-B2-C6; | A28-B2-C7; | A28-B2-C8; | A28-B2-C9; |

-continued

A28-B2-C10; A28-B2-C11; A28-B2-C12; A28-B2-C13; A28-B2-C14; A28-B2-C15;
A28-B2-C16; A28-B2-C17; A28-B2-C18; A28-B2-C19; A28-B2-C20; A28-B2-C21;
A28-B2-C22; A28-B2-C23; A28-B2-C24; A28-B2-C25; A28-B2-C26; A28-B2-C27;
A29-B2-C1; A29-B2-C2; A29-B2-C3; A29-B2-C4; A29-B2-C5; A29-B2-C6;
A29-B2-C7; A29-B2-C8; A29-B2-C9; A29-B2-C10; A29-B2-C11; A29-B2-C12;
A29-B2-C13; A29-B2-C14; A29-B2-C15; A29-B2-C16; A29-B2-C17; A29-B2-C18;
A29-B2-C19; A29-B2-C20; A29-B2-C21; A29-B2-C22; A29-B2-C23; A29-B2-C24;
A29-B2-C25; A29-B2-C26; A29-B2-C27; A30-B2-C1; A30-B2-C2; A30-B2-C3;
A30-B2-C4; A30-B2-C5; A30-B2-C6; A30-B2-C7; A30-B2-C8 A30-B2-C9;
A30-B2-C10; A30-B2-C11; A30-B2-C12; A30-B2-C13; A30-B2-C14; A30-B2-C15;
A30-B2-C16; A30-B2-C17; A30-B2-C18; A30-B2-C19; A30-B2-C20; A30-B2-C21;
A30-B2-C22; A30-B2-C23; A30-B2-C24; A30-B2-C25; A30-B2-C26; A30-B2-C27;
A31-B2-C1; A31-B2-C2; A31-B2-C3; A31-B2-C4; A31-B2-C5; A31-B2-C6;
A31-B2-C7; A31-B2-C8; A31-B2-C9; A31-B2-C10; A31-B2-C11; A31-B2-C12;
A31-B2-C13; A31-B2-C14; A31-B2-C15; A31-B2-C16; A31-B2-C17; A31-B2-C18;
A31-B2-C19; A31-B2-C20; A31-B2-C21; A31-B2-C22; A31-B2-C23; A31-B2-C24;
A31-B2-C25; A31-B2-C26; A31-B2-C27; A32-B2-C1; A32-B2-C2; A32-B2-C3;
A32-B2-C4; A32-B2-C5; A32-B2-C6; A32-B2-C7; A32-B2-C8; A32-B2-C9;
A32-B2-C10; A32-B2-C11; A32-B2-C12; A32-B2-C13; A32-B2-C14; A32-B2-C15;
A32-B2-C16; A32-B2-C17; A32-B2-C18; A32-B2-C19; A32-B2-C20; A32-B2-C21;
A32-B2-C22; A32-B2-C23; A32-B2-C24; A32-B2-C25; A32-B2-C26; A32-B2-C27;
A33-B2-C1; A33-B2-C2; A33-B2-C3; A33-B2-C4; A33-B2-C5; A33-B2-C6;
A33-B2-C7; A33-B2-C8; A33-B2-C9; A33-B2-C10; A33-B2-C11; A33-B2-C12;
A33-B2-C13; A33-B2-C14; A33-B2-C15; A33-B2-C16; A33-B2-C17; A33-B2-C18;
A33-B2-C19; A33-B2-C20; A33-B2-C21; A33-B2-C22; A33-B2-C23; A33-B2-C24;
A33-B2-C25; A33-B2-C26; A33-B2-C27; A34-B2-C1; A34-B2-C2; A34-B2-C3;
A34-B2-C4; A34-B2-C5; A34-B2-C6; A34-B2-C7; A34-B2-C8; A34-B2-C9
A34-B2-C10; A34-B2-C11; A34-B2-C12; A34-B2-C13; A34-B2-C14; A34-B2-C15;
A34-B2-C16; A34-B2-C17; A34-B2-C18; A34-B2-C19; A34-B2-C20; A34-B2-C21;
A34-B2-C22; A34-B2-C23; A34-B2-C24; A34-B2-C25; A34-B2-C26; A34-B2-C27;
A35-B2-C1; A35-B2-C2; A35-B2-C3; A35-B2-C4; A35-B2-C5; A35-B2-C6;
A35-B2-C7; A35-B2-C8; A35-B2-C9; A35-B2-C10; A35-B2-C11; A35-B2-C12;
A35-B2-C13; A35-B2-C14; A35-B2-C15; A35-B2-C16; A35-B2-C17; A35-B2-C18;
A35-B2-C19; A35-B2-C20; A35-B2-C21; A35-B2-C22; A35-B2-C23; A35-B2-C24;
A35-B2-C25; A35-B2-C26; A35-B2-C27; A36-B2-C1; A36-B2-C2; A36-B2-C3;
A36-B2-C4; A36-B2-C5; A36-B2-C6; A36-B2-C7; A36-B2-C8; A36-B2-C9;
A36-B2-C10; A36-B2-C11; A36-B2-C12; A36-B2-C13; A36-B2-C14; A36-B2-C15;
A36-B2-C16; A36-B2-C17; A36-B2-C18; A36-B2-C19; A36-B2-C20; A36-B2-C21;
A36-B2-C22; A36-B2-C23; A36-B2-C24; A36-B2-C25; A36-B2-C26; A36-B2-C27;
A1-B3-C1; A1-B3-C2; A1-B3-C3; A1-B3-C4; A1-B3-C5; A1-B3-C6;
A1-B3-C7; A1-B3-C8; A1-B3-C9; A1-B3-C10; A1-B3-C11; A1-B3-C12;
A1-B3-C13; A1-B3-C14; A1-B3-C15; A1-B3-C16; A1-B3-C17; A1-B3-C18;
A1-B3-C19; A1-B3-C20; A1-B3-C21; A1-B3-C22; A1-B3-C23; A1-B3-C24;
A1-B3-C25; A1-B3-C26; A1-B3-C27; A2-B3-C1; A2-B3-C2; A2-B3-C3;
A2-B3-C4; A2-B3-C5; A2-B3-C6; A2-B3-C7 A2-B3-C8; A2-B3-C9;
A2-B3-C10; A2-B3-C11; A2-B3-C12; A2-B3-C13; A2-B3-C14; A2-B3-C15;
A2-B3-C16; A2-B3-C17; A2-B3-C18; A2-B3-C19; A2-B3-C20; A2-B3-C21;
A2-B3-C22; A2-B3-C23; A2-B3-C24; A2-B3-C25; A2-B3-C26; A2-B3-C27;
A3-B3-C1; A3-B3-C2; A3-B3-C3; A3-B3-C4; A3-B3-C5; A3-B3-C6;
A3-B3-C7; A3-B3-C8; A3-B3-C9; A3-B3-C10; A3-B3-C11; A3-B3-C12;
A3-B3-C13; A3-B3-C14; A3-B3-C15; A3-B3-C16; A3-B3-C17; A3-B3-C18;
A3-B3-C19; A3-B3-C20; A3-B3-C21; A3-B3-C22; A3-B3-C23; A3-B3-C24;
A3-B3-C25; A3-B3-C26; A3-B3-C27; A4-B3-C1; A4-B3-C2; A4-B3-C3;
A4-B3-C4; A4-B3-C5; A4-B3-C6; A4-B3-C7; A4-B3-C8; A4-B3-C9;
A4-B3-C10; A4-B3-C11; A4-B3-C12; A4-B3-C13; A4-B3-C14; A4-B3-C15;
A4-B3-C16; A4-B3-C17; A4-B3-C18; A4-B3-C19; A4-B3-C20; A4-B3-C21;
A4-B3-C22; A4-B3-C23; A4-B3-C24; A4-B3-C25; A4-B3-C26; A4-B3-C27;
A5-B3-C1; A5-B3-C2; A5-B3-C3; A5-B3-C4; A5-B3-C5; A5-B3-C6;
A5-B3-C7; A5-B3-C8; A5-B3-C9; A5-B3-C10; A5-B3-C11; A5-B3-C12;
A5-B3-C13; A5-B3-C14; A5-B3-C15; A5-B3-C16; A5-B3-C17; A5-B3-C18;
A5-B3-C19; A5-B3-C20; A5-B3-C21; A5-B3-C22; A5-B3-C23; A5-B3-C24;
A5-B3-C25; A5-B3-C26; A5-B3-C27; A6-B3-C1; A6-B3-C2; A6-B3-C3;
A6-B3-C4; A6-B3-C5; A6-B3-C6; A6-B3-C7; A6-B3-C8; A6-B3-C9;
A6-B3-C10; A6-B3-C11; A6-B3-C12; A6-B3-C13; A6-B3-C14; A6-B3-C15;
A6-B3-C16; A6-B3-C17; A6-B3-C18; A6-B3-C19; A6-B3-C20; A6-B3-C21;
A6-B3-C22; A6-B3-C23; A6-B3-C24; A6-B3-C25; A6-B3-C26; A6-B3-C27;
A7-B3-C1; A7-B3-C2; A7-B3-C3; A7-B3-C4; A7-B3-C5; A7-B3-C6;
A7-B3-C7; A7-B3-C8; A7-B3-C9; A7-B3-C10; A7-B3-C11; A7-B3-C12;
A7-B3-C13; A7-B3-C14; A7-B3-C15; A7-B3-C16; A7-B3-C17; A7-B3-C18;
A7-B3-C19; A7-B3-C20; A7-B3-C21; A7-B3-C22; A7-B3-C23; A7-B3-C24;
A7-B3-C25; A7-B3-C26; A7-B3-C27; A8-B3-C1; A8-B3-C2; A8-B3-C3;
A8-B3-C4; A8-B3-C5; A8-B3-C6; A8-B3-C7; A8-B3-C8; A8-B3-C9;
A8-B3-C10; A8-B3-C11; A8-B3-C12; A8-B3-C13; A8-B3-C14; A8-B3-C15;
A8-B3-C16; A8-B3-C17; A8-B3-C18; A8-B3-C19; A8-B3-C20; A8-B3-C21;
A8-B3-C22; A8-B3-C23; A8-B3-C24; A8-B3-C25; A8-B3-C26; A8-B3-C27;
A9-B3-C1; A9-B3-C2; A9-B3-C3; A9-B3-C4; A9-B3-C5; A9-B3-C6;
A9-B3-C7; A9-B3-C5; A9-B3-C9; A9-B3-C10; A9-B3-C11; A9-B3-C12;
A9-B3-C13; A9-B3-C14; A9-B3-C15; A9-B3-C16; A9-B3-C17; A9-B3-C18;
A9-B3-C19; A9-B3-C20; A9-B3-C21; A9-B3-C22; A9-B3-C23; A9-B3-C24;

| | | | | | |
|---|---|---|---|---|---|
| A9-B3-C25; | A9-B3-C26; | A9-B3-C27; | A10-B3-C1; | A10-B3-C2; | A10-B3-C3; |
| A10-B3-C4; | A10-B3-C5; | A10-B3-C6; | A10-B3-C7; | A10-B3-C8; | A10-B3-C9; |
| A10-B3-C10; | A10-B3-C11; | A10-B3-C12; | A10-B3-C13; | A10-B3-C14; | A10-B3-C15; |
| A10-B3-C16; | A10-B3-C17; | A10-B3-C18; | A10-B3-C19; | A10-B3-C20; | A10-B3-C21; |
| A10-B3-C22; | A10-B3-C23; | A10-B3-C24; | A10-B3-C25; | A10-B3-C26; | A10-B3-C27; |
| A11-B3-C1; | A11-B3-C2 | A11-B3-C3; | A11-B3-C4; | A11-B3-C5; | A11-B3-C6; |
| A11-B3-C7; | A11-B3-C8; | A11-B3-C9; | A11-B3-C10; | A11-B3-C11; | A11-B3-C12; |
| A11-B3-C13; | A11-B3-C14; | A11-B3-C15; | A11-B3-C16; | A11-B3-C17; | A11-B3-C18; |
| A11-B3-C19; | A11-B3-C20; | A11-B3-C21; | A11-B3-C22; | A11-B3-C23; | A11-B3-C24; |
| A11-B3-C25; | A11-B3-C26; | A12-B3-C27; | A12-B3-C1; | A12-B3-C2; | A12-B3-C3; |
| A12-B3-C4; | A12-B3-C5; | A12-B3-C6; | A12-B3-C7; | A12-B3-C8; | A12-B3-C9; |
| A12-B3-C10; | A12-B3-C11; | A12-B3-C12; | A12-B3-C13; | A12-B3-C14; | A12-B3-C15; |
| A12-B3-C16; | A12-B3-C17; | A12-B3-C18; | A12-B3-C19; | A12-B3-C20; | A12-B3-C21; |
| A12-B3-C22; | A12-B3-C23; | A12-B3-C24; | A12-B3-C25; | A12-B3-C26; | A13-B3-C27; |
| A13-B3-C1; | A13-B3-C2; | A13-B3-C3; | A13-B3-C4; | A13-B3-C5; | A13-B3-C6; |
| A13-B3-C7; | A13-B3-C8; | A13-B3-C9; | A13-B3-C10; | A13-B3-C11; | A13-B3-C12; |
| A13-B3-C13; | A13-B3-C14; | A13-B3-C15; | A13-B3-C16; | A13-B3-C17; | A13-B3-C18; |
| A13-B3-C19; | A13-B3-C20; | A13-B3-C21; | A13-B3-C22; | A13-B3-C23; | A13-B3-C24; |
| A13-B3-C25; | A13-B3-C26; | A14-B3-C27; | A14-B3-C1; | A14-B3-C2; | A14-B3-C3; |
| A14-B3-C4; | A14-B3-C5; | A14-B3-C6; | A14-B3-C7; | A14-B3-C8; | A14-B3-C9; |
| A14-B3-C10; | A14-B3-C11; | A14-B3-C12; | A14-B3-C13; | A14-B3-C14; | A14-B3-C15; |
| A14-B3-C16; | A14-B3-C17; | A14-B3-C18; | A14-B3-C19; | A14-B3-C20; | A14-B3-C21; |
| A14-B3-C22; | A14-B3-C23; | A14-B3-C24; | A14-B3-C25; | A14-B3-C26; | A14-B3-C27; |
| A15-B3-C1; | A15-B3-C2; | A15-B3-C3; | A15-B3-C4; | A15-B3-C5; | A15-B3-C6; |
| A15-B3-C7; | A15-B3-C8; | A15-B3-C9; | A15-B3-C10; | A15-B3-C11; | A15-B3-C12; |
| A15-B3-C13; | A15-B3-C14; | A15-B3-C15; | A15-B3-C16; | A15-B3-C17; | A15-B3-C18; |
| A15-B3-C19; | A15-B3-C20; | A15-B3-C21; | A15-B3-C22; | A15-B3-C23; | A15-B3-C24; |
| A15-B3-C25; | A15-B3-C26; | A15-B3-C27; | A16-B3-C1; | A16-B3-C2; | A16-B3-C3; |
| A16-B3-C4; | A16-B3-C5; | A16-B3-C6; | A16-B3-C7; | A16-B3-C8; | A16-B3-C9; |
| A16-B3-C10; | A16-B3-C11; | A16-B3-C12; | A16-B3-C13; | A16-B3-C14; | A16-B3-C15; |
| A16-B3-C16; | A16-B3-C17; | A16-B3-C18; | A16-B3-C19; | A16-B3-C20; | A16-B3-C21; |
| A16-B3-C22; | A16-B3-C23; | A16-B3-C24; | A16-B3-C25; | A16-B3-C26; | A16-B3-C27; |
| A17-B3-C1; | A17-B3-C2; | A17-B3-C3; | A17-B3-C4; | A17-B3-C5; | A17-B3-C6; |
| A17-B3-C7; | A17-B3-C5; | A17-B3-C9; | A17-B3-C10; | A17-B3-C11; | A17-B3-C12; |
| A17-B3-C13; | A17-B3-C14; | A17-B3-C15; | A17-B3-C16; | A17-B3-C17; | A17-B3-C18; |
| A17-B3-C19; | A17-B3-C20; | A17-B3-C21; | A17-B3-C22; | A17-B3-C23; | A17-B3-C24; |
| A17-B3-C25; | A17-B3-C26; | A17-B3-C27; | A18-B3-C1; | A18-B3-C2; | A18-B3-C3; |
| A18-B3-C4; | A18-B3-C5; | A18-B3-C6; | A15-B3-C7; | A18-B3-C8; | A18-B3-C9; |
| A18-B3-C10; | A18-B3-C11; | A15-B3-C12; | A18-B3-C13; | A18-B3-C14; | A18-B3-C15; |
| A18-B3-C16; | A18-B3-C17; | A18-B3-C18; | A18-B3-C19; | A18-B3-C20; | A18-B3-C21; |
| A15-B3-C22; | A15-B3-C23; | A18-B3-C24; | A18-B3-C25; | A18-B3-C26; | A19-B3-C27; |
| A19-B3-C1; | A19-B3-C2; | A19-B3-C3; | A19-B3-C4; | A19-B3-C5; | A19-B3-C6; |
| A19-B3-C7; | A19-B3-C8; | A19-B3-C9; | A19-B3-C10; | A19-B3-C11; | A19-B3-C12; |
| A19-B3-C13; | A19-B3-C14; | A19-B3-C15; | A19-B3-C16; | A19-B3-C17; | A19-B3-C18; |
| A19-B3-C19; | A19-B3-C20; | A19-B3-C21; | A19-B3-C22; | A19-B3-C23; | A19-B3-C24; |
| A19-B3-C25; | A19-B3-C26; | A19-B3-C27; | A20-B3-C1; | A20-B3-C2; | A20-B3-C3; |
| A20-B3-C4; | A20-B3-C5; | A20-B3-C6; | A20-B3-C7; | A20-B3-C8; | A20-B3-C9; |
| A20-B3-C10; | A20-B3-C11; | A20-B3-C12; | A20-B3-C13; | A20-B3-C14; | A20-B3-C15; |
| A20-B3-C16; | A20-B3-C17; | A20-B3-C18; | A20-B3-C19; | A20-B3-C20; | A20-B3-C21; |
| A20-B3-C22; | A20-B3-C23; | A20-B3-C24; | A20-B3-C25; | A20-B3-C26; | A20-B3-C27; |
| A21-B3-C1; | A21-B3-C2; | A21-B3-C3; | A21-B3-C4; | A21-B3-C5; | A21-B3-C6; |
| A21-B3-C7; | A21-B3-C8; | A21-B3-C9; | A21-B3-C10; | A21-B3-C11; | A21-B3-C12; |
| A21-B3-C13; | A21-B3-C14; | A21-B3-C15; | A21-B3-C16; | A21-B3-C17; | A21-B3-C18; |
| A21-B3-C19; | A21-B3-C20; | A21-B3-C21; | A21-B3-C22; | A21-B3-C23; | A21-B3-C24; |
| A21-B3-C25; | A21-B3-C26; | A21-B3-C27; | A22-B3-C1; | A22-B3-C2; | A22-B3-C3; |
| A22-B3-C4; | A22-B3-C5; | A22-B3-C6; | A22-B3-C7; | A22-B3-C8; | A22-B3-C9; |
| A22-B3-C10; | A22-B3-C11; | A22-B3-C12; | A22-B3-C13; | A22-B3-C14; | A22-B3-C15; |
| A22-B3-C16; | A22-B3-C17; | A22-B3-C18; | A22-B3-C19; | A22-B3-C20; | A22-B3-C21; |
| A22-B3-C22; | A22-B3-C23; | A22-B3-C24; | A22-B3-C25; | A22-B3-C26; | A22-B3-C27; |
| A23-B3-C1; | A23-B3-C2; | A23-B3-C3; | A23-B3-C4; | A23-B3-C5; | A23-B3-C6; |
| A23-B3-C7; | A23-B3-C8; | A23-B3-C9; | A23-B3-C10; | A23-B3-C11; | A23-33-C12; |
| A23-B3-C13; | A23-B3-C14; | A23-B3-C15; | A23-B3-C16; | A23-B3-C17; | A23-B3-C18; |
| A23-B3-C19; | A23-B3-C20; | A23-B3-C21; | A23-B3-C22; | A23-B3-C23; | A23-B3-C24; |
| A23-B3-C25; | A23-B3-C26; | A23-B3-C27; | A24-B3-C1; | A24-B3-C2; | A24-B3-C3; |
| A24-B3-C4; | A24-B3-C5; | A24-B3-C6; | A24-B3-C7; | A24-B3-C8; | A24-B3-C9; |
| A24-B3-C10; | A24-B3-C11; | A24-B3-C12; | A24-B3-C13; | A24-B3-C14; | A24-B3-C15; |
| A24-B3-C16; | A24-B3-C17; | A24-B3-C18; | A24-B3-C19; | A24-B3-C20; | A24-B3-C21; |
| A24-B3-C22; | A24-B3-C23; | A24-B3-C24; | A24-B3-C25; | A24-B3-C26; | A24-B3-C27; |
| A25-B3-C1; | A25-B3-C2; | A25-B3-C3; | A25-B3-C4; | A25-B3-C5; | A25-B3-C6; |
| A25-B3-C7; | A25-B3-C8; | A25-B3-C9; | A25-B3-C10; | A25-B3-C11; | A25-B3-C12; |
| A25-B3-C13; | A25-B3-C14; | A25-B3-C15; | A25-B3-C16; | A25-B3-C17; | A25-B3-C18; |
| A25-B3-C19; | A25-B3-C20; | A25-B3-C21; | A25-B3-C22; | A25-B3-C23; | A25-B3-C24; |
| A25-B3-C25; | A25-B3-C26; | A25-B3-C27; | A26-B3-C1; | A26-B3-C2; | A26-B3-C3; |
| A26-B3-C4; | A26-B3-C5; | A26-B3-C6; | A26-B3-C7; | A26-B3-C8; | A26-B3-C9; |
| A26-B3-C10; | A26-33-C11; | A26-B3-C12; | A26-B3-C13; | A26-B3-C14; | A26-B3-C15; |
| A26-B3-C16; | A26-B3-C17; | A26-B3-C18; | A26-B3-C19; | A26-B3-C20; | A26-B3-C21; |
| A26-B3-C22; | A26-B3-C23; | A26-B3-C24; | A26-B3-C25; | A26-B3-C26; | A26-B3-C27; |
| A27-B3-C1; | A27-B3-C2; | A27-B3-C3; | A27-B3-C4; | A27-B3-C5; | A27-B3-C6; |
| A27-B3-C7; | A27-B3-C8; | A27-B3-C9; | A27-B3-C10; | A27-B3-C11; | A27-B3-C12; |

-continued

| | | | | | |
|---|---|---|---|---|---|
| A27-B3-C13; | A27-B3-C14; | A27-B3-C15; | A27-B3-C16; | A27-B3-C17; | A27-B3-C18; |
| A27-B3-C19; | A27-B3-C20; | A27-B3-C21; | A27-B3-C22; | A27-33-C23; | A27-B3-C24; |
| A27-B3-C25; | A27-B3-C26; | A27-B3-C27; | A28-B3-C1; | A28-B3-C2; | A28-B3-C3; |
| A28-B3-C4; | A28-B3-C5; | A28-B3-C6; | A28-B3-C7; | A28-B3-C8; | A28-B3-C9; |
| A28-B3-C10; | A28-B3-C11; | A28-B3-C12; | A28-B3-C13; | A28-B3-C14; | A28-B3-C15; |
| A28-B3-C16; | A28-B3-C17; | A28-B3-C18; | A28-B3-C19; | A28-B3-C20; | A28-B3-C21; |
| A28-B3-C22; | A28-B3-C23; | A28-B3-C24; | A28-B3-C25; | A28-B3-C26; | A28-B3-C27; |
| A29-B3-C1; | A29-B3-C2; | A29-B3-C3; | A29-B3-C4; | A29-B3-C5; | A29-B3-C6; |
| A29-B3-C7; | A29-B3-C8; | A29-B3-C9; | A29-B3-C10; | A29-B3-C11; | A29-B3-C12; |
| A29-B3-C13; | A29-B3-C14; | A29-B3-C15; | A29-B3-C16; | A29-B3-C17; | A29-B3-C18; |
| A29-B3-C19; | A29-B3-C20; | A29-B3-C21; | A29-B3-C22; | A29-B3-C23; | A29-B3-C24; |
| A29-B3-C25; | A29-B3-C26; | A29-B3-C27; | A30-B3-C1; | A30-B3-C2; | A30-B3-C3; |
| A30-B3-C4; | A30-B3-C5; | A30-B3-C6; | A30-B3-C7; | A30-B3-C8 | A30-B3-C9; |
| A30-B3-C10; | A30-B3-C11; | A30-B3-C12; | A30-B3-C13; | A30-B3-C14; | A30-B3-C15; |
| A30-B3-C16; | A30-B3-C17; | A30-B3-C18; | A30-B3-C19; | A30-B3-C20; | A30-B3-C21; |
| A30-B3-C22; | A30-B3-C23; | A30-B3-C24; | A30-B3-C25; | A30-B3-C26; | A30-B3-C27; |
| A31-B3-C1; | A31-B3-C2; | A31-B3-C3; | A31-B3-C4; | A31-B3-C5; | A31-B3-C6; |
| A31-B3-C7; | A31-B3-C8; | A31-B3-C9; | A31-B3-C10; | A31-B3-C11; | A31-B3-C12; |
| A31-B3-C13; | A31-B3-C14; | A31-B3-C15; | A31-B3-C16; | A31-B3-C17; | A31-B3-C18; |
| A31-B3-C19; | A31-B3-C20; | A31-B3-C21; | A31-B3-C22; | A31-B3-C23; | A31-B3-C24; |
| A31-B3-C25; | A31-B3-C26; | A31-B3-C27; | A32-B3-C1; | A32-B3-C2; | A32-B3-C3; |
| A32-B3-C4; | A32-B3-C5; | A32-B3-C6; | A32-B3-C7; | A32-B3-C8; | A32-B3-C9; |
| A32-B3-C10; | A32-B3-C11; | A32-B3-C12; | A32-B3-C13; | A32-B3-C14; | A32-B3-C15; |
| A32-B3-C16; | A32-B3-C17; | A32-B3-C18; | A32-B3-C19; | A32-B3-C20; | A32-B3-C21; |
| A32-B3-C22; | A32-B3-C23; | A32-B3-C24; | A32-B3-C25; | A32-B3-C26; | A32-B3-C27; |
| A33-B3-C1; | A33-B3-C2; | A33-B3-C3; | A33-B3-C4; | A33-B3-C5; | A33-B3-C6; |
| A33-B3-C7; | A33-B3-C8; | A33-B3-C9; | A33-B3-C10; | A33-B3-C11; | A33-B3-C12; |
| A33-B3-C13; | A33-B3-C14; | A33-B3-C15; | A33-B3-C16; | A33-B3-C17; | A33-B3-C18; |
| A33-B3-C19; | A33-B3-C20; | A33-B3-C21; | A33-B3-C22; | A33-B3-C23; | A33-B3-C24; |
| A33-B3-C25; | A33-B3-C26; | A33-B3-C27; | A34-B3-C1; | A34-B3-C2; | A34-B3-C3; |
| A34-B3-C4; | A34-B3-C5; | A34-B3-C6; | A34-B3-C7; | A34-B3-C8; | A34-B3-C9 |
| A34-B3-C10; | A34-B3-C11; | A34-B3-C12; | A34-B3-C13; | A34-B3-C14; | A34-B3-C15; |
| A34-B3-C16; | A34-B3-C17; | A34-B3-C18; | A34-B3-C19; | A34-B3-C20; | A34-B3-C21; |
| A34-B3-C22; | A34-B3-C23; | A34-B3-C24; | A34-B3-C25; | A34-B3-C26; | A34-B3-C27; |
| A35-B3-C1; | A35-B3-C2; | A35-B3-C3; | A35-B3-C4; | A35-B3-C5; | A35-B3-C6; |
| A35-B3-C7; | A35-B3-C8; | A35-B3-C9; | A35-B3-C10; | A35-B3-C11; | A35-B3-C12; |
| A35-B3-C13; | A35-B3-C14; | A35-B3-C15; | A35-B3-C16; | A35-B3-C17; | A35-B3-C18; |
| A35-B3-C19; | A35-B3-C20; | A35-B3-C21; | A35-B3-C22; | A35-B3-C23; | A35-B3-C24; |
| A35-B3-C25; | A35-B3-C26; | A35-B3-C27; | A36-B3-C1; | A36-B3-C2; | A36-B3-C3; |
| A36-B3-C4; | A36-B3-C5; | A36-B3-C6; | A36-B3-C7; | A36-B3-C8; | A36-B3-C9; |
| A36-B3-C10; | A36-B3-C11; | A36-B3-C12; | A36-B3-C13; | A36-B3-C14; | A36-B3-C15; |
| A36-B3-C16; | A36-B3-C17; | A36-B3-C18; | A36-B3-C19; | A36-B3-C20; | A36-B3-C21; |
| A36-B3-C22; | A36-B3-C23; | A36-B3-C24; | A36-B3-C25; | A36-B3-C26; | A36-B3-C27; |
| A1-B4-C1; | A1-B4-C2; | A1-B4-C3; | A1-B4-C4; | A1-B4-C5; | A1-B4-C6; |
| A1-B4-C7; | A1-B4-C8; | A1-B4-C9; | A1-B4-C10; | A1-B4-C11; | A1-B4-C12; |
| A1-B4-C13; | A1-B4-C14; | A1-B4-C15; | A1-B4-C16; | A1-B4-C17; | A1-B4-C18; |
| A1-B4-C19; | A1-B4-C20; | A1-B4-C21; | A1-B4-C22; | A1-B4-C23; | A1-B4-C24; |
| A1-B4-C25; | A1-B4-C26; | A1-B4-C27; | A2-B4-C1; | A2-B4-C2; | A2-B4-C3; |
| A2-B4-C4; | A2-B4-C5; | A2-B4-C6; | A2-B4-C7 | A2-B4-C8; | A2-B4-C9; |
| A2-B4-C10; | A2-B4-C11; | A2-B4-C12; | A2-B4-C13; | A2-B4-C14; | A2-B4-C15; |
| A2-B4-C16; | A2-B4-C17; | A2-B4-C18; | A2-B4-C19; | A2-B4-C20; | A2-B4-C21; |
| A2-B4-C22; | A2-B4-C23; | A2-B4-C24; | A2-B4-C25; | A2-B4-C26; | A2-B4-C27; |
| A3-B4-C1; | A3-B4-C2; | A3-B4-C3; | A3-B4-C4; | A3-B4-C5; | A3-B4-C6; |
| A3-B4-C7; | A3-B4-C8; | A3-B4-C9; | A3-B4-C10; | A3-B4-C11; | A3-B4-C12; |
| A3-B4-C13; | A3-B4-C14; | A3-B4-C15; | A3-B4-C16; | A3-B4-C17; | A3-B4-C18; |
| A3-B4-C19; | A3-B4-C20; | A3-B4-C21; | A3-B4-C22; | A3-B4-C23; | A3-B4-C24; |
| A3-B4-C25; | A3-B4-C26; | A3-B4-C27; | A4-B4-C1; | A4-B4-C2; | A4-B4-C3; |
| A4-B4-C4; | A4-B4-C5; | A4-B4-C6; | A4-B4-C7; | A4-B4-C8; | A4-B4-C9; |
| A4-B4-C10; | A4-B4-C11; | A4-B4-C12; | A4-B4-C13; | A4-B4-C14; | A4-B4-C15; |
| A4-B4-C16; | A4-B4-C17; | A4-B4-C18; | A4-B4-C19; | A4-B4-C20; | A4-B4-C21; |
| A4-B4-C22; | A4-B4-C23; | A4-B4-C24; | A4-B4-C25; | A4-B4-C26; | A4-B4-C27; |
| A5-B4-C1; | A5-B4-C2; | A5-B4-C3; | A5-B4-C4; | A5-B4-C5; | A5-B4-C6; |
| A5-B4-C7; | A5-B4-C8; | A5-B4-C9; | A5-B4-C10; | A5-B4-C11; | A5-B4-C12; |
| A5-B4-C13; | A5-B4-C14; | A5-B4-C15; | A5-B4-C16; | A5-B4-C17; | A5-B4-C18; |
| A5-B4-C19; | A5-B4-C20; | A5-B4-C21; | A5-B4-C22; | A5-B4-C23; | A5-B4-C24; |
| A5-B4-C25; | A5-B4-C26; | A5-B4-C27; | A6-B4-C1; | A6-B4-C2; | A6-B4-C3; |
| A6-B4-C4; | A6-B4-C5; | A6-B4-C6; | A6-B4-C7; | A6-B4-C8; | A6-B4-C9; |
| A6-B4-C10; | A6-B4-C11; | A6-B4-C12; | A6-B4-C13; | A6-B4-C14; | A6-B4-C15; |
| A6-B4-C16; | A6-B4-C17; | A6-B4-C18; | A6-B4-C19; | A6-B4-C20; | A6-B4-C21; |
| A6-B4-C22; | A6-B4-C23; | A6-B4-C24; | A6-B4-C25; | A6-B4-C26; | A6-B4-C27; |
| A7-B4-C1; | A7-B4-C2; | A7-B4-C3; | A7-B4-C4; | A7-B4-C5; | A7-B4-C6; |
| A7-B4-C7; | A7-B4-C8; | A7-B4-C9; | A7-B4-C10; | A7-B4-C11; | A7-B4-C12; |
| A7-B4-C13; | A7-B4-C14; | A7-B4-C15; | A7-B4-C16; | A7-B4-C17; | A7-B4-C18; |
| A7-B4-C19; | A7-B4-C20; | A7-B4-C21; | A7-B4-C22; | A7-B4-C23; | A7-B4-C24; |
| A7-B4-C25; | A7-B4-C26; | A7-B4-C27; | A8-B4-C1; | A8-B4-C2; | A8-B4-C3; |
| A8-B4-C4; | A8-B4-C5; | A8-B4-C6; | A8-B4-C7; | A8-B4-C8; | A8-B4-C9; |
| A8-B4-C10; | A8-B4-C11; | A8-B4-C12; | A8-B4-C13; | A8-B4-C14; | A8-B4-C15; |
| A8-B4-C16; | A8-B4-C17; | A8-B4-C18; | A8-B4-C19; | A8-B4-C20; | A8-B4-C21; |
| A8-B4-C22; | A8-B4-C23; | A8-B4-C24; | A8-B4-C25; | A8-B4-C26; | A8-B4-C27; |

-continued

| | | | | | |
|---|---|---|---|---|---|
| A9-B4-C1; | A9-B4-C2; | A9-B4-C3; | A9-B4-C4; | A9-B4-C5; | A9-B4-C6; |
| A9-B4-C7; | A9-B4-C8; | A9-B4-C9; | A9-B4-C10; | A9-B4-C11; | A9-B4-C12; |
| A9-B4-C13; | A9-B4-C14; | A9-B4-C15; | A9-B4-C16; | A9-B4-C17; | A9-B4-C18; |
| A9-B4-C19; | A9-B4-C20; | A9-B4-C21; | A9-B4-C22; | A9-B4-C23; | A9-B4-C24; |
| A9-B4-C25; | A9-B4-C26; | A9-B4-C27; | A10-B4-C1; | A10-B4-C2; | A10-B4-C3; |
| A10-B4-C4; | A10-B4-C5; | A10-B4-C6; | A10-B4-C7; | A10-B4-C8; | A10-B4-C9; |
| A10-B4-C10; | A10-B4-C11; | A10-B4-C12; | A10-B4-C13; | A10-B4-C14; | A10-B4-C15; |
| A10-B4-C16; | A10-B4-C17; | A10-B4-C18; | A10-B4-C19; | A10-B4-C20; | A10-B4-C21; |
| A10-B4-C22; | A10-B4-C23; | A10-B4-C24; | A10-B4-C25; | A10-B4-C26; | A10-B4-C27; |
| A11-B4-C1; | A11-B4-C2 | A11-B4-C3; | A11-B4-C4; | A11-B4-C5; | A11-B4-C6; |
| A11-B4-C7; | A11-B4-C8; | A11-B4-C9; | A11-B4-C10; | A11-B4-C11; | A11-B4-C12; |
| A11-B4-C13; | A11-B4-C14; | A11-B4-C15; | A11-B4-C16; | A11-B4-C17; | A11-B4-C18; |
| A11-B4-C19; | A11-B4-C20; | A11-B4-C21; | A11-B4-C22; | A11-B4-C23; | A11-B4-C24; |
| A11-B4-C25; | A11-B4-C26; | A11-B4-C27; | A12-B4-C1; | A12-B4-C2; | A12-B4-C3; |
| A12-B4-C4; | A12-B4-C5; | A12-B4-C6; | A12-B4-C7; | A12-B4-C8; | A12-B4-C9; |
| A12-B4-C10; | A12-B4-C11; | A12-B4-C12; | A12-B4-C13; | A12-B4-C14; | A12-B4-C15; |
| A12-B4-C16; | A12-B4-C17; | A12-B4-C18; | A12-B4-C19; | A12-B4-C20; | A12-B4-C21; |
| A12-B4-C22; | A12-B4-C23; | A12-B4-C24; | A12-B4-C25; | A12-B4-C26; | A12-B4-C27; |
| A13-B4-C1; | A13-B4-C2; | A13-B4-C3; | A13-B4-C4; | A13-B4-C5; | A13-B4-C6; |
| A13-B4-C7; | A13-B4-C8; | A13-B4-C9; | A13-B4-C10; | A13-B4-C11; | A13-B4-C12; |
| A13-B4-C13; | A13-B4-C14; | A13-B4-C15; | A13-B4-C16; | A13-B4-C17; | A13-B4-C18; |
| A13-B4-C19; | A13-B4-C20; | A13-B4-C21; | A13-B4-C22; | A13-B4-C23; | A13-B4-C24; |
| A13-B4-C25; | A13-B4-C26; | A13-B4-C27; | A14-B4-C1; | A14-B4-C2; | A14-B4-C3; |
| A14-B4-C4; | A14-B4-C5; | A14-B4-C6; | A14-B4-C7; | A14-B4-C8; | A14-B4-C9; |
| A14-B4-C10; | A14-B4-C11; | A14-B4-C12; | A14-B4-C13; | A14-B4-C14; | A14-B4-C15; |
| A14-B4-C16; | A14-B4-C17; | A14-B4-C18; | A14-B4-C19; | A14-B4-C20; | A14-B4-C21; |
| A14-B4-C22; | A14-B4-C23; | A14-B4-C24; | A14-B4-C25; | A14-B4-C26; | A14-B4-C27; |
| A15-B4-C1; | A15-B4-C2; | A15-B4-C3; | A15-B4-C4; | A15-B4-C5; | A15-B4-C6; |
| A15-B4-C7; | A15-B4-C8; | A15-B4-C9; | A15-B4-C10; | A15-B4-C11; | A15-B4-C12; |
| A15-B4-C13; | A15-B4-C14; | A15-B4-C15; | A15-B4-C16; | A15-B4-C17; | A15-B4-C18; |
| A15-B4-C19; | A15-B4-C20; | A15-B4-C21; | A15-B4-C22; | A15-B4-C23; | A15-B4-C24; |
| A15-B4-C25; | A15-B4-C26; | A15-B4-C27; | A16-B4-C1; | A16-B4-C2; | A16-B4-C3; |
| A16-B4-C4; | A16-B4-C5; | A16-B4-C6; | A16-B4-C7; | A16-B4-C8; | A16-B4-C9; |
| A16-B4-C10; | A16-B4-C11; | A16-B4-C12; | A16-B4-C13; | A16-B4-C14; | A16-B4-C15; |
| A16-B4-C16; | A16-B4-C17; | A16-B4-C18; | A16-B4-C19; | A16-B4-C20; | A16-B4-C21; |
| A16-B4-C22; | A16-B4-C23; | A16-B4-C24; | A16-B4-C25; | A16-B4-C26; | A16-B4-C27; |
| A17-B4-C1; | A17-B4-C2 | A17-B4-C3; | A17-B4-C4; | A17-B4-C5; | A17-B4-C6; |
| A17-B4-C7; | A17-B4-C8; | A17-B4-C9; | A17-B4-C10; | A17-B4-C11; | A17-B4-C12; |
| A17-B4-C13; | A17-B4-C14; | A17-B4-C15; | A17-B4-C16; | A17-B4-C17; | A17-B4-C18; |
| A17-B4-C19; | A17-B4-C20; | A17-B4-C21; | A17-B4-C22; | A17-B4-C23; | A17-B4-C24; |
| A17-B4-C25; | A17-B4-C26; | A17-B4-C27; | A18-B4-C1; | A18-B4-C2; | A18-B4-C3; |
| A18-B4-C4; | A18-B4-C5; | A18-B4-C6; | A18-B4-C7; | A18-B4-C8; | A18-B4-C9; |
| A18-B4-C10; | A18-B4-C11; | A18-B4-C12; | A18-B4-C13; | A18-B4-C14; | A18-B4-C15; |
| A18-B4-C16; | A18-B4-C17; | A18-B4-C18; | A18-B4-C19; | A15-B4-C20; | A18-B4-C21; |
| A18-B4-C22; | A18-B4-C23; | A18-B4-C24; | A18-B4-C25; | A18-B4-C26; | A18-B4-C27; |
| A19-B4-C1; | A19-B4-C2; | A19-B4-C3; | A19-B4-C4; | A19-B4-C5; | A19-B4-C6; |
| A19-B4-C7; | A19-B4-C8; | A19-B4-C9; | A19-B4-C10; | A19-B4-C11; | A19-B4-C12; |
| A19-B4-C13; | A19-B4-C14; | A19-B4-C15; | A19-B4-C16; | A19-B4-C17; | A19-B4-C18; |
| A19-B4-C19; | A19-B4-C20; | A19-B4-C21; | A19-B4-C22; | A19-B4-C23; | A19-B4-C24; |
| A19-B4-C25; | A19-B4-C26; | A19-B4-C27; | A20-B4-C1; | A20-B4-C2; | A20-B4-C3; |
| A20-B4-C4; | A20-B4-C5; | A20-B4-C6; | A20-B4-C7; | A20-B4-C8; | A20-B4-C9; |
| A20-B4-C10; | A20-B4-C11; | A20-B4-C12; | A20-B4-C13; | A20-B4-C14; | A20-B4-C15; |
| A20-B4-C16; | A20-B4-C17; | A20-B4-C18; | A20-B4-C19; | A20-B4-C20; | A20-B4-C21; |
| A20-B4-C22; | A20-B4-C23; | A20-B4-C24; | A20-B4-C25; | A20-B4-C26; | A20-B4-C27; |
| A21-B4-C1; | A21-B4-C2; | A21-B4-C3; | A21-B4-C4; | A21-B4-C5; | A21-B4-C6; |
| A21-B4-C7; | A21-B4-C8; | A21-B4-C9; | A21-B4-C10; | A21-B4-C11; | A21-B4-C12; |
| A21-B4-C13; | A21-B4-C14; | A21-B4-C15; | A21-B4-C16; | A21-B4-C17; | A21-B4-C18; |
| A21-B4-C19; | A21-B4-C20; | A21-B4-C21; | A21-B4-C22; | A21-B4-C23; | A21-B4-C24; |
| A21-B4-C25; | A21-B4-C26; | A21-B4-C27; | A22-B4-C1; | A22-B4-C2; | A22-B4-C3; |
| A22-B4-C4; | A22-B4-C5; | A22-B4-C6; | A22-B4-C7; | A22-B4-C8; | A22-34-C9; |
| A22-B4-C10; | A22-B4-C11; | A22-B4-C12; | A22-B4-C13; | A22-B4-C14; | A22-B4-C15; |
| A22-B4-C16; | A22-B4-C17; | A22-B4-C18; | A22-B4-C19; | A22-B4-C20; | A22-B4-C21; |
| A22-B4-C22; | A22-B4-C23; | A22-B4-C24; | A22-B4-C25; | A22-B4-C26; | A22-B4-C27; |
| A23-B4-C1; | A23-B4-C2; | A23-B4-C3; | A23-B4-C4; | A23-B4-C5; | A23-B4-C6; |
| A23-B4-C7; | A23-B4-C8; | A23-B4-C9; | A23-B4-C10; | A23-B4-C11; | A23-B4-C12; |
| A23-B4-C13; | A23-B4-C14; | A23-B4-C15; | A23-B4-C16; | A23-B4-C17; | A23-B4-C18; |
| A23-B4-C19; | A23-B4-C20; | A23-B4-C21; | A23-B4-C22; | A23-B4-C23; | A23-B4-C24; |
| A23-B4-C25; | A23-B4-C26; | A23-B4-C27; | A24-B4-C1; | A24-B4-C2; | A24-B4-C3; |
| A24-B4-C4; | A24-B4-C5; | A24-B4-C6; | A24-B4-C7; | A24-B4-C8; | A24-B4-C9; |
| A24-B4-C10; | A24-B4-C11; | A24-B4-C12; | A24-B4-C13; | A24-B4-C14; | A24-B4-C15; |
| A24-B4-C16; | A24-B4-C17; | A24-B4-C18; | A24-B4-C19; | A24-B4-C20; | A24-B4-C21; |
| A24-B4-C22; | A24-B4-C23; | A24-B4-C24; | A24-B4-C25; | A24-B4-C26; | A24-B4-C27; |
| A25-B4-C1; | A25-B4-C2; | A25-B4-C3; | A25-B4-C4; | A25-B4-C5; | A25-B4-C6; |
| A25-B4-C7; | A25-B4-C8; | A25-B4-C9; | A25-B4-C10; | A25-B4-C11; | A25-B4-C12; |
| A25-B4-C13; | A25-B4-C14; | A25-B4-C15; | A25-B4-C16; | A25-B4-C17; | A25-B4-C18; |
| A25-B4-C19; | A25-B4-C20; | A25-B4-C21; | A25-B4-C22; | A25-B4-C23; | A25-B4-C24; |
| A25-B4-C25; | A25-B4-C26; | A25-B4-C27; | A26-B4-C1; | A26-B4-C2; | A26-B4-C3; |
| A26-B4-C4; | A26-B4-C5; | A26-B4-C6; | A26-B4-C7; | A26-B4-C8; | A26-B4-C9; |
| A26-B4-C10; | A26-B4-C11; | A26-B4-C12; | A26-B4-C13; | A26-B4-C14; | A26-B4-C15; |

-continued

| | | | | | |
|---|---|---|---|---|---|
| A26-B4-C16; | A26-B4-C17; | A26-B4-C18; | A26-B4-C19; | A26-B4-C20; | A26-B4-C21; |
| A26-B4-C22; | A26-B4-C23; | A26-B4-C24; | A26-B4-C25; | A26-B4-C26; | A26-B4-C27; |
| A27-B4-C1; | A27-B4-C2; | A27-B4-C3; | A27-B4-C4; | A27-B4-C5; | A27-B4-C6; |
| A27-B4-C7; | A27-B4-C8; | A27-B4-C9; | A27-B4-C10; | A27-B4-C11; | A27-B4-C12; |
| A27-B4-C13; | A27-B4-C14; | A27-B4-C15; | A27-B4-C16; | A27-B4-C17; | A27-B4-C18; |
| A27-B4-C19; | A27-B4-C20; | A27-B4-C21; | A27-B4-C22; | A27-B4-C23; | A27-B4-C24; |
| A27-B4-C25; | A27-B4-C26; | A27-B4-C27; | A28-B4-C1; | A28-B4-C2; | A28-B4-C3; |
| A28-B4-C4; | A28-B4-C5; | A28-B4-C6; | A28-B4-C7; | A28-B4-C8; | A28-B4-C9; |
| A28-B4-C10; | A28-B4-C11; | A28-B4-C12; | A28-B4-C13; | A28-B4-C14; | A28-B4-C15; |
| A28-B4-C16; | A28-B4-C17; | A28-B4-C18; | A28-B4-C19; | A28-B4-C20; | A28-B4-C21; |
| A28-B4-C22; | A28-B4-C23; | A28-B4-C24; | A28-B4-C25; | A28-B4-C26; | A28-B4-C27; |
| A29-B4-C1; | A29-B4-C2; | A29-B4-C3; | A29-B4-C4; | A29-B4-C5; | A29-B4-C6; |
| A29-B4-C7; | A29-B4-C8; | A29-B4-C9; | A29-B4-C10; | A29-B4-C11; | A29-B4-C12; |
| A29-B4-C13; | A29-B4-C14; | A29-B4-C15; | A29-B4-C16; | A29-B4-C17; | A29-B4-C18; |
| A29-B4-C19; | A29-B4-C20; | A29-B4-C21; | A29-B4-C22; | A29-B4-C23; | A29-B4-C24; |
| A29-B4-C25; | A29-B4-C26; | A29-B4-C27; | A30-B4-C1; | A30-B4-C2; | A30-B4-C3; |
| A30-B4-C4; | A30-B4-C5; | A30-B4-C6; | A30-B4-C7; | A30-B4-C8 | A30-B4-C9; |
| A30-B4-C10; | A30-B4-C11; | A30-B4-C12; | A30-B4-C13; | A30-B4-C14; | A30-B4-C15; |
| A30-B4-C16; | A30-B4-C17; | A30-B4-C18; | A30-B4-C19; | A30-B4-C20; | A30-B4-C21; |
| A30-B4-C22; | A30-B4-C23; | A30-B4-C24; | A30-B4-C25; | A30-B4-C26; | A30-B4-C27; |
| A31-B4-C1; | A31-B4-C2; | A31-B4-C3; | A31-B4-C4; | A31-B4-C5; | A31-B4-C6; |
| A31-B4-C7; | A31-B4-C8; | A31-B4-C9; | A31-B4-C10; | A31-B4-C11; | A31-B4-C12; |
| A31-B4-C13; | A31-B4-C14; | A31-B4-C15; | A31-B4-C16; | A31-B4-C17; | A31-B4-C18; |
| A31-B4-C19; | A31-B4-C20; | A31-B4-C21; | A31-B4-C22; | A31-B4-C23; | A31-B4-C24; |
| A31-B4-C25; | A31-B4-C26; | A31-B4-C27; | A32-B4-C1; | A32-B4-C2; | A32-B4-C3; |
| A32-B4-C4; | A32-B4-C5; | A32-B4-C6; | A32-B4-C7; | A32-B4-C8; | A32-B4-C9; |
| A32-B4-C10; | A32-B4-C11; | A32-B4-C12; | A32-B4-C13; | A32-B4-C14; | A32-B4-C15; |
| A32-B4-C16; | A32-B4-C17; | A32-B4-C18; | A32-B4-C19; | A32-B4-C20; | A32-B4-C21; |
| A32-B4-C22; | A32-B4-C23; | A32-B4-C24; | A32-B4-C25; | A32-B4-C26; | A32-B4-C27; |
| A33-B4-C1; | A33-B4-C2; | A33-B4-C3; | A33-B4-C4; | A33-B4-C5; | A33-B4-C6; |
| A33-B4-C7; | A33-B4-C8; | A33-B4-C9; | A33-B4-C10; | A33-B4-C11; | A33-B4-C12; |
| A33-B4-C13; | A33-B4-C14; | A33-B4-C15; | A33-B4-C16; | A33-B4-C17; | A33-B4-C18; |
| A33-B4-C19; | A33-B4-C20; | A33-B4-C21; | A33-B4-C22; | A33-B4-C23; | A33-B4-C24; |
| A33-B4-C25; | A33-B4-C26; | A33-B4-C27; | A34-B4-C1; | A34-B4-C2; | A34-B4-C3; |
| A34-B4-C4; | A34-B4-C5; | A34-B4-C6; | A34-B4-C7; | A34-B4-C8; | A34-B4-C9 |
| A34-B4-C10; | A34-34-C11; | A34-B4-C12; | A34-B4-C13; | A34-B4-C14; | A34-B4-C15; |
| A34-B4-C16; | A34-B4-C17; | A34-B4-C18; | A34-B4-C19; | A34-B4-C20; | A34-B4-C21; |
| A34-B4-C22; | A34-B4-C23; | A34-B4-C24; | A34-B4-C25; | A34-B4-C26; | A34-B4-C27; |
| A35-B4-C1; | A35-B4-C2; | A35-B4-C3; | A35-B4-C4; | A35-B4-C5; | A35-B4-C6; |
| A35-B4-C7; | A35-B4-C8; | A35-B4-C9; | A35-B4-C10; | A35-B4-C11; | A35-B4-C12; |
| A35-B4-C13; | A35-B4-C14; | A35-B4-C15; | A35-B4-C16; | A35-B4-C17; | A35-B4-C18; |
| A35-B4-C19; | A35-B4-C20; | A35-B4-C21; | A35-B4-C22; | A35-B4-C23; | A35-B4-C24; |
| A35-B4-C25; | A35-B4-C26; | A35-B4-C27; | A36-B4-C1; | A36-B4-C2; | A36-B4-C3; |
| A36-B4-C4; | A36-B4-C5; | A36-B4-C6; | A36-B4-C7; | A36-B4-C8; | A36-B4-C9; |
| A36-B4-C10; | A36-B4-C11; | A36-B4-C12; | A36-B4-C13; | A36-B4-C14; | A36-B4-C15; |
| A36-B4-C16; | A36-B4-C17; | A36-B4-C18; | A36-B4-C19; | A36-B4-C20; | A36-B4-C21; |
| A36-B4-C22; | A36-B4-C23; | A36-B4-C24; | A36-B4-C25; | A36-B4-C26; | A36-B4-C27. |

Thus, for example, in the above list the compound denoted as A1-B1-C1 is the product of the combination of group A1 in Table 1 and B1 in Table 2 and C1 in Table 3, namely

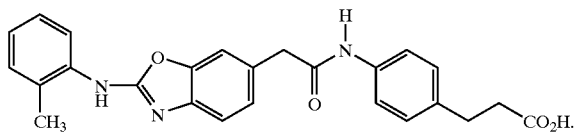

Preferred compounds of the invention are:

R) 3-{4-[2-(4-methoxy-2-o-tolylaminobenzoxazol-6-yl) acetylamino]phenyl}butanoic acid;

(R) 3-{4-[2-(4-methyl-2-o-tolylaminobenzoxazol-6-yl) acetylamino]phenyl}-butanoic acid;

(R,S) 3-phenyl-3-[4-(2-o-tolylamino-benzoxazol-6-yl)-acetylamino]-phenyl]-propanoic acid; and the corresponding N-oxides, and their prodrugs; and pharmaceutically acceptable salts and solvates (e.g. hydrates) of such compounds and their N-oxides and prodrugs.

The compounds of the invention exhibit useful pharmacological activity and accordingly are incorporated into pharmaceutical compositions and used in the treatment of patients suffering from certain medical disorders. The present invention thus provides, according to a further aspect, compounds of the invention and compositions containing compounds of the invention for use in therapy.

Compounds within the scope of the present invention block the interaction of the ligand VCAM-1 to its integrin receptor VLA-4 ($\alpha 4\beta 1$) according to tests described in the literature and described in vitro and in vivo procedures hereinafter, and which tests results are believed to correlate to pharmacological activity in humans and other mammals. Thus, in a further embodiment, the present invention provides compounds of the invention and compositions containing compounds of the invention for use in the treatment of a patient suffering from, or subject to, conditions which can be ameliorated by the administration of an inhibitor of $\alpha 4\beta 1$ mediated cell adhesion. For example, compounds of the present invention are useful in the treatment of inflammatory diseases, for example joint inflammation, including arthritis, rheumatoid arthritis and other arthritic conditions such as rheumatoid spondylitis, gouty arthritis, traumatic arthritis, rubella arthritis, psoriatic arthritis and osteoarthritis. Additionally, the compounds are useful in the treatment of acute synovitis, autoimmune diabetes, autoimmune encephalomyelitis, collitis, atherosclerosis, peripheral vascular disease, cardiovascular disease, multiple sclerosis, asthma, psoriasis restenosis, myocarditis, inflammatory bowel disease and melanoma cell division in metastasis.

A special embodiment of the therapeutic methods of the present invention is the treating of asthma.

Another special embodiment of the therapeutic methods of the present invention is the treating of joint inflammation.

Another special embodiment of the therapeutic methods of the present invention is the treating of inflammatory bowel disease.

According to a further feature of the invention there is provided a method for the treatment of a human or animal patient suffering from, or subject to, conditions which can be ameliorated by the administration of an inhibitor of the interaction of the ligand VCAM-1 to its integrin receptor VLA-4 ($\alpha 4\beta 1$), for example conditions as hereinbefore described, which comprises the administration to the patient of an effective amount of compound of the invention or a composition containing a compound of the invention. "Effective amount" is meant to describe an amount of compound of the present invention effective in inhibiting the interaction of the ligand VCAM-1 to its integrin receptor VLA-4 ($\alpha 4\beta 1$), and thus producing the desired therapeutic effect.

References herein to treatment should be understood to include prophylactic therapy as well as treatment of established conditions.

The present invention also includes within its scope pharmaceutical compositions comprising at least one of the compounds of the invention in association with a pharmaceutically acceptable carrier or excipient.

Compounds of the invention may be administered by any suitable means. In practice compounds of the present invention may generally be administered parenterally, topically, rectally, orally or by inhalation, especially by the oral route.

Compositions according to the invention may be prepared according to the customary methods, using one or more pharmaceutically acceptable adjuvants or excipients. The adjuvants comprise, inter alia, diluents, sterile aqueous media and the various non-toxic organic solvents. The compositions may be presented in the form of tablets, pills, granules, powders, aqueous solutions or suspensions, injectable solutions, elixirs or syrups, and can contain one or more agents chosen from the group comprising sweeteners, flavourings, colourings, or stabilisers in order to obtain pharmaceutically acceptable preparations. The choice of vehicle and the content of active substance in the vehicle are generally determined in accordance with the solubility and chemical properties of the active compound, the particular mode of administration and the provisions to be observed m pharmaceutical practice. For example, excipients such as lactose, sodium citrate, calcium carbonate, dicalcium phosphate and disintegrating agents such as starch, alginic acids and certain complex silicates combined with lubricants such as magnesium stearate, sodium lauryl sulphate and talc may be used for preparing tablets. To prepare a capsule, it is advantageous to use lactose and high molecular weight polyethylene glycols. When aqueous suspensions are used they can contain emulsifying agents or agents which facilitate suspension. Diluents such as sucrose, ethanol, polyethylene glycol, propylene glycol, glycerol and chloroform or mixtures thereof may also be used.

For parenteral administration, emulsions, suspensions or solutions of the products according to the invention in vegetable oil, for example sesame oil, groundnut oil or olive oil, or aqueous-organic solutions such as water and propylene glycol, injectable organic esters such as ethyl oleate, as well as sterile aqueous solutions of the pharmaceutically acceptable salts, are used. The solutions of the salts of the products according to the invention are especially useful for administration by intramuscular or subcutaneous injection. The aqueous solutions, also comprising solutions of the salts in pure distilled water, may be used for intravenous administration with the proviso that their pH is suitably adjusted, that they are judiciously buffered and rendered isotonic with a sufficient quantity of glucose or sodium chloride and that they are sterilised by heating, irradiation or microfiltration.

For topical administration, gels (water or alcohol based), creams or ointments containing compounds of the invention may be used. Compounds of the invention may also be incorporated in a gel or matrix base for application in a patch, which would allow a controlled release of compound through the transdermal barrier.

For administration by inhalation compounds of the invention may be dissolved or suspended in a suitable carrier for use in a nebuliser or a suspension or solution aerosol, or may be absorbed or adsorbed onto a suitable solid carrier for use in a dry powder inhaler.

Solid compositions for rectal administration include suppositories formulated in accordance with known methods and containing at least one compound of the invention.

The percentage of active ingredient in the compositions of the invention may be varied, it being necessary that it should constitute a proportion such that a suitable dosage shall be obtained. Obviously, several unit dosage forms may be administered at about the same time. The dose employed will be determined by the physician, and depends upon the desired therapeutic effect, the route of administration and the duration of the treatment, and the condition of the patient. In the adult, the doses are generally from about 0.001 to about 50, preferably about 0.001 to about 5, mg/kg body weight per day by inhalation, from about 0.01 to about 100, preferably 0.1 to 70, more especially 0.5 to 10, mg/kg body weight per day by oral administration, and from about 0.001 to about 10, preferably 0.01 to 1, mg/kg body weight per day by intravenous administration. In each particular case, the doses will be determined in accordance with the factors distinctive to the subject to be treated, such as age, weight, general state of health and other characteristics which can influence the efficacy of the medicinal product.

The compounds according to the invention may be administered as frequently as necessary in order to obtain the desired therapeutic effect. Some patients may respond rapidly to a higher or lower dose and may find much weaker maintenance doses adequate. For other patients, it may be necessary to have long-term treatments at the rate of 1 to 4 doses per day, in accordance with the physiological requirements of each particular patient. Generally, the active product may be administered orally 1 to 4 times per day. Of course, for some patients, it will be necessary to prescribe not more than one or two doses per day.

Compounds of the invention may be prepared by the application or adaptation of known methods, by which is meant methods used heretofore or described in the literature, for example those described by R. C. Larock in Comprehensive Organic Transformations, VCH publishers, 1989.

In the reactions described hereinafter it may be necessary to protect reactive functional groups, for example hydroxy, amino, imino, thio or carboxy groups, where these are desired in the final product, to avoid their unwanted participation in the reactions. Conventional protecting groups may be used in accordance with standard practice, for examples see T. W. Greene and P. G. M. Wuts in "Protective Groups in Organic Chemistry" John Wiley and Sons, 1991.

Compounds of formula (I) wherein Het, $R^1$, $R^2$, $L^1$, $L^2$ and $Z^1$ are as hereinbefore defined, and Y is carboxy may be prepared by hydrolysis of esters of formula (I) wherein Het, $R^1$, $R^2$, $L^1$, $L^2$ and $Z^1$ are as hereinbefore defined and where the Y is a —$CO_2R^{10}$ group (in which $R^{10}$ is alkyl, alkenyl or arylalkyl). The hydrolysis may conveniently be carried out by alkaline hydrolysis using a base, such as an alkali metal hydroxide, e.g. lithium hydroxide, or an alkali metal carbonate, e.g. potassium carbonate, in the presence of an aqueous/organic solvent mixture, using organic solvents such as dioxan, tetrahydrofuran or methanol, at a temperature from about ambient to about reflux. The hydrolysis of the esters may also be carried out by acid hydrolysis using an inorganic acid, such as hydrochloric acid, in the presence of an aqueous/inert organic solvent mixture, using organic solvents such as dioxan or tetrahydrofuran, at a temperature from about 50° C. to about 80° C.

As another example compounds of formula (I) wherein Het, $R^1$, $R^2$, $L^1$, $L^2$ and $Z^1$ are as hereinbefore defined, and Y is carboxy may be prepared by acid catalysed removal of the tert-butyl group of tert-butyl esters of formula (I) wherein Het, $R^1$, $R^2$, $L^1$, $L^2$ and $Z^1$ are as hereinbefore defined and Y is a —$CO_2R^{10}$ group (in which $R^{10}$ is tert-butyl), using standard reaction conditions, for example reaction with trifluoroacetic acid at a temperature at about room temperature.

As another example compounds of formula (I) wherein Het, $R^1$, $R^2$, $L^1$, $L^2$ and $Z^1$ are as hereinbefore defined and Y is carboxy may be prepared by hydrogenation of compounds of formula (I) wherein Het, $R^1$, $R^2$, $L^1$, $L^2$ and $Z^1$ are as hereinbefore defined and Y is a —$CO_2R^{10}$ group (in which $R^{10}$ is benzyl). The reaction may be carried out in the presence of ammonium formate and a suitable metal catalyst, e.g. palladium, supported on an inert carrier such as carbon, preferably in a solvent such as B methanol or ethanol and at a temperature at about reflux temperature. The reaction may alternatively be carried out in the presence of a suitable metal catalyst, e.g. platinum or palladium optionally supported on an inert carrier such as carbon, preferably in a solvent such as methanol or ethanol.

Esters of formula (I) wherein Het, $R^1$, $R^2$, $L^2$ and $Z^1$ are as hereinbefore defined $L^1$ is a —$R^3$—$R^4$— linkage (in which $R^3$ is as hereinbefore defined and $R^4$ is —C(=O)—$NR^5$—) and Y is a —$CO_2R^{10}$ group (in which $R^{10}$ is as hereinbefore defined) may be prepared by reaction of compounds of formula (II):

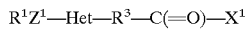

$R^1Z^1$—Het—$R^3$—C(=O)—$X^1$ (II)

wherein Het, $R^1$, $R^3$ and $Z^1$ are as hereinbefore and $X^1$ is a hydroxy group or a halogen, preferably chlorine, atom, with amines of formula (III):

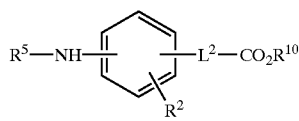

(III)

wherein $R^2$, $R^5$, $R^{10}$ and $L^2$ are as hereinbefore defined. When $X^1$ is a hydroxy group the reaction may be carried out using standard peptide coupling procedures for example coupling in the presence of O-(7-azabenzotriazol-1-yl)-1,1,3,3-tetramethyluronium hexafluorophosphate and triethylamine (or diisopropylethylamine) in tetrahydrofuran (or dimethylformamide), at room temperature. When $X^1$ is a halogen atom the acylation reaction may be carried out with the aid of a base, such pyridine, preferably in a solvent such as tetrahydrofuran and at a temperature at about room temperature.

Esters of formula (I) wherein Het, $R^1$, $R^2$, $L^2$ and $Z^1$ are as hereinbefore defined $L^1$ is a —$R^3$—$R^4$— linkage [in which $R^3$ is as hereinbefore defined, and $R^4$ is —$NR^5$—C(=O)— (where $R^5$ is as hereinbefore defined)] and Y is a —$CO_2R^{10}$ group (in which $R^{10}$ is as hereinbefore defined) may be prepared by reaction of compounds of formula (IV):

$R^1Z^1$—Het—$R^3$—$NHR^5$ (IV)

wherein Het, $R^1$, $R^3$, $R^5$ and $Z^1$ are as hereinbefore, with compounds of formula (V):

(V)

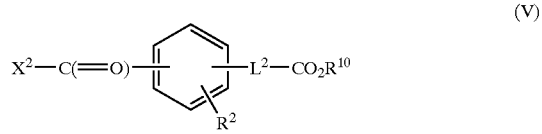

wherein $R^2$, $R^{10}$ and $L^2$ are as hereinbefore defined and $X^2$ is a hydroxy group or a halogen, preferably chlorine, atom, using procedures described hereinbefore for coupling acids or acid halides with amines.

Esters of formula (I) wherein Het, $R^1$, $R^2$, $L^2$ and $Z^1$ are as hereinbefore defined, $L^1$ is a —$R^3$—$R^4$—linkage (in which $R^3$ is as hereinbefore defined and $R^4$ is —O—) and Y is a —$CO_2R^{10}$ group (in which $R^{10}$ is as hereinbefore defined) may be prepared by reaction of compounds of formula (VI):

$R^1Z^1$—Het—$R^3$—OH (VI)

wherein Het, $R^1$, $R^3$ and $Z^1$ are as hereinbefore defined with compounds of formula (VII):

(VII)

wherein $R^2$, $R^{10}$ and $L^2$ are as hereinbefore defined and $Z^2$ is O, in the presence of a dialkyl azodicarboxylate, such as diethyl azodicarboxylate, and triphenylphosphine, preferably in a dry ethereal solvent, e.g. diethyl ether or tetrahydrofuran, preferably at or near room temperature.

Alternatively esters of formula (I) wherein Het, $R^1$, $R^2$, $L^2$ and $Z^1$ are as hereinbefore defined, $L^1$ is a —$R^3$—$R^4$— linkage (in which $R^3$ is as hereinbefore defined and $R^4$ is —O—) and Y is a —$CO_2R^{10}$ group (in which $R^{10}$ is as hereinbefore defined) may be prepared by alkylation of compounds of formula (VII), wherein $R^2$, $R^{10}$ and $L^2$ are as hereinbefore defined and $Z^2$ is O with the appropriate alkyl bromides of formula (VII):

$R^1Z^1$—Het—$R^3$—$X^3$ (VIII)

Het, $R^1$, $R^3$ and $Z^1$ are as hereinbefore defined and $X^3$ is a halogen, preferably bromo, atom using standard alkylation conditions. The alkylation may for example be carried out in the presence of a base, such as an alkali metal carbonate, e.g. potassium carbonate, or alkali metal hydride, e.g. sodium hydride, in dimethylformamide, or dimethyl sulphoxide, at a temperature from about 0° C. to about 100° C.

Esters of formula (I) wherein $R^1$, $R^2$, $L^2$ and $Z^1$ are as hereinbefore defined, $L^1$ is a —$R^3$—$R^4$— linkage (in which $R^3$ is as hereinbefore defined and $R^4$ is —S—) and Y is a —$CO_2R^{10}$ group (in which $R^{10}$ is as hereinbefore defined)

may be similarly prepared by alkylation-n of compounds of formula (VII) wherein $R^2$, $R^{10}$ and $L^2$ are as hereinbefore defined and $Z^2$ is S.

Esters of formula (I) wherein Het, $R^1$, $R^2$, $L^2$ and $Z^1$ are as hereinbefore defined, $L^1$ is a —$R^3$—$R^4$— linkage [in which $R^3$ is as hereinbefore defined and $R^4$ is —$NR^5$— (where $R^5$ is as hereinbefore defined)] and Y is a —$CO_2R^{10}$ group (in which $R^{10}$ is as hereinbefore defined) may be similarly prepared by alkylation of compounds of formula (III), wherein $R^2$, $R^5$, $R^{10}$ and $L^2$ are as hereinbefore defined.

Esters of formula (I) wherein Het, $R^1$, $R^2$, $L^2$ and $Z^1$ are as hereinbefore defined, $L^1$ is a —$R^3$—$R^4$— linkage [in which $R^3$ is as hereinbefore defined and $R^4$ is —C(=O)—] and Y is a —$CO_2R^{10}$ group (in which $R^{10}$ is as hereinbefore defined) may be prepared by reaction of esters of formula (IX):

$R^1Z^1$—Het—$R^3$—$CO_2R^{10}$ (IX)

wherein Het, $R^1$, $R^3$ and $Z^1$ are as hereinbefore defined and $R^{10}$ is lower alkyl, with Grignard reagents derived from reaction of compounds of formula (X):

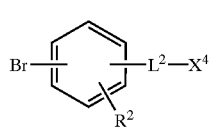

(X)

wherein $R^2$ and $L^2$ are as hereinbefore defined and $X^4$ is a suitably protected carboxylic acid group, with magnesium using standard reaction conditions, followed by removal of the carboxylic acid protecting group.

Esters of formula (I) wherein Het, $R^1$, $R^2$, $L^2$ and $Z^1$ are as hereinbefore defined, $L^1$ is a —$R^3$—$R^4$— linkage [in which $R^3$ is as hereinbefore defined and $R^4$ is —$NR^5$—C(=O)—NH— (where $R^5$ is as hereinbefore defined)] and Y is a —$CO_2R^{10}$ group (in which $R^{10}$ is as hereinbefore defined) may be prepared by reaction of compounds of formula (IV) wherein Het, $R^1$, $R^3$, $R^5$ and $Z^1$ are as hereinbefore defined, with isocyanates of formula (XI):

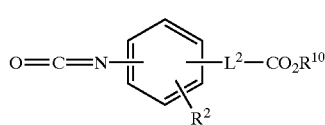

(XI)

wherein $R^2$, $R^{10}$ and $L^2$ are as hereinbefore defined. The reaction is preferably carried out with the aid of a base, such as a tertiary amine, for example triethylamine, preferably in a solvent such as dichloromethane, and at a temperature at about room temperature.

Esters of formula (I) wherein Het, $R^1$, $R^2$, $L^2$ and $Z^1$ are as hereinbefore defined, $L^1$ is a —$R^3$—$R^4$— linkage [in which $R^3$ is as hereinbefore defined and $R^4$ is —NH—C(=O)—$NR^5$— (where $R^5$ is as hereinbefore defined)] and Y is a —$CO_2R^{10}$ group (in which $R^{10}$ is as hereinbefore defined) may be similarly prepared by reaction of amines of formula (III) wherein $R^2$, $R^5$, $R^{10}$ and $L^2$ are as hereinbefore defined with compounds of formula (XII):

$R^1Z^1$—Het—$R^3$—N=C=O (XII)

wherein Het, $R^1$, $R^3$ and $Z^1$ are as hereinbefore defined.

Esters of formula (I) wherein Het, $R^1$, $R^2$, $L^2$ and $Z^1$ are as hereinbefore defined, $L^1$ is a —$R^3$—$R^4$— linkage [in which $R^3$ is as hereinbefore defined and $R^4$ is —$SO_2$—$NR^5$— (where $R^5$ is as hereinbefore defined)] and Y is a —$CO_2R^{10}$ group (in which $R^{10}$ is as hereinbefore defined) may be prepared by reaction of compounds of formula (XIII):

$R^1Z^1$—Het—$R^3$—$SO_2Cl$ (XIII)

wherein Het, $R^1$, $R^3$ and $Z^1$ are as hereinbefore defined, with amines of formula (III) wherein $R^2$, $R^5$, $R^{10}$ and $L^2$ are as hereinbefore defined. The reaction is preferably carried out with the aid of a base, such as a tertiary amine, for example triethylamine, preferably in a solvent such as tetrahydrofuran and at a temperature at about room temperature.

Esters of formula (I) wherein Het, $R^1$, $R^2$, $L^1$, $L^2$ and $Z^1$ are as hereinbefore defined, $L^1$ is a —$R^3$—$R^4$— linkage [in which $R^3$ is as hereinbefore defined and $R^4$ is —$NR^5$—$SO_2$— (where $R^5$ is as hereinbefore defined)] and Y is a —$CO_2R^{10}$ group (in which $R^{10}$ is as hereinbefore defined) may be similarly prepared by reaction of compounds of formula (IV) wherein Het, $R^1$, $R^3$, $R^5$ and $Z^1$ are as hereinbefore defined with sulphonyl chlorides of formula (XIV):

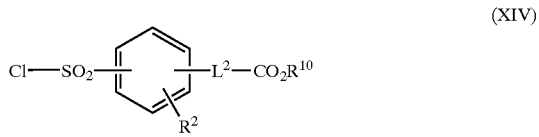

(XIV)

wherein $R^2$, $R^{10}$ and $L^2$ are as hereinbefore defined.

Esters of formula (I) wherein Het, $R^1$, $R^2$, $L^2$ and $Z^1$ are as hereinbefore defined, $L^1$ is a —$R^3$—$R^4$— linkage [in which $R^3$ is as hereinbefore defined and $R^4$ is —O—C(=O)—] and Y is a —$CO_2R^{10}$ group (where $R^{10}$ is as hereinbefore defined) may be prepared by O-acylation of compounds of formula (VI) wherein Het, $R^1$, $R^3$, and $Z^1$ are as hereinbefore defined with compounds of formula (V) wherein $R^2$, $R^{10}$ and $L^2$ are as hereinbefore defined and $X^2$ is a chlorine atom. The reaction may be carried using standard O-acylation conditions, for example reaction in the presence of a base, such as triethylamine or pyridine, at a temperature from about 0° C. to about room temperature.

Esters of formula (I) wherein Het, $R^1$, $R^2$, $L^2$ and $Z^1$ are as hereinbefore defined, $L^1$ is a —$R^3$—$R^4$— linkage [in which $R^3$ is as hereinbefore defined and $R^4$ is —C(=O)—O—] and Y is a —$CO_2R^{10}$ group (where $R^{10}$ is as hereinbefore defined) may be similarly prepared by O-acylation of compounds of formula (VII) wherein $R^2$, $R^{10}$ and $L^2$ are as hereinbefore defined and $Z^2$ is O with compounds of formula (II) wherein Het, $R^1$, $R^3$ and $Z^1$ are as hereinbefore defined and $X^1$ is a chlorine atom.

Esters of formula (I) wherein Het, $R^1$, $R^2$, $L^1$, $L^2$ and $Z^1$ are as hereinbefore defined, $L^1$ is a —$R^3$—$R^4$— linkage (in which $R^3$ is as hereinbefore defined and $R^4$ is —O—C(=O)—NH—) and Y is a —$CO_2R^{10}$ group (where $R^{10}$ is as hereinbefore defined) may be prepared by reaction of compounds of formula (VI) wherein Het, $R^1$, $R^3$ and $Z^1$ are as hereinbefore defined with isocyanates of formula (XI) wherein $R^2$, $R^{10}$ and $L^2$ are as hereinbefore defined The reaction is preferably carried out with the aid of a base, such as a tertiary amine, for example triethylamine, preferably in a solvent such as dichloromethane, and at a temperature at about room temperature.

Esters of formula (I) wherein Het, $R^1$, $R^2$, $L^1$, $L^2$ and $Z^1$ are as hereinbefore defined, $L^1$ is a —$R^3$—$R^4$— linkage (in which $R^3$ is as hereinbefore defined and $R^4$ is —NH—C(=O)—O—] and Y is a —$CO_2R^{10}$ group (where $R^{10}$ is as hereinbefore defined) may be similarly prepared by reaction of isocyanates of formula (XII) wherein Het, $R^1$, $R^3$ and $Z^1$ are as hereinbefore defined with compounds of formula (VII) wherein $R^2$, $R^{10}$ and $L^2$ are as hereinbefore defined and $Z^2$ is O.

Esters of formula (I) wherein Het, $R^1$, $R^2$, $L^2$ and $Z^1$ are as hereinbefore defined, $L^1$ is a —$R^3$—$R^4$— linkage (in which $R^3$ is a direct bond and $R^4$ is a straight or branched chain $C_{2-6}$alkenylene chain where the carbon-carbon double bond is directly attached to the phenyl ring containing the —$L^2$—Y group) may be prepared by reaction of compounds of formula (XV):

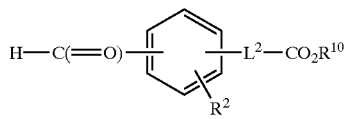
(XV)

wherein $R^2$, $R^{10}$ and $L^2$ are as hereinbefore defined, with an appropriate phosphorane (or phosphonate ester) of formula (XVI):

(XVI)

wherein Het, $R^1$ and $Z^1$ are as hereinbefore defined, $R^3$ is a straight or branched chain $C_{1-5}$alkylene chain and $X^5$ is =$PPh_3^+Br^-$ (or —$P(=O)(OEt)_2$), using standard Wittig (or Horner-Wadsworth-Emmons) coupling procedures (for example those described in Tetrahedron Organic Chemistry Series Volume 11, Organic Synthesis Based On Name Reactions and Unnamed reactions, Editors, J. E. Balwin and P. D. Magnus, pages 181 and 421).

Lactones of formula (I) wherein Het, $R^1$, $R^2$, $L^1$ and $Z^1$ are as hereinbefore defined and the moiety —$L^2$—Y is

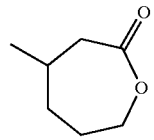

may be prepared by the selective reduction (using for example a borane derivative or lithium borohydride) of compounds of formula (I) wherein Het, $R^1$, $R^2$, $L^1$ and $Z^1$ are as hereinbefore defined and the moiety —$L^2$—Y is

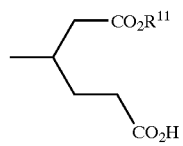

in which $R^{11}$ is lower alkyl, followed by spontaneous cyclisation of the intermediate hydroxy compound. The reduction can be achieved by the application or adaptation of the procedures described by C. J. Francis and J. Bryan Jones, J. Chem. Soc, Chem. Commun., 1984, (9), 579–58, J. Hiratake et al, J. Chem. Soc, Perkin Trans, 1987,1 (5), 1053–8 or L. K. P. Lam et al, J. Org. Chem. (1986), 51(11), 2047–50.

Lactones of formula (I) wherein Het, $R^1$, $R^2$, $L^1$ and $Z^1$ are as hereinbefore defined and the moiety —$L^2$—Y is

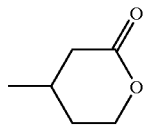

may be similarly prepared from compounds of formula (I) wherein Het, $R^1$, $R^2$, $L^1$ and $Z^1$ are as hereinbefore defined and the moiety —$L^2$—Y is

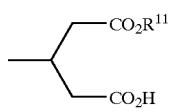

in which $R^{11}$ is lower alkyl.

Lactones of formula (I) wherein Het, $R^1$, $R^2$, $L^1$ and $Z^1$ are as hereinbefore defined and the moiety —$L^2$—Y is

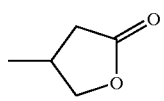

may be similarly prepared from compounds of formula (I) wherein Het, $R^1$, $R^2$, $L^1$ and $Z^1$ are as hereinbefore defined and the moiety —$L^2$—Y is

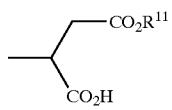

in which $R^{11}$ is lower alkyl.

Compounds of formula (I) wherein Het, $R^1$, $R^2$, $L^2$ and $Z^1$ are as hereinbefore defined, and Y is carboxy, represented by formula (XVII), may be prepared using resin technology as shown in scheme 1.

SCHEME 1

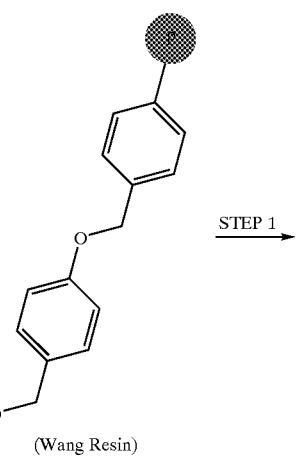

STEP 1

(Wang Resin)

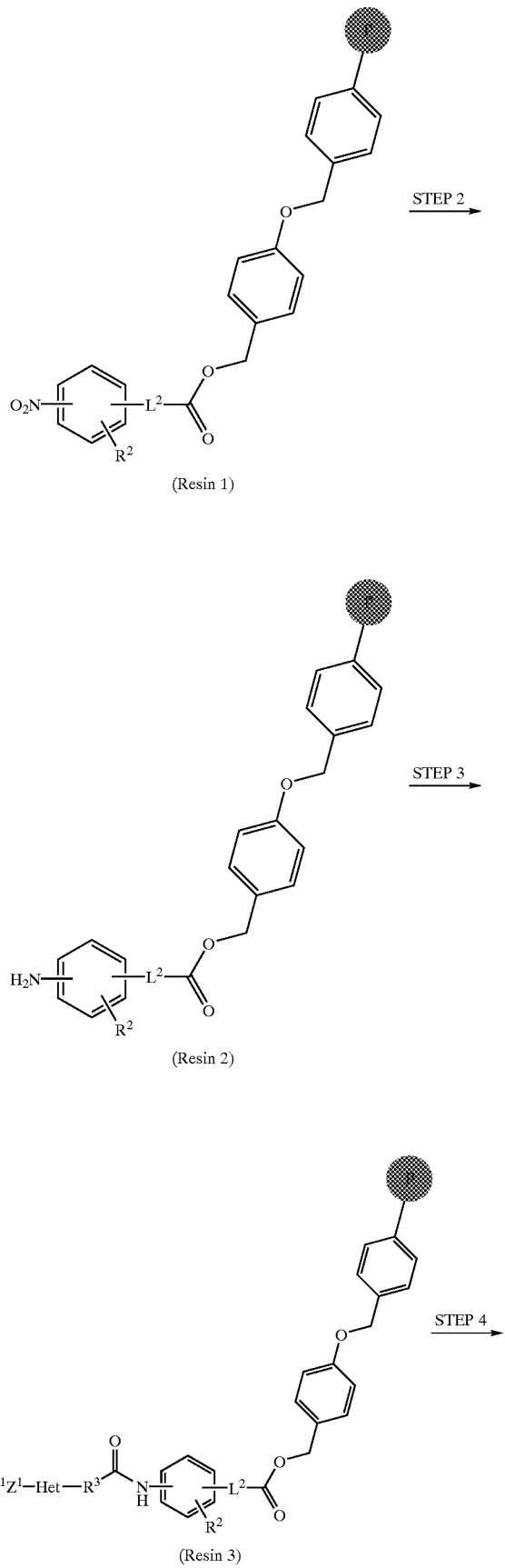

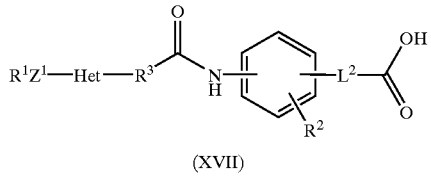

(XVII)

For example Wang resin, 4-hydroxymethylphenoxylated styrene/divinylbenzene copolymer, where represents the polymeric core (comprising polystyrene crosslinked with 1% to 2% divinylbenzene), may be treated, in Step 1, with acids of formula (XVIII):

(XVIII)

wherein $R^2$ and $L^2$ are as hereinbefore defined, with diisopropyl carbodiimide in dimethylformamide, in the presence of dimethylaminopyridine, at room temperature. The resulting esters (Resin 1), wherein $R^2$, $L^2$ and are as hereinbefore defined, may then treated, in Step 2, with tin chloride in dimethylformamide at room temperature to give Resin 2, wherein $R^2$, $L^2$ and are as hereinbefore defined. Resin 2 may then be coupled, in Step 3, with acids of general formula (II) wherein Het, $R^1$, $R^3$ and $Z^1$ are as hereinbefore and $X^1$ is hydroxy, in the presence of O-(7-azabenzotriazol-1-yl)-1,1,3,3-tetramethyluronium hexafluorophosphate and diisopropylethylamine in dimethylformamide, at room temperature. The resulting Resin 3, wherein Het, $R^1$, $R^2$, $R^3$, $L^2$, $Z^1$ and $R^2$, $L^2$ and are as hereinbefore defined, may then be treated, in Step 4, with trifluoroacetic acid in an inert solvent such as dichloromethane, at room temperature, to liberate the acids of general formula (XVII), wherein Het, $R^1$, $R^2$, $R^3$, $L^2$ and $Z^1$ are as hereinbefore defined.

Compounds of formula (Ia) wherein $R^1$, $R^2$, $R^3$, $R^{13}$ and $L^2$ are as hereinbefore defined, $R^5$ is hydrogen, X is O, $Z^1$ is NH and Y is carboxy, represented by formula (XVIIa), may be prepared using resin technology as shown in scheme 2.

SCHEME 2

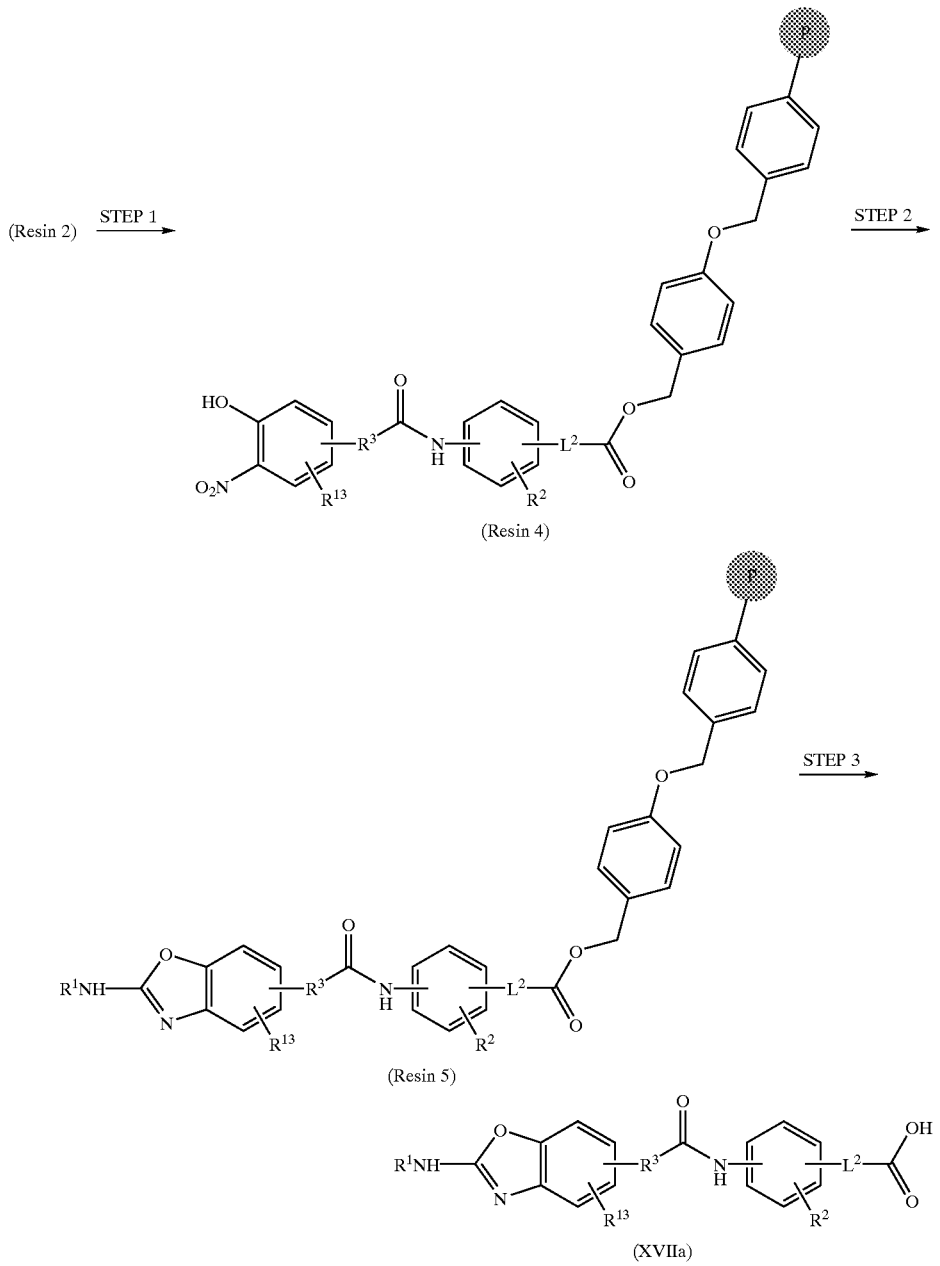

For example Resin 2 may be coupled, in Step 1, with acids of general formula (XXI) wherein $R^3$ and $R^{13}$ are as hereinbefore and X is O, in the presence of O-(7-azabenzotriazol-1-yl)-1,1,3,3-tetramethyluronium hexafluorophosphate and diisopropylethylamine in dimethylformamide, at room temperature to give Resin 4 wherein $R^2$, $R^3$, $L^2$ and

are as hereinbefore defined. Resin 4 may then be treated with tin chloride in dimethylformamide at room temperature followed treatment with isocyanates of formula $R^1$—N=C=O in dimethylformamide at room temperature and then treatment with diisopropylcarbodiimide in dimethylformamide at 75° C. The resulting Resin 5, wherein $R^1$, $R^2$, $R^3$, $L^2$ and

are as hereinbefore defined, may then be treated, in Step 3, with trifluoroacetic acid in an inert solvent such as dichloromethane, at room temperature, to liberate the acids of general formula (XVIIa), wherein $R^1$, $R^2$, $R^3$ and $L^2$ are as hereinbefore defined.

According to a further feature of the present invention, compounds of the invention may be prepared by interconversion of other compounds of the invention.

For example compounds of formula (I) wherein Het, $R^1$, $R^2$, $L^1$, $L^2$ and $Z^1$ are as hereinbefore defined and Y is —C(=O)—NHOH, may be prepared by reaction of compounds of formula (I) wherein Het, $R^1$, $R^2$, $L^1$, $L^2$ and $Z^1$ are as hereinbefore defined and Y is carboxy, with hydroxylamine using standard peptide coupling procedures such as treatment with a carbodiimide, for example dicyclohexylcarbodiimide, in the presence of triethylamine, in an inert solvent such as dichloromethane or tetrahydrofuran and at a temperature at about room temperature. The coupling may also be carried out using 1-hydroxybenzotriazole and 1-(3-dimethylaminopropyl)-3-ethylcarbodiimide in dichloromethane at room temperature. The preparation may also be carried out using an O-protected hydroxylamine such as O-(trimethylsilyl) hydroxylamine, O-(t-butyldimethylsilyl)-hydroxylamine, or O-(tetrahydropyranyl)hydroxylamine followed by treatment with acid.

As another example of the interconversion process, compounds of formula (J) wherein Het, $R^1$, $R^2$, $L^1$, $Z^1$ and Y are as hereinbefore defined and $L^2$ is an optionally substituted alkylene linkage, may be prepared by hydrogenation of the corresponding compounds of formula (I) in which $L^2$ is the corresponding optionally substituted alkenylene linkage. The hydrogenation may be carried out using hydrogen (optionally under pressure) in the presence of a suitable metal catalyst, e.g. platinum or palladium optionally supported on an inert carrier such as carbon, preferably in a solvent such as methanol or ethanol, and at a temperature at about room temperature.

As another example of the interconversion process, compounds of formula (I) wherein Het, $R^1$, $R^2$, $L^2$, $Z^1$ and Y are as hereinbefore described and $L^1$ is a —$R^3$—$R^4$— linkage where $R^3$ is a straight or branched chain $C_{2-6}$alkylene chain and $R^4$ is a direct bond, may be similarly prepared by hydrogenation of the corresponding compounds of formula (I) in which $L^1$ is a —$R^3$—$R^4$— linkage where $R^3$ is a straight or branched chain $C_{2-6}$alkenylene chain and $R^4$ is a direct bond.

As another example of the interconversion process, compounds of the invention containing a heterocyclic group wherein the hetero atom is a nitrogen atom may be oxidised to their corresponding N-oxides. The oxidation may conveniently be carried out by means of reaction with a mixture of hydrogen peroxide and an organic acid, e.g. acetic acid, preferably at or above room temperature, for example at a temperature of about 60–90° C. Alternatively, the oxidation may be carried out by reaction with a peracid, for example peracetic acid or m-chloroperoxybenzoic acid, in an inert solvent such as chloroform or dichloromethane, at a temperature from about room temperature to reflux, preferably at elevated temperature. The oxidation may alternatively be carried out by reaction with hydrogen peroxide in the presence of sodium tungstate at temperatures between room temperature and about 60° C.

It will be appreciated that compounds of the present invention may contain asymmetric centres. These asymmetric centres may independently be in either the R or S configuration. It will be apparent to those skilled in the art that certain compounds of the invention may also exhibit geometrical isomerism. IBM It is to be understood that the present invention includes individual geometrical isomers and stereoisomers and mixtures thereof, including racemic mixtures, of compounds of formula (I) hereinabove. Such isomers can be separated from their mixtures, by the application or adaptation of known methods, for example chromatographic techniques and recrystallisation techniques, or they are separately prepared from the appropriate isomers of their intermediates.

According to a further feature of the invention, acid addition salts of the compounds of this invention may be prepared by reaction of the free base with the appropriate acid, by the application or adaptation of known methods. For example, the acid addition salts of the compounds of this invention may be prepared either by dissolving the free base in water or aqueous alcohol solution or other suitable solvents containing the appropriate acid and isolating the salt by evaporating the solution, or by reacting the free base and acid in an organic solvent, in which case the salt separates directly or can be obtained by concentration of the solution.

The acid addition salts of the compounds of this invention can be regenerated from the salts by the application or adaptation of known methods. For example, parent compounds of the invention can be regenerated from their acid addition salts by treatment with an alkali, e.g. aqueous sodium bicarbonate solution or aqueous ammonia solution.

Compounds of this invention can be regenerated from their base addition salts by the application or adaptation of known methods. For example, parent compounds of the invention can be regenerated from their base addition salts by treatment with an acid, e.g. hydrochloric acid.

Compounds of the present invention may be conveniently prepared, or formed during the process of the invention, as solvates (e.g. hydrates). Hydrates of compounds of the present invention may be conveniently prepared by recrystallisation from an aqueous/organic solvent mixture, using organic solvents such as dioxan, tetrahydrofuran or methanol.

According to a further feature of the invention, base addition salts of the compounds of this invention may be prepared by reaction of the free acid with the appropriate base, by the application or adaptation of known methods. For example, the base addition salts of the compounds of this invention may be prepared either by dissolving the free acid in water or aqueous alcohol solution or other suitable solvents containing the appropriate base and isolating the salt by evaporating the solution, or by reacting the free acid and base in an organic solvent, in which case the salt separates directly or can be obtained by concentration of the solution.

The starting materials and intermediates may be prepared by the application or adaptation of known methods, for example methods as described in the Reference Examples or their obvious chemical equivalents.

Acids of formula (II) wherein Het is

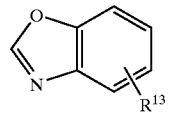

(in which $R^{13}$ is as hereinbefore defined), $R^1$ and $R^3$ are as hereinbefore defined, $Z^1$ is NH and $X^1$ is hydroxy may be prepared by reaction of compounds of formula (XIX):

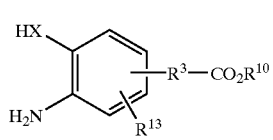

(XIX)

wherein $R^3$ and $R^{13}$ are as hereinbefore defined, $R^{10}$ is lower alkyl and X is O, with isocyanates of formula $R^1$—N=C=O in ethanol and at room temperature, followed by reaction with a carbodiimide, such as dicyclohexylcarbodiimide or diisopropylcarbodiimide in ethanol and at a temperature from about room temperature to about reflux temperature, and subsequent hydrolysis using standard conditions, for example those described hereinbefore.

Compounds of general formula (XIX) wherein $R^{13}$ is as hereinbefore defined, $R^3$ is an alkylene chain, X is O, and $R^{10}$ is lower alkyl may be prepared by the reduction of compounds of general formula (XX):

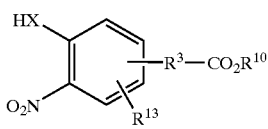

(XX)

wherein $R^{13}$ and $R^3$ are as hereinbefore defined, X is O, and $R^{10}$ is lower alkyl. The reduction may be carried out using standard methods, such as those described hereinbefore, for example hydrogenation in the presence of palladium. This method is particularly suitable for the preparation of compounds of formula (XIX) where $R^3$ is methylene and $R^{13}$ is lower alkoxy.

Compounds of general formula (XX) wherein $R^3$ and $R^{13}$ are as hereinbefore defined, X is O and $R^{10}$ is lower alkyl may be prepared by esterification of compounds of formula (XXI):

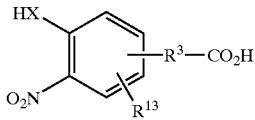

(XXI)

wherein $R^3$ and $R^{13}$ are as hereinbefore defined and X is O using standard methods as described hereinbefore, for example reaction with a lower alkyl alcohol (e.g. methanol) in the presence of a mineral acid, e.g. concentrated sulphuric acid.

Compounds of formula (XX) wherein $R^3$, $R^{10}$ and $R^{13}$ are as hereinbefore defined and X is O may also be prepared by reaction of compounds of formula (XXII):

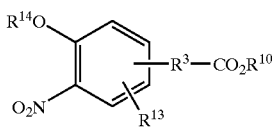

(XXII)

wherein $R^3$, $R^{10}$ and $R^{13}$ are as hereinbefore defined and $R^{14}$ is a suitable protecting group, such as alkyl- or arylcarbonyl, with a base, such as lithium hydroxide at a temperature at about room temperature. This method is particularly suitable for the preparation of compounds of formula (XX) where $R^3$ is methylene, $R^{13}$ is lower alkyl and $R^{10}$ is tertiary butyl.

Compounds of general formula (XXI) wherein $R^3$ and $R^{13}$ are as hereinbefore defined and X is O may be prepared by reaction of compounds of general formula (XXIII):

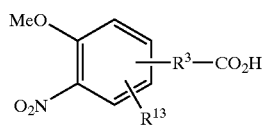

(XXIII)

wherein $R^3$ and $R^{13}$ are as hereinbefore defined by reaction with pyridine hydrochloride at a temperature at about room temperature.

Compounds of formula (XXII) wherein $R^3$, $R^{10}$ are as hereinbefore defined, $R^{13}$ is a lower alkyl group attached to the ring position adjacent to the nitro group and $R^{14}$ is a suitable protecting group, such as alkyl- or arylcarbonyl, may be prepared by reaction of compounds of formula (XXIV):

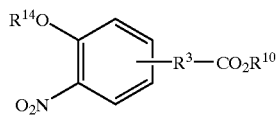

(XXIV)

wherein $R^3$, $R^{10}$ are as hereinbefore defined and $R^{14}$ is a suitable protecting group, such as alkyl- or arylcarbonyl, with a lower alkyl magnesium halide, such as methyl magnesium chloride, in an inert solvent, such as tetrahydrofuran, and at a temperature at about −15° C.

Compounds of general formula (XXIII) wherein $R^3$ is as hereinbefore defined and $R^{13}$ is a methoxy group which is attached at the ring position adjacent to the nitro group, may be prepared by the treatment of compounds of general formula (XXV):

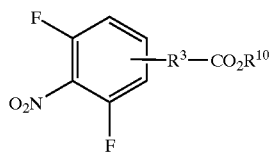

(XXV)

wherein $R^3$ and $R^{10}$ are as hereinbefore defined with sodium methoxide, followed by hydrolysis of the ester using standard conditions for example those described hereinbefore.

Acids of formula (II) wherein Het is

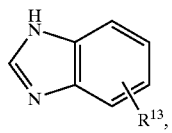

$R^1$, $R^3$ and $R^{13}$ are as hereinbefore defined, $Z^1$ is NH and $X^1$ is hydroxy may be similarly prepared from compounds of formula (XIX) wherein $R^3$, $R^{10}$ and $R^{13}$ are as hereinbefore defined and X is NH.

Acid chlorides of formula (II) wherein Het, $R^1$, $R^3$ and $Z^1$ are as hereinbefore defined and $X^1$ is a chlorine atom may be prepared from the corresponding acids of formula (II) wherein Het, $R^1$, $R^3$ and $Z^1$ are as hereinbefore defined and $X^1$ is hydroxy, by the application of standard procedures for the conversion of acids to acid chlorides for example by reaction with oxalyl chloride.

Compounds of formula (III) wherein $R^2$, $R^{10}$ and $L^2$ are as hereinbefore defined and $R^5$ is hydrogen may be prepared by reduction of the corresponding nitro compounds. The reduction may be carried IS out using iron powder and ammonium chloride, in aqueous ethanol at a temperature at about reflux. The reduction may also be carried out by hydrogenation using standard conditions, for example those described hereinbefore.

Compounds of formula (XIX) wherein $R^3$, $R^{10}$ and $R^{13}$ are as hereinbefore defined and X is NH may be similarly prepared by reduction of the corresponding nitro-amino compounds or dinitro compounds.

Compounds of formula (IV) wherein Het, $R^1$, $R^3$ and $Z^1$ are as hereinbefore defined and $R^5$ is hydrogen may be prepared by reaction of compounds of formula (VII) wherein Het, $R^1$, $R^3$ and $Z^1$ are as hereinbefore defined and $X^3$ is bromo with phthalimide potassium salt in dimethylformamide followed by reaction with hydrazine hydrate in ethanol (for example using the conditions described by O. Diouf et al., Heterocycles, 1995, 41, page 1219–1233).

Compounds of formula (IV) wherein Het, $R^1$, $R^3$ and $Z^1$ are as hereinbefore defined and $R^5$ is methyl may be prepared by treatment of the corresponding compounds of formula (IV) wherein Het, $R^1$, $R^3$ and $Z^1$ are as hereinbefore defined and $R^5$ is hydrogen with formic acetic anhydride followed by reduction with lithium aluminium hydride according to the procedure described by L. G. Humber et al, J. Med. Chem., 1971, 14, page 982.

Compounds of formula (VI) wherein Het, $R^1$ and $Z^1$ are as hereinbefore defined and $R^3$ is methylene, may be prepared by reduction of esters of formula (XXVI):

$$R^1Z^1\text{—Het—}R^{12}CO_2R^{10} \qquad (XXVI)$$

wherein Het, $R^1$ and $Z^1$ are as hereinbefore defined, $R^{10}$ is alkyl and $R^{12}$ is a direct bond. The reduction may conveniently be carried out with diisobutylaluminium hydride in an inert solvent, such as tetrahydrofuran, at a temperature from about −78° C. to about room temperature. The reduction may also be carried out with lithium aluminium hydride in an inert solvent, such as an ether, for example diethyl ether, at a temperature from about room temperature to about reflux.

Compounds of formula (VI) in which $R^3$ is a straight chain alkylene other than methylene may be similarly prepared esters of formula (XX) in which $R^{12}$ is the appropriate alkylene chain containing one carbon atom less than the alkylene chain in $R^3$ as just defined.

Compounds of formula (VIII) wherein Het, $R^1$ and $Z^1$ are as hereinbefore defined, $R^3$ is an alkylene chain and $X^3$ is bromo may be prepared by reaction of compounds of formula (VI) wherein Het, $R^1$ and $Z^1$ are as hereinbefore defined, $R^3$ is an alkylene chain with phosphorus tribromide in an inert solvent such as carbon tetrachloride and at a temperature at about room temperature.

Esters of formula (IX) wherein Het, $R^1$, $R^3$ and $Z^1$ are as hereinbefore defined and $R^{10}$ is lower alkyl may be prepared from the corresponding acids of formula (II) by standard esterification procedures for example reaction with a lower alkyl alcohol (e.g. methanol) in the presence of an acid catalyst, such as hydrogen chloride or sulphuric acid.

Esters of formula (XXVI) wherein Het, $R^1$, $R^{12}$ and $Z^1$ are as hereinbefore defined and $R^{10}$ is alkyl may be similarly prepared from the corresponding acids.

Compounds of formula (X) wherein $R^2$, $R^{10}$ and $L^2$ are as hereinbefore defined may be prepared from bromo-iodobenzene by the adaptation of procedures described by Y. Tamaru et al, Tetrahedron Letters, 1985, 26, page 5559 and 1986, 27, page 955.

Compounds of formula ($X^1$) wherein Het, $R^1$, $R^3$ and $Z^1$ are as hereinbefore defined may be prepared from compounds of formula (IV) wherein Het, $R^1$, $R^3$ and $Z^1$ are as hereinbefore defined and $R^5$ is hydrogen with phosgene following standard reaction conditions for the conversion of amines to isocyanates.

Compounds of formula (XIII) wherein Het, $R^1$, $R^3$ and $Z^1$ are as hereinbefore defined may be prepared by reaction of compounds of formula (VIII) wherein Het, $R^1$, $R^3$ and $Z^1$ are as hereinbefore defined and $X^3$ is a bromine atom with sodium sulphite then with phosphorus trichloride according to the procedure described by P. N. Culshaw and J. C. Walton, J. Chem. Soc., Perkin Trans II, 1991, 8, page 1201–1208.

Compounds of formula (XVI) wherein Het, $R^1$ and $Z^1$ are as hereinbefore defined, $R^3$ is a straight or branched chain $C_{1-5}$alkylene chain and $X^5$ is 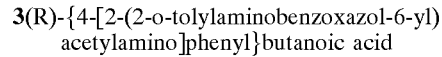 may be prepared by reaction of compounds of formula (VIII) wherein Het, $R^1$, $R^3$ and $Z^1$ are as hereinbefore defined and $X^3$ is a bromine atom by reaction with triphenylphosphine in an inert solvent and at a temperature from about room temperature to about reflux temperature of the solvent.

The present invention is further Exemplified but not limited by the following illustrative Examples and Reference Examples.

High Pressure Liquid Chromatography/Mass Spectrometry (LC-MS) conditions for determination of retention times ($R_T$) were as follows: 3 micron Luna C18 (2) HPLC column (30 mm×4.6 mm) operated under gradient elution conditions with mixtures of (A) water containing 0.1% formic acid and (B) acetonitrile containing 0.1% formic acid as the mobile phase gradient: 0.00 minutes, 95% A:5% B; 0.50 minutes, 95% A:5% B; 4.50 minutes, 5% A:95% B; 5.00 minutes, 5% A:95% B; 5.50 minutes, 95% A:5% B; flow rate 2 ml/minute with approximately 200 µl/minute split to the Mass Spectrometer; injection volume 10–40 µl; in line Diode Array (220–450 nm), in line Evaporative light scattering (ELS) detection ELS—temperature 50° C., Gain 8—1.8 ml/minute; Source temperature 150° C.

Accurate Mass spectra were recorded on a Brucker 3T Ion cylclotrom mass spectrometer.

EXAMPLE 1

3(R)-{4-[2-(2-o-tolylaminobenzoxazol-6-yl)acetylamino]phenyl}butanoic acid

A solution of 2-(o-tolylaminobenzoxazol-6-yl)acetic acid (1.0 g, Reference Example 4) in dimethylformamide (75 mL) was treated with O-(7-azabenzotriazol-1-yl)-1,1,3,3-tetramethyluronium hexafluorophosphate (1.35 g), then with diisopropylethylamine (1.2 mL) and then with ethyl (R)-3-(4-aminophenyl)butanoate (0.74 g, Reference Example 1). The mixture was kept at room temperature for an hour and then evaporated to low bulk. The residue was partitioned between hydrochloric acid (1M) and dichloromethane. The organic phase was washed with aqueous bicarbonate solution (5%) then with water, then dried, and then evaporated. The residue was suspended in ethanol (about 50 mL). The mixture was treated with aqueous sodium hydroxide (about 5 mL, 1M), then refluxed for 2 hours, then evaporated. The residue was triturated with aqueous hydrochloric acid (1M) then filtered. The insoluble material was washed with water, and then dried to give the title compound (0.48 g) as a white powder. MS: accurate mass=444.1936 (calculated 444.1923 MH$^+$). LC-MS: $R_T$=3.19 minutes (100% by ELSD); MS (ES$^+$), 444 (MH$^+$).

EXAMPLE 2

(R)-3-{4-[2-(2-o-tolylamino-3H-benzimidazol-5-yl)acetylamino]phenyl}butanoic acid dihydrate

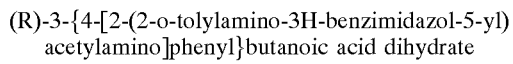

A solution of 2-(2-o-tolylamino)benzimidazole-5-acetic acid hydrochloride (200 mg, Reference Example 7), ethyl (R)-3-(4-aminophenyl)butanoate (147 mg, Reference Example 1) and O-(7-azabenzotriazol-1-yl)-1,1,3,3-tetramethyluronium hexafluorophosphate (300 mg) in dimethylformamide (5 mL) was treated with diisopropylethylamine (470 mg). After stirring at room temperature for 2 hours the reaction mixture was partitioned between ethyl acetate and dilute aqueous acetic acid. The layers were separated and the organic layer was washed with 5% aqueous sodium bicarbonate solution, then dried, and then evaporated. The yellow semi-solid residue (120 mg) was dissolved in ethanol (5 mL) and the solution was treated with aqueous lithium hydroxide solution (2 mL, 2M). After standing at room temperature for 2 hours the mixture was acidified by addition of dilute acetic acid. The resulting white solid was collected by filtration, and sucked dry in the filter funnel to give the title compound (42 mg) as a white amorphous solid. LC-MS: $R_T$=2.29 minutes (100% by ELSD); MS (ES$^+$), 443 (MH$^+$).

EXAMPLE 3

(R) 3-{4-[2-(4-methoxy-2-o-tolylaminobenzoxazol-6-yl)acetylamino]phenyl}butanoic acid A solution of ethyl (R) 3-{4-[2-(4-methoxy-2-o-tolylaminobenzoxazol-6-yl)acetylamino]phenyl}butanoate (0.17 g, Reference Example 8) in methanol was treated with aqueous lithium hydroxide solution (5 mL, 1M) and left to stand for five hours under argon. The mixture was acidified to pH 1 by addition of dilute hydrochloric acid, then partially evaporated, then diluted with more water and then partially evaporated again. The residue was diluted with water to afford a tan solid which was filtered, then dissolved in saturated sodium bicarbonate solution. The solution was washed with ethyl acetate, then acidified to pH1 and then extracted with ethyl acetate several times. The combined ethyl acetate extracts were washed with brine and then evaporated to give the title compound (0.12 g) as a white powder. LC-MS: $R_T$=3.29 minutes (100% by ELSD); MS (ES$^+$), 474 (MH$^+$).

EXAMPLE 4

(a) (R) 3-{4-[2-(4-Methyl-2-o-tolylaminobenzoxazol-6-yl)acetylamino]phenyl}-butanoic acid A solution of ethyl (R) 3-{4-[2-(4-methyl-2-o-tolylaminobenzoxazol-6-yl)acetylamino]phenyl}butanoate [0.14 g, Reference Example 15(a)] in methanol (2 mL) was treated with aqueous sodium hydroxide solution (1.2 mL, 1M) and then stirred at 50° C. for 2 hours. The mixture was diluted with water and partially evaporated. The residue was washed with diethyl ether and then acidified to pH 4. The precipitated solid was filtered and sucked dry to give the title compound (0.07 g) as a tan solid. LC-MS: $R_T$=3.38 minutes (100% by ELSD); MS (ES$^+$), 458 (MH$^+$).

(b) By proceeding in a manner similar to Example 4(a) but using ethyl (R) 3-{4-[2-(4-ethyl-2-o-tolylaminobenzoxazol-6-yl)acetylamino]phenyl}butanoate [Reference Example 15(b)] there was prepared (R)3-{4-[2-(4-ethyl-2-o-tolylaminobenzoxazol-6-yl)acetylamino]phenyl}butanoic acid. LC-MS: $R_T$=3.65 minutes (86% by ELSD); MS (ES$^+$), 472 (MH$^+$).

EXAMPLE 5

(R,S) 3-Phenyl-3-[4-(2-o-tolylamino-benzoxazol-6-yl)-acetylamino]-phenyl]-propanoic acid (R,S) Ethyl 3-(4-aminophenyl)-3-phenylpropanoate (620 mg, Reference Example 19) and diisopropylethylamine (0.8 mL) in dimethylformamide (10 mL) were treated with a solution of (2-o-tolylamino-benzoxazol-6-yl)-acetic acid (650 mg, Reference Example 4) and O-(7-azabenzotriazol-1-yl)-1,1,3,3-tetramethyluronium hexafluorophosphate (961 mg) in dimethylformamide (10 mL). The yellow solution was stirred at room temperature for 15 hours then evaporated. The residue was partitioned between ethyl acetate (50 mL) and 5% aqueous sodium carbonate (50 mL). The organic layer was separated and the aqueous phase extracted with ethyl acetate (50 mL). The combined organic phases were dried and then evaporated. The resulting yellow oil was subjected to flash chromatography on silica eluting with a mixture of ethyl acetate and pentane (1:1, v/v) to give a colourless gum. This material was dissolved in ethanol (20 mL) and the solution was treated with 5% aqueous sodium hydroxide (20 mL). The mixture was stirred at room temperature for 5 hours then concentrated to remove the ethanol. The residue was partitioned between ethyl acetate (50 mL) and hydrochloric acid (50 mL, 1M). After separation of the layers the ethyl acetate phase was washed with water (50 mL), then dried and then evaporated to give the title compound as an off white solid. LC-MS: $R_T$=3.48 minutes (>93% by ELSD); MS (ES$^+$), 505 (MH$^+$).

EXAMPLE 6

(R)-3-{4-[3-(2-o-tolylamino-benzoxazol-6-yl)-propanoylamino]-phenyl}-butanoic acid A solution of ethyl 3(R)-{4-(N-tertiary-butyloxycarbonylamino)phenyl}butanoate (104 mg, Reference Example 25) in a mixture of dichloromethane (5 mL) and trifluoroacetic acid (3 mL) was stirred at room temperature for 30 minutes then evaporated. The residue was dissolved in dimethylformamide (10 mL) and the solution was treated successively with diisopropylethylamine (240 mg), 3-(2-o-tolylamino-benzoxazol-6-yl)-propanoic acid (100 mg, Reference Example 20) and O-(7-azabenzotriazol-1-yl)-1,1,3,3-tetramethyluronium hexafluorophosphate (140 mg). The resulting mixture was kept at room temperature overnight, then partitioned between ethyl acetate (50 mL) and hydrochloric acid (50 mL, 1M). The layers were separated and the organic phase was washed with 5% sodium bicarbonate solution, then dried and then evaporated. The residue was dissolved in methanol (50 mL) and the solution was treated with sodium hydroxide solution (2 mL, 1M). This mixture was stirred at 40° C. for 2 hours then concentrated to low bulk, then diluted with water (30 mL) and then acidified with hydrochloric acid (5 mL, 1M). The resulting white precipitate was filtered, then washed with water and then dried to give the title compound (80 mg) as a white solid. LC-MS: $R_T$=3.28 minutes (100% by ELSD); MS (ES$^+$), 458 (MH$^+$).

EXAMPLE 7

6-Hydroxy-3-{4-[2-(2-o-tolylamino-benzoxazol-6-yl)-acetylamino]-phenyl}-hexanoic acid A solution of ethyl 6-hydroxy-3-{4-[2-(2-o-tolylamino-benzoxazol-6-yl)-acetylamino]-phenyl}-hexanoate [460 mg, Reference Example 23 (a)] in a mixture of ethanol (30 mL) and water (10 mL) was treated with sodium hydroxide solution (5mL, 1M) and then heated at 40° C. for 2 hours. The mixture was evaporated and the residue was dissolved in water (50 mL). This solution was washed three times with ethyl acetate, then acidified with dilute hydrochloric acid (a white precipitate was formed) and then extracted three times with ethyl acetate. The combined extracts were washed with brine, then dried and then evaporated. The residual white foam was dissolved in sodium hydroxide solution (50 mL, 0.5M) and the solution was washed twice with ether then acidified with dilute hydrochloric acid. The resulting white precipitate was filtered and then dried to give the title compound (250 mg) as a white solid. LC-MS: $R_T$=2.88 minutes (100% by ELSD); MS (ES$^+$), 488 (MH$^+$).

EXAMPLE 8

Lithium 6-Hydroxy-3-{4-[2-(2-o-tolylamino-3H-benzimidazol-5-yl)-acetylamino]-phenyl}-hexanoate trifluoroacetate A solution of ethyl 6-hydroxy-3-(4-{2-[2-o-tolylamino-3-(2-trimethylsilanyl-ethoxymethyl)-3H-benzimidazol-5-yl]-acetylamino}-phenyl)hexanoate (470 mg, Reference Example 23 (b)) in a mixture of ethanol (20 mL) and water (5 mL) was treated with lithium hydroxide monohydrate (65 mg). This solution was heated at 40° C. for 2 hours then evaporated. The residue was dissolved in water (20 mL) and this solution was washed twice with ether then acidified with dilute hydrochloric acid to give a colourless gum (370 mg). A portion of this material (50 mg) was treated. with trifluoroacetic acid (2 mL) and the mixture was stirred at room temperature for 2 hours then evaporated. The residue was dissolved in a mixture of ethanol (4 mL) and water (1 mL) and the solution was treated with lithium hydroxide monohydrate (8 mg). After stirring at room temperature for 90 minutes the mixture was filtered and the filtrate evaporated to dryness. The glassy residue was triturated with acetonitrile and the resultant solid was collected by filtration and dried to give the title compound (33 mg) as a white powder. LC-MS: $R_T$=2.11 minutes (87% by ELSD); MS (ES$^+$), 487 (MH$^+$).

Reference Example 1

Ethyl 3(R)-(4-aminophenyl)butanoate

A solution of ethyl 3(R)-(4-nitrophenyl)butanoate (4.0 g, Reference Example 2) in ethanol (100 mL) was treated with ammonium formate (about 15 g). The reaction mixture was immersed in an oil-bath in a single neck flask, the solution was heated to 50° C., then treated with palladium on charcoal (about 1 g, 5%) to give an immediate visible effervescence. The mixture was kept at 50° C. with stirring for about an hour, then filtered through filter-aid. The filtrate was evaporated and the residue was partitioned between tert-butyl methyl ether and water. The organic phase was dried then evaporated to give the title compound (2.8 g) as a light brown gum.

Reference Example 2

Ethyl 3(R)-(4-nitrophenyl)butanoate

A solution of 3(R)-(4-nitrophenyl)butanoic acid (4.0 g, Reference Example 3) in ethanol (60 mL) was treated with concentrated hydrochloric acid (5 drops). The solution was refluxed for 2 hours and then evaporated. The residue was dissolved in tert-butyl methyl ether and the solution was washed with 5% aqueous sodium carbonate solution, then dried, and then evaporated to give the title compound (4.0 g) as a white solid.

Reference Example 3

3(R)-(4-Nitrophenyl)butanoic acid (R)-3-phenylbutanoic acid (10.0 g) was added to concentrated sulphuric acid (40 mL) at −5° C. under nitrogen. The resulting thick gel-like mixture was stirred vigorously and fuming nitric acid (2.8 mL) was added slowly over 20 minutes. The reaction mixture was poured onto a mixture of ice and water (500 mL) and the resulting white precipitate was collected by filtration, then washed thoroughly with water, and then dried to give the title compound (10.1 g) as a white solid.

Reference Example 4

2-o-tolylaminobenzoxazole-6-acetic acid

A mixture of ethyl 4-amino-3-hydroxy-phenylacetate (3.3 g, Reference Example 5) and o-tolylisothiocyanate (2.5 mL) in ethanol (150 mL) was stirred at room temperature for about 2 hours. After standing at room temperature overnight the mixture was evaporated and the residue was subjected to flash chromatography (on silica eluting with a mixture of pentane and ethyl acetate, 7:3 v/v) to give a yellow foam. A solution of this material in ethanol (150 mL) was treated with dicyclohexylcarbodiimide (3.0 g) and the mixture was heated at reflux temperature for 2 hours. The mixture was evaporated and the residue subjected to short column chromatography (on silica eluting with a mixture of tert-butyl methyl ether and dichloromethane, 1:19 to 1:9 v/v). The resulting light yellow oil was dissolved in ethanol (100 mL) and the solution was treated with sodium hydroxide solution (15 mL, 1M) then heated at reflux temperature for 2 hours. The reaction mixture was evaporated and the residue was dissolved in water. The solution was washed with ethyl acetate and the aqueous layer was acidified to pH 1 by addition of concentrated hydrochloric acid. The resulting white precipitate was collected by filtration, then washed thoroughly with water, and then dried to give the title compound (1.8 g) as a white solid.

Reference Example 5

Ethyl 4-amino-3-hydroxy-phenylacetate

A solution of ethyl 3-hydroxy4-nitrophenylacetate (5.0 g, Reference Example 6) was dissolved in ethanol (approximately 200 mL) was treated with ammonium formate (approximately 20 g). The mixture was warmed to 50° C. and then treated cautiously with palladium on charcoal (approximately 1 g, 5%)—effervescence was observed. After 30 minutes the mixture was filtered hot through a pad of filter-aid and the filtrate was concentrated to give the title compound (3.3 g) as a black solid.

Reference Example 6

Ethyl 3-hydroxy-4-nitrophenylacetate

A solution of 3-hydroxy-4-nitrophenylacetic acid (4.0 g, prepared according to the procedure described by Meyer et al, J. Med. Chem., 1997, 40, pages 1049–1062) in ethanol (approximately 100 mL) was treated with concentrated hydrochloric acid (5–8 drops) was heated at reflux temperature for 3 hours then evaporated. The residue was dissolved in tert-butyl methyl ether and the solution was washed with saturated aqueous sodium bicarbonate solution, then with water, then dried, and then evaporated to give the title compound (5.0 g) as a light yellow solid.

Reference Example 7

2-(2-o-tolylamino)benzimidazole-5-acetic acid hydrochloride

A solution of ethyl 3,4-diaminophenylacetate (2.3 g, prepared according to the procedure described by Mederski et al, Biorg. Med. Chem. Left, 1998, 8, pages 17–22) in ethanol (20 mL) was treated with o-tolylisothiocyanate (3.0 g). After stirring at room temperature for 4 hours the solution was evaporated. The residue was dissolved in ethanol (50 mL) and the solution was treated with diisopropylcarbodiimide (3.0 g). After stirring at 50° C. for 4 hours the reaction mixture was evaporated. The residue was triturated with ether and filtered. The filtrate was evaporated and the residue was subjected to flash chromatography (on silica eluting with ether) to give a colourless gum (1.1 g). This material was dissolved in ethanol (15 mL) and the solution was treated with sodium hydroxide solution (5 mL, 1M). After standing at room temperature for 3 hours the clear solution was evaporated to low bulk and the residue partitioned between ethyl acetate and hydrochloric acid (1M). The aqueous phase was evaporated and the residue was triturated with ethanol. The filtrate was evaporated to give the title compound (0.8 g) as a beige foam.

Reference Example 8

Ethyl (R) 3-{4-[2-(4-methoxy-2-o-tolylaminobenzoxazol-6-yl)acetylamino]phenyl}butanoate A stirred solution of with ethyl (R) 3-(4-aminophenyl)butanoate (0.107 g, Reference Example 1) in dimethylformamide (10 mL) was treated with diisopropylethylamine (0.4 g), 2-(4-methoxy-2-o-tolylaminobenzoxazol-6-yl)acetic acid [0.105 g, Reference Example 9(a)] and then with O-(7-azabenzotriazol-1-yl)-1,1,3,3-tetramethyluronium hexafluorophosphate (0.14 g). The mixture was left to stand for 20 hours and then partitioned between ethyl acetate and hydrochloric acid (1M). The organic phase was washed with water, then with aqueous bicarbonate solution (5%), then with water, then with brine, then dried and then evaporated to give the title compound (0.17 g) as a cream coloured solid.

Reference Example 9

(a) 2-(4-Methoxy-2-o-tolylaminobenzoxazol-6-yl)acetic acid

A mixture of methyl 4-amino-3-hydroxy-5-methoxy-phenylacetate [0.295 g, Reference Example 10(a)] and o-tolylisothiocyanate (2.14 g) in ethanol (25 mL) was left at room temperature for 3 days. The mixture was evaporated and a solution of the residue in ethanol (20 mL) was treated with dicyclohexylcarbodiimide (0.308 g). The mixture was heated at reflux temperature for 2.5 hours and then evaporated. The resulting brown oil was dissolved in methanol (30 mL) and the solution was treated with sodium hydroxide solution (10 mL, 1M) and then heated at 45° C. for one hour. The mixtures was diluted with water and then partially evaporated. The residue was washed twice with diethyl ether and the pH of the aqueous phase was adjusted to 1–2 by addition of dilute hydrochloric acid. The mixture was then extracted with ethyl acetate and the organic phase was washed with water, then with brine, then dried and then evaporated to give the title compound (0.42 g) as a golden solid.
(b) By proceeding in a similar manner to Reference Example 9(a) but using t-butyl 4-amino-3-hydroxy-5-methyl-phenylacetate [Reference Example 10(b)] there was prepared 2-(4-methyl-2-o-tolylaminobenzoxazol-6-yl)acetic acid as a pale yellow solid.
(c) By proceeding in a manner similar to Reference Example 9(a) but using t-butyl 4-amino-3-hydroxy-5-ethyl-phenylacetate [Reference Example 10(c)] there was prepared 2-(4-ethyl-2-o-tolylaminobenzoxazol-6-yl)acetic acid.

Reference Example 10

(a) Methyl 4-amino-3-hydroxy-5-methoxy-phenylacetate

A solution of methyl 3-hydroxy-5-methoxy-4-nitrophenylacetate (0.34 g, Reference Example 11) in ethanol (25 mL) was treated with palladium on charcoal (approximately 0.035 g, 10%) and stirred under a hydrogen atmosphere. After 2 hours the mixture was filtered through a pad of celite and the filtrate was evaporated to give the title compound (0.3 g) as a brown oil.
(b) By proceeding in a manner similar to Reference Example 10(a) but using t-butyl 3-hydroxy-5-methyl-4-nitrophenylacetate [Reference Example 16(a)] there was prepared t-Butyl 4-amino-3-hydroxy-5-methyl-phenylacetate as a green oil.
(c) By proceeding in a manner similar to Reference Example 10(a) but using t-butyl 3-hydroxy-5-ethyl-4-nitrophenylacetate [Reference Example 16(a)] there was prepared t-butyl 4-amino-3-hydroxy-5-methyl-phenylacetate.

Reference Example 11

Methyl 3-hydroxy-5-methoxy-4-nitrophenylacetate

A solution of 3-hydroxy-5-methoxy-4-nitrophenylacetic acid (0.76 g, Reference Example 12) in methanol (100 mL) and concentrated hydrochloric acid (5 drops) was heated at reflux through 3A molecular sieve for 4 hours, then evaporated. The residue was partitioned between ethyl acetate and water. The organic phase was washed with water, then with brine, then dried and then evaporated. The residue was subjected to flash chromatography on silica eluting with dichloromethane, then with a mixture of methanol and dichloromethane (1:49, v/v) to give the title compound (0.34 g).

Reference Example 12

3-Hydroxy-5-methoxy4-nitrophenylacetic acid

A stirred mixture of 3,5-dimethoxy-4-nitrophenylacetic acid (0.4 g, Reference Example 13) and pyridine hydrochloride (6 g) was heated at 145° C., under argon, for 4 hours. The cooled reaction mixture was partitioned between ethyl acetate and water. The organic phase was washed with water, then with brine, then dried and then evaporated to give a 1:1 mixture of the title compound and starting material (0.37 g) which was used without further purification.

Reference Example 13

3,5-Dimethoxy-4-nitrophenylacetic acid

A stirred solution of t-butyl 3,5-difluoro-4-nitrophenylacetate (4.5 g, Reference Example 14) in methanol (350 mL) was treated with sodium methoxide in methanol (36 g, 25 wt %) and then heated at reflux for 18 hours. The cooled reaction mixture was carefully acidified to pH 2 by addition of dilute hydrochloric acid and then partially evaporated to remove the methanol. The aqueous residue was extracted twice with ethyl acetate. The combined extracts were extracted into saturated sodium bicarbonate solution. The aqueous extract was acidified to pH 2 and extracted with twice with ethyl acetate, then dried and then evaporated to give the title compound (1.4 g) as a brown solid.

Reference Example 14 t-Butyl 3,5-difluoro-4-nitrophenylacetate

A stirred solution of potassium t-butoxide (8.4 g) in dimethylformamide (150 mL), under nitrogen and at −10° to −12° C., was treated dropwise with a mixture of 2,6-difluoronitobenzene (5.0 g) and t-butyl chloroacetate (7.5 mL) in dimethylformamide (150 mL) over 30 minutes. After stirring for a further 1 hour the mixture was added to ice chilled hydrochloric acid (300 mL, 1M) and the mixture was extracted three times with pentane. The combined extracts were dried and then evaporated to give a brown oil which was subjected to flash chromatography on silica eluting with a mixture of dichloromethane and pentane mixture (1:1, v/v) to give the title compound (3.5 g) as a golden oil.

Reference Example 15

(a) Ethyl (R) 3-{4-[2-(4-methyl-2-o-tolylaminobenzoxazol-6-yl)acetylamino]phenyl}butanoate A stirred solution of 2-(4-methyl-2-o-tolylaminobenzoxazol-6-yl)acetic acid [0.1 g, Reference Example 9(b)] in dimethylformamide (3 mL) was treated with O-(7-azabenzotriazol-1-yl)-1,1,3,3-tetramethyluronium hexafluorophosphate (0.128 g), diisopropylethylamine (0.22 g) and after 5 minutes with ethyl (R) 3-(4-aminophenyl)butanoate (0.107 g, Reference Example 1). After 4 hours the reaction mixture was diluted with ethyl acetate and then washed with water, then with hydrochloric acid (1M), then twice with water, then with brine, then dried and then evaporated to give the title compound (0.15 g) as a brown oil.

(b) By proceeding in a manner similar to Reference Example 15(a) but using 2-(4-ethyl-2-o-tolylaminobenzoxazol-6-yl)acetic acid [Reference Example 9(c)] there was prepared ethyl (R) 3-{4-[2-(4-ethyl-2-o-tolylaminobenzoxazol-6-yl)acetylamino]phenyl}butanoate.

Reference Example 16

(a) t-Butyl 3-hydroxy-5-methyl-4-nitrophenylacetate

A solution of t-butyl 3-acetoxy-5-methyl-4-nitrophenylacetate [0.5 g, Reference Example 17(a)] in methanol (6 mL) was treated with lithium hydroxide (0.2 g) in water (1.5 mL). After stirring for 2 hours the mixture was carefully acidified to pH 5 and then treated with ethyl acetate and sodium chloride. The organic layer was evaporated and the residue was dissolved in dichloromethane. This solution was dried and then evaporated to give the title compound (0.45 g) as a yellow green oil.

(b) By proceeding in a manner similar to Reference Example 16(a) but using t-butyl 3-acetoxy-5-ethyl-4-nitrophenylacetate.

Reference Example 17

(a) t-Butyl 3-acetoxy-5-methyl-4-nitrophenylacetate

A stirred solution of t-butyl 3-acetoxy-4-nitrophenylacetate (8.0 g, Reference Example 18) in tetrahydrofuran (350 mL) at −15° C. under argon was treated dropwise with methyl magnesium chloride solution in diethyl ether (7 mL, 3M) and after 2 hours a further aliquot of methyl magnesium chloride solution in diethyl ether (7 mL, 3M). After stirring for a further 1 hour the reaction mixture was treated with 2,3-dichloro-5,6-dicyano-1,4-benzoquinone (10.4 g), then stirred at room temperature overnight, then partially evaporated and then treated with dichloromethane. The mixture was washed with water, then dried and then evaporated. The residue was subjected to flash chromatography on silica eluting with dichloromethane to give the title compound (1.66 g) as a yellow oil.

(b) By proceeding in a manner similar to Reference Example 17(a) but using ethyl magnesium chloride there was prepared t-butyl 3-acetoxy-5-ethyl-4-nitrophenylacetate.

Reference Example 18 t-Butyl 3-acetoxy-4-nitrophenylacetate

A stirred suspension of 3-acetoxy-4-nitrobenzoic acid (10.5 g) in dichloromethane (100 mL) was treated with oxalyl chloride (33 mL) and then dimethylformamide (2 drops). After stirring at room temperature over night the mixture was evaporated. The residue was dissolved in acetonitrile (100 mL) and this solution was added dropwise to a stirred mixture of trimethylsilyldiazomethane (25 mL, 2M in hexanes) and triethylamine (5.05 g) in acetonitrile (50 mL) at 0° C. under nitrogen and stirring at 0° C. was continued overnight. The mixture was evaporated and then partitioned between ethyl acetate and saturated sodium bicarbonate solution. The organic phase was dried and then evaporated. The residue was dissolved in refluxing t-butanol and then treated dropwise with a solution of silver benzoate (2.8 g) in triethylamine (15 mL) over 30 minutes. After standing for 30 minutes the cooled reaction mixture was evaporated and then partitioned between ethyl acetate and hydrochloric acid (1M). The organic phase was washed with saturated sodium bicarbonate solution, then dried and then evaporated to give the title compound (10.6 g) as a viscous brown oil.

Reference Example 19

(R,S) Ethyl 3-(4-aminophenyl)-3-phenylpropanoate

A solution of (E/Z) ethyl 3-(4-nitrophenyl)-cinnamate (1.82 g, prepared according to the procedure described by F. Himmelsbach et al in European Patent Application Number EP 612741 A1) in ethyl acetate (20 mL) was hydrogenated at 35° C. using 10% palladium on charcoal (200 mg) as catalyst. After 24 hours, the degassed mixture was filtered through a pad of diatomaceous earth and the filtrate was evaporated to dryness to give the title compound as an oil.

Reference Example 20

3-(2-o-tolylamino-benzoxazol-6-yl-propanoic acid

A solution of ethyl 3-(4-amino-3-hydroxyphenyl) propanoate (1.9 g, prepared according to the procedure described by T. Mase et al in World Patent Application Number 8605779 A1) in ethanol (50 mL) was treated with o-tolyl isothiocyanate (1.7 g). The mixture was warmed at about 40° C. for 2 hours and then evaporated. A solution of the residue in ethanol (50 mL) was treated with diisopropylcarbodiimide (3 mL) and the mixture was heated at about 40° C. for 1 hour and then evaporated. The residue was triturated with ether (50 mL) and the insoluble materials filtered. The filtrate was evaporated and the residue subjected to flash chromatography on silica eluting with a mixture of ethyl acetate and cyclohexane (2:3, v/v) to give a colourless oil (1.6 g) which was dissolved in methanol (50 mL). The methanol solution was treated with sodium hydroxide solution (5 mL, DIM). After stirring at 40° C. for 2 hours the mixture was evaporated to low bulk and the residue was partitioned between ethyl acetate (50 mL) and water (50 mL). The aqueous phase was treated with hydrochloric acid (10 mL, 1M) and the resulting white precipitate was filtered, then washed with water and then dried to give the title compound (1.1 g) as a white powder.

Reference Example 21

Ethyl 6-benzyloxy-3-{4-(N-tertiary-butyloxycarbonylamino)phenyl}-2-hexenoate and ethyl 6-benzyloxy-3-{4-(N-tertiary-butyloxycarbonylamino)phenyl}-3-hexenoate A mixture of N-tertiary-butyloxycarbonyl-4-iodoaniline (2.0 g), ethyl 6-benzyloxy-2-hexenoate (3.2 g, prepared according to the procedure described by D. Ma & J. Zhang, J. Chem. Soc., Perkin Trans. 1, 1999, pp1703 to 1708), palladium acetate (145 mg), tris (o-tolyl)phosphine (390 mg), and triethylamine (2.2 mL) in dimethylformamide (10 mL) was stirred in a sealed tube under a nitrogen atmosphere for 2 days. Further palladium acetate (50 mg), tris (o-tolyl) phosphine (100 mg), and N-tertiary-butyloxycarbonyl-4-iodoaniline (520 mg) were added and heating was continued for a further 18 hours. After cooling to room temperature the reaction mixture was poured into water and extracted three times with ether. The combined extracts were washed with dilute hydrochloric acid, then with brine, then dried over magnesium sulphate and then evaporated. The residual brown solid (6 g) was subjected to flash chromatography on silica eluting with a mixture of ethyl acetate and petroleum ether (1:9, v/v) to give in order of elution: ethyl 6-benzyloxy-2-hexenoate as a colourless oil; ethyl 6-benzyloxy-3-{4-(N-tertiary-butyloxycarbonylamino) phenyl}-2-hexenoate (730 mg) as a yellow oil; and ethyl 6-benzyloxy-3-{4-(N-tertiary-butyloxycarbonylamino) phenyl}-3-hexenoate (2.1 g) as an oily solid. The latter oily solid was triturated with ether and the mixture was filtered. The filtrate was evaporated to give the title compound (1.6 g) as a yellow oil.

Reference Example 22

(a) Ethyl 6-benzyloxy-3-{4-[2-(2-o-tolylamino-benzoxazol-6-yl)-acetylamino]-phenyl}-3-hexenoate A solution of ethyl 6-benzyloxy-3-{4-(N-tertiary-butyloxycarbonylamino)phenyl}-3-hexenoate (580 mg, Reference Example 21) in a mixture of trifluoroacetic acid (10 mL) and dichloromethane (15 mL) was kept at room temperature for 90 minutes and then evaporated. The residue was dissolved in dimethylformamide and the solution was treated successively with O-(7-azabenzotriazol-1-yl)-1,1,3,3-tetramethyluronium hexafluorophosphate (500 mg), 2-(o-tolylaminobenzoxazol-6-yl)acetic acid (380 mg, Reference Example 4) and diisopropylethylamine (1.2 mL). This mixture was kept at room temperature for 2 hours then poured onto dilute hydrochloric acid and then extracted three times with ethyl acetate. The combined organic extracts were washed with brine, then dried and then evaporated. The residue was subjected to flash chromatography on silica eluting with a mixture of ethyl acetate and petroleum ether mixture (2:3, v/v) to give the title compound (680 mg) as a light yellow oil.

(b) By proceeding in a manner similar to Reference Example 22(a) but using [2-o-tolylamino-3-(2-trimethylsilanyl-ethoxymethyl)-3H-benzimidazol-5-yl]-acetic acid (Reference Example 24) there was prepared ethyl 6-benzyloxy-3-(4-{2-[2-o-tolylamino-3-(2-trimethysilanyl-ethoxymethyl)-3H-benzimidazol-5-yl]-acetylamino}-phenyl)-3-hexenoate.

Reference Example 23

(a) Ethyl 6-hydroxy-3-{4-[2-(2-o-tolylamino-benzoxazol-6-yl)-acetylamino]-phenyl}-hexanoate A mixture of ethyl 6-benzyloxy-3-{4-[2-(2-o-tolylamino-benzoxazol-6-yl)-acetylamino]-phenyl}-3-hexenoate (640 mg, Reference Example 22(a)) and 10% palladium on charcoal (250 mg) in ethanol (50 mL) was hydrogenated at room temperature and pressure. After 24 hours further catalyst (200 mg) was added and the mixture again subjected to a hydrogen atmosphere for a further 24 hours. The mixture was filtered through filter-aid and the filtrate evaporated to dryness to give the title compound (460 mg) as a colourless oil.

(b) By proceeding in a manner similar to Reference Example 23(a) but using ethyl 6-benzyloxy-3-(4-{2-[2-o-tolylamino-3-(2-trimethylsilanyl-ethoxymethyl)-3H-benzimidazol-5-yl]-acetylamino}-phenyl)-3-hexenoate (Reference Example 22(b)) there was prepared ethyl 6-hydroxy-3-(4-{2-[2-o-tolylamino-3-(2-trimethylsilanyl-ethoxymethyl)-3H-benzimidazol-5-yl]-acetylamino}-phenyl)hexanoate Reference Example 24

[2-o-tolylamino-3-(2-trimethylsilanyl-ethoxymethyl)-3H-benzimidazol-5-yl]-acetic acid A solution of ethyl 3,4-diaminophenylacetate (5.8 g, prepared according to the procedure described by Mederski et al, Biorg. Med. Chem. Lett, 1998, 8, pages 17–22) in ethanol (40 mL) was treated with o-tolylisothiocyanate (4.9 g). After stirring at room temperature for 4 hours the solution was evaporated. A stirred solution of the residue in ethanol (100 mL) was treated with diisopropylcarbodiimide (7.6 g), then heated at reflux temperature for 6 hours and then evaporated. The residue was subjected to flash chromatography on silica eluting with ether to give a yellow gum (5.2 g). A solution of this product (5.0 g) in tetrahydrofuran (200 mL) was treated with sodium hydride (710 mg of a 60% suspension in oil) under a nitrogen atmosphere and after stirring at room temperature for 30 minutes this mixture was treated with 2-trimethylsilanyl-ethoxymethyl chloride (2.95 g). After stirring at room temperature for a further 1 hour the mixture was evaporated to low bulk and the residue was partitioned between ethyl acetate (500 mL) and water (500 mL). The organic phase was dried and then evaporated. The residue was subjected to flash chromatography on silica eluting with a mixture of pentane and ether (3:2, v/v) then with ether to give a white foam (5.2 g). This material was dissolved in methanol (100 mL) and the solution was treated with sodium hydroxide solution (30 mL, 1M). After standing at room temperature for 4 hours the clear solution was evaporated to low bulk and then treated with water (50 mL). The mixture was acidified with acetic acid to give a white gummy precipitate. After careful decantation of the supernatant liquors the gum was dissolved in the minimum of ethanol. After standing for some time a white precipitate formed. The precipitate was collected by filtration and then dried to give the title compound (0.9 g) as a white powder.

Reference Example 25

Ethyl 3(R)-{4-(N-tertiary-butyloxycarbonylamino) phenyl}butanoate

A stirred solution of ethyl 3(R)-(4-aminophenyl) butanoate (10 g, Reference Example 1) in tetrahydrofuran (100 mL) was treated with tertiary-butyloxycarbonyl anhydride (12.6 g) and then heated at reflux temperature for 5 hours. The reaction mixture was evaporated and the residue was subjected to flash chromatography on silica eluting with a mixture of ether and pentane mixture (1:4, v/v) to give the title compound (10 g) as a colourless oil which slowly crystallised on standing.

In Vitro and in Vivo Test Procedures

1. Inhibitory Effects of Compounds on VLA4 Dependent Cell Adhesion to Fibronectin and VCAM 1.1 Metabolic Labelling of RAMOS Cells RAMOS cells (a pre-B cell line from ECACC, Porton Down, UK) are cultured in RPMI culture medium (Gibco, UK) supplemented with 5% foetal calf serum (FCS, Gibco, UK). Prior to assay the cells are suspended at a concentration of $0.5 \times 10^6$ cells/ml RPMI and labelled with 400 $\mu$Ci/ 100 mls of [$^3$H]-methionine (Amersham, UK) for 18 hours at 37° C.

1.2 96 Well Plate Preparation for Adhesion Assay

Cytostar plates (Amersham, UK) were coated with 50 μl/well of either 3 μg/ml human soluble VCAM-1 (R&D Systems Ltd, UK) or 28.8 μg/ml human tissue Fibronectin (Sigma, UK). In control non-specific binding wells 50 μl phosphate buffered saline was added. The plates were then left to dry in an incubator at 25° C., overnight. The next day the plates were blocked with 200 μl/well of Pucks buffer (Gibco, UK) supplemented with 1% BSA (Sigma, UK). The plates were left at room temperature in the dark for 2 hours. The blocking buffer was then disposed of and the plates dried by inverting the plate and gently tapping it on a paper tissue. 50 μl/well of 3.6% dimethyl sulphoxide in Pucks buffer supplemented with 5 mM manganese chloride (to activate the integrin receptor Sigma, UK) and 0.2% BSA (Sigma, UK), was added to the appropriate control test binding and non-specific binding assay wells in the plate. 50 μl/well of the test compounds at the appropriate concentrations diluted in 3.6% dimethyl sulphoxide in Pucks buffer supplemented with 5 mM manganese chloride and 0.2% BSA, was added to the test wells.

Metabolically labelled cells were suspended at $4 \times 10^6$ cells/ml in Pucks buffer that was supplemented with manganese chloride and BSA as above. 50 μl/well of cells in 3.6% dimethyl sulphoxide in Pucks buffer and supplements was added to all plate wells.

The same procedure exists for plates coated with either VCAM-1 or fibronectin and data is determined for compound inhibition of cell binding to both substrates.

1.3 Performance of Assay and Data Analysis

The plates containing cells in control or compound test wells are incubated in the dark at room temperature for 1 hour.

The plates are then counted on a Wallac Microbeta scintillation counter (Wallac, UK) and the captured data processed in Microsoft Excel (Microsoft, US). The data was expressed as an IC50, namely the concentration of inhibitor at which 50% of control binding occurs. The percentage binding is determined from the equation:

$$\{[(C_{TB}-C_{NS})-(C_I-C_{NS})]/(C_{TB}-C_{NS})\} \times 100 = \% \text{ binding}$$

where $C_{TB}$ are the counts bound to fibronectin (or VCAM-1) coated wells without inhibitor present, $C_{NS}$ are the counts present in wells without substrate, and $C_I$ are the counts present in wells containing a cell adhesion inhibitor.

Compound data of this invention is expressed for $IC_{50}$s for inhibition of cell adhesion to both fibronectin and VCAM-1. Particular compounds of the invention inhibit cell adhesion to fibronectin and VCAM-1 with $IC_{50}$'s in the range 100 micromolar to 1 nanomolar. Preferred compounds of the invention inhibit cell adhesion to fibronectin and VCAM-1 with $IC_{50}$'s in the range 10 nanomolar to 1 nanomolar.

2. Inhibition of Antigen-induced Airway Inflammation in the Mouse and Rat

2.1 Sensitization of the Animals

Rats (Brown Norway, Harland Olac, UK) are sensitized on days 0, 12 and 21 with ovalbumin (100 μg, intraperitoneally [i.p], Sigma, UK) administered with aluminium hydroxide adjuvant (100 mg, i.p., Sigma, UK) in saline (1 ml, i.p.).

In addition mice (C57) are sensitized on days 0 and 12 with ovalbumin (10 μg, i.p.) administered with aluminium hydroxide adjuvant (20 mg, i.p.) in saline (0.2 ml, i.p.).

2.2 Antigen Challenge

Rats are challenged on any one day between days 28–38, while mice are challenged on any one day between days 20–30.

The animals are challenged by exposure for 30 minutes (rats) or 1 hour (mice) to an aerosol of ovalbumin (10 g/l) generated by an ultrasonic nebulizer (deVilbiss Ultraneb, US) and passed into an exposure chamber.

2.3 Treatment Protocols

Animals are treated as required before or after antigen challenge. The aqueous-soluble compounds of this invention can be prepared in water (for oral, p.o. dosing) or saline (for intratracheal, i.t. dosing). Non-soluble compounds are prepared as suspensions by grinding and sonicating the solid in 0.5% methyl cellulose/0.2% polysorbate 80 in water (for p.o. dosing, both Merck UK Ltd., UK) or saline (for i.t. dosing). Dose volumes are: for rats 1 ml/kg, p.o. or 0.5 mg/kg, i.t.; for mice 10 ml/kg, p.o. or 1 ml/kg,i.t.

2.4 Assessment of Airway Inflammation

The cell accumulation in the lung is assessed 24 hours after challenge (rats) or 48–72 hours after challenge (mice). The animals are euthanized with sodium pentobarbitone (200 mg/kg, i.p., Pasteur Merieux, France) and the trachea is immediately cannulated. Cells are recovered from the airway lumen by bronchoalveolar lavage (BAL) and from the lung tissue by enzymatic (collagenase, Sigma, UK) disaggregation as follows.

BAL is performed by flushing the airways with 2 aliquots (each 10 ml/kg) RPMI 1640 medium (Gibco, UK) containing 10% fetal calf serum (FCS, Serotec Ltd., UK). The recovered BAL aliquots are pooled and cell counts made as described below.

Immediately after BAL, the lung vasculature is flushed with RPMI 1640/FCS to remove the blood pool of cells. The lung lobes are removed and cut into 0.5 mm pieces. Samples (rats: 400 mg; mice: 150 mg) of homogenous lung tissue are incubated in RPMI 1640/FCS with collagenase (20 U/ml for 2 hours, then 60 U/ml for 1 hour, 37° C.) to disaggregate cells from the tissue. Recovered cells are washed in RPMI 1640/FCS.

Counts of total leukocytes recovered from the airway lumen and the lung tissue are made with an automated cell counter (Cobas Argos, US). Differential counts of eosinophils, neutrophils and mononuclear cells are made by light microscopy of cytocentrifuge preparations stained with Wright-Giemza stain (Sigma, UK). T cells are counted by flow cytometry (EPICS XL, Coulter Electronics, US) using fluophore-labelled antibodies against CD2 (a pan-T cell marker used to quantify total T cells), CD4, CD8 and CD25 (a marker of activated T cells). All antibodies were supplied by Serotec Ltd., UK)

2.5 Data Analysis

The cell data was expressed as mean cell numbers in unchallenged, challenged and vehicle treated, and challenged and compound treated groups, including the standard error of the means. Statistical analysis of the difference among treatment groups was evaluated using one-way analysis of variance via the Mann-Whitney test. Where $p < 0.05$ no statistical significance existed.

What is claimed is:

1. A compound of formula (Ia):

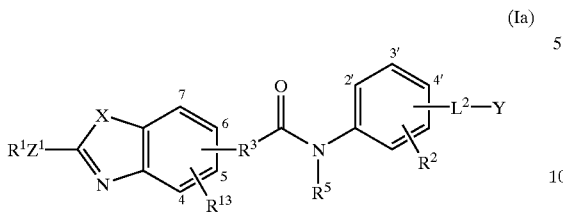

wherein:
- $R^1$ represents optionally substituted aryl;
- $R^2$ represents hydrogen, halogen, $C_{1-4}$ alkyl or $C_{1-4}$ alkoxy;
- $R^3$ is an alkylene chain, an alkenylene chain or an alkynylene chain;
- $R^5$ represents hydrogen or $C_{1-4}$ alkyl;
- $R^{13}$ is selected from acyl, acylamino, alkoxy, alkoxycarbonyl, alkylenedioxy, alkylsulphinyl, alkylsulphonyl, alkylthio, aroyl, aroylamino, aryl, arylalkyloxy, arylalkyloxycarbonyl, arylalkylthio, aryloxy, aryloxycarbonyl, arylsulphinyl, arylsulphonyl, arylthio, carboxy, cyano, halo, hydrogen, hydroxy, nitro, trifluoromethyl, $Y^1Y^2N-$, $Y^1Y^2NCO-$, $Y^1Y^2NSO_2-$, $Y^1Y^2N-C_{2-6}$ alkylene-$Z^1-$, alkylC(=O)-$Y^1N-$, alkylSO$_2-$ $Y^1N-$ or alkyl optionally substituted with aryl, hydroxy, or $Y^1Y^2N-$;
- $L^2$ represents an alkylene or alkenylene linkage each optionally substituted by $R^6$ (where $R^6$ represents alkyl, alkenyl, alkynyl, aryl, arylalkyl, arylalkenyl, arylalkynyl, cycloalkyl, cycloalkylalkyl, cycloalkylalkenyl, cycloalkylalkynyl, cycloalkenyl or cycloalkenylalkyl) or by alkyl substituted by hydroxy, $-OR^6$, $-O-C(=O)-R^6$ or $-NY^1Y^2$;
- $Y^1$ and $Y^2$ are independently hydrogen, alkenyl, alkyl, aryl, arylalkyl or cycloalkyl;
- X is O;
- Y is carboxy; and
- $Z^1$ represents $NR^5$;
- and the corresponding N-oxides, and their prodrugs; and pharmaceutically acceptable salts and solvates k of such compounds and their N-oxides and prodrugs.

2. A compound according to claim 1 in which $R^1$ represents optionally substituted phenyl.

3. A compound according to claim 1 in which $Z^1$ represents NH.

4. A compound according to claim 1 in which $R^{13}$ represents hydrogen, $C_{1-4}$ alkyl or $C_{1-4}$ alkoxy.

5. A compound according to claim 1 in which $R^3$ represents methylene.

6. A compound according to claim 1 in which $R^5$ represents hydrogen.

7. A compound according to a claim 1 in which $R^2$ represents hydrogen.

8. A compound according to claim 1 in which $L^2$ represents a $C_{1-4}$ alkylene linkage optionally substituted by $C_{1-4}$ alkyl, optionally substituted phenyl, or by alkyl substituted by hydroxy, $-OR^6$, $-O-C(=O)-R^6$ or $-NY^1Y^2$.

9. A compound according to claim 1 in which $L^2$ represents ethylene optionally substituted by $C_{1-4}$ alkyl, optionally substituted phenyl, or by alkyl substituted by hydroxy, $-OR^6$, $-O-C(=O)-R^6$ or $-NY^1Y^2$.

10. A compound according to claim 1 in which $L^2$ represents

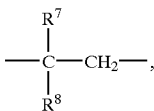

where $R^7$ and $R^8$ are both independently hydrogen or $C_{1-4}$alkyl, or where $R^7$ is hydrogen and $R^8$ represents optionally substituted phenyl or alkyl substituted by hydroxy, $-OR^4$, $-O-C(=O)-R^6$ or $-NY^1Y^2$.

11. A compound according to claim 1 in which $L^2$ represents

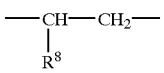

where $R^8$ is $C_{1-4}$ alkyl, optionally substituted phenyl, or $C_{1-4}$ alkyl substituted by hydroxy, $-OR^6$, $-O-C(=O)-R^6$ or $-NY^1Y^2$.

12. A compound according to claim 1 in which the group

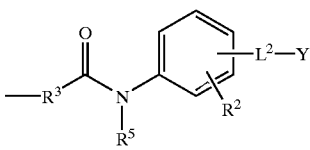

is attached at the ring 6 position.

13. A compound according to claim 1 in which the group $-L^2-Y$ is attached at the 4' position of the phenyl ring.

14. A compound according to claim 1 of the following formula:

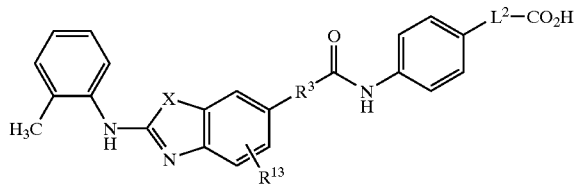

in which $R^{13}$ is selected from hydrogen, $C_{1-4}$ alkyl or methoxy, $R^3$ is $C_{1-2}$ alkylene, and $L^2$ is alkylene optionally substituted by phenyl or by alkyl substituted by hydroxy, and their prodrugs and pharmaceutically acceptable salts, and solvates of compounds of said formula and their prodrugs.

15. A compound according to claim 14 in which $R^{13}$ represents hydrogen, methyl, ethyl or methoxy.

16. A compound according to claim 14 in which $R^3$ represents methylene.

17. A compound according to claim 1 selected from the group consisting of:

(R) 3-{4-[2-(2-o-tolylaminobenzoxazol-6-yl)-acetylamino]-phenyl}-butanoic acid, (R) 3-{4-[2-(2-o-tolylamino-3H-benzimidazol-5-yl)-acetylamino]-phenyl}-butanoic acid dihydrate, (R) 3-{4-[2-(4-methoxy-2-o-tolylaminobenzoxazol-6-yl)-acetylamino]-phenyl}-butanoic acid, (R) 3-{4-[2-(4-methyl-2-o-tolylaminobenzoxazol-6-yl)-acetylamino]-phenyl}-butanoic acid, (R) 3-{4-[2-(4-ethyl-2-o-tolylaminobenzoxazol-6-yl)-acetylamino]-phenyl}-butanoic acid, (R,S) 3-phenyl-3-[4-(2-o-tolylamino-benzoxazol-6-yl)-acetylamino]-phenyl]-propanoic acid, (R) 3-{4-[3-(2-o-tolylamino-benzoxazol-6-yl)-propanoylamino]-phenyl}-butanoic acid, 6-hydroxy-3-{4-[2-(2-o-tolylamino-benzoxazol-6-yl)-acetylamino]-phenyl}-hexanoic acid, and lithium 6-hydroxy-3-{4-[2-(2-o-tolylamino-3H-benzimidazol-5-yl)-acetylamino]-phenyl}-hexanoate trifluoroacetate.

18. A pharmaceutical composition comprising an effective amount of a compound according to claim 1 or a corresponding N-oxide or prodrug, or a pharmaceutically acceptable salt or solvate of such a compound or an N-oxide prodrug thereof, in association with a pharmaceutically acceptable carrier or excipient.

19. A method for the treatment of a human or non-human animal patient suffering from, or subject to, a condition which can be ameliorated by the administration of an inhibitor of $\alpha 4\beta 1$ mediated cell adhesion comprising administering to said patient an effective amount of a compound according to claim 1 or a corresponding N-oxide or prodrug, or a pharmaceutically acceptable salt or solvate of such a compound or an N-oxide or prodrug thereof.

20. A method for the treatment of a patient suffering from, or subject to, asthma comprising administering to said patient an effective amount of a compound according to claim 1 or a corresponding N-oxide or prodrug, or a pharmaceutically acceptable salt or solvate of such a compound or an N-oxide or prodrug thereof.

21. A method for the treatment of a patient suffering from, or subject to, an inflammatory disease comprising administering to said patient an effective amount of a compound according to claim 1 or a corresponding N-oxide or prodrug, or a pharmaceutically acceptable salt or solvate of such a compound or an N-oxide or prodrug thereof.

22. A method for the treatment of a human or non-human animal patient suffering from, or subject to, a condition which can be ameliorated by the administration of an inhibitor of $\alpha 4\beta 1$ mediated cell adhesion comprising administering to said patient an effective amount of a composition according to claim 18.

23. A method for the treatment of a patient suffering from, or subject to, asthma comprising administering to said patient an effective amount of a composition according to claim 18.

24. A method for the treatment of a patient suffering from, or subject to, an inflammatory disease comprising administering to said patient an effective amount of a composition according to claim 18.

\* \* \* \* \*